(12) United States Patent
Fischer et al.

(10) Patent No.: US 10,508,108 B2
(45) Date of Patent: Dec. 17, 2019

(54) TRICYCLIC COMPOUNDS AS INHIBITORS OF MUTANT IDH ENZYMES

(71) Applicant: Merck Sharp & Dohme Corp., Rahway, NJ (US)

(72) Inventors: Christian Fischer, Boston, MA (US); Stephane L. Bogen, Rahway, NJ (US); Matthew L. Childers, Boston, MA (US); Francesc Xavier Fradera Llinas, Boston, MA (US); J. Michael Ellis, Boston, MA (US); Sara Esposite, Neptune, NJ (US); Dawn M. Hoffman, Boston, MA (US); Chunhui Huang, Kenilworth, NJ (US); Solomon D. Kattar, Boston, MA (US); Alexander J. Kim, Rahway, NJ (US); John W. Lampe, Cary, NJ (US); Michelle R. Machacek, Boston, MA (US); Daniel R. McMasters, Boston, MA (US); Dann L. Parker, Jr., Rahway, NJ (US); Michael H. Reutershan, Boston, MA (US); Nunzio Sciammetta, Boston, MA (US); Pengcheng P. Shao, Fanwood, NJ (US); David L. Sloman, Boston, MA (US); Wanying Sun, Kenilworth, NJ (US); Feroze Ujjainwalla, Kenilworth, NJ (US); Zhicai Wu, Kenilworth, NJ (US); Yang Yu, Kenilworth, NJ (US); Craig R. Gibeau, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/532,552

(22) PCT Filed: Dec. 1, 2015

(86) PCT No.: PCT/US2015/063127
§ 371 (c)(1),
(2) Date: Jun. 2, 2017

(87) PCT Pub. No.: WO2016/089830
PCT Pub. Date: Jun. 9, 2016

(65) Prior Publication Data
US 2017/0362220 A1  Dec. 21, 2017

Related U.S. Application Data

(60) Provisional application No. 62/088,272, filed on Dec. 5, 2014.

(51) Int. Cl.
*C07D 471/04* (2006.01)
*C07D 471/14* (2006.01)
*C07D 519/00* (2006.01)

(52) U.S. Cl.
CPC ......... *C07D 471/04* (2013.01); *C07D 471/14* (2013.01); *C07D 519/00* (2013.01)

(58) Field of Classification Search
CPC ... C07D 471/04; C07D 471/14; A61K 35/551
See application file for complete search history.

(56) References Cited

U.S. PATENT DOCUMENTS 6,235,900 B1  5/2001  Failli et al.
6,620,807 B1 * 9/2003  Steffan .............. C07D 471/04
                                                514/211.1

(Continued)

FOREIGN PATENT DOCUMENTS

| WO | WO1997000252 A1 | 1/1997 | |
| WO | WO2000043398 A1 | 7/2000 | |
| WO | WO-0046225 A2 * | 8/2000 | ........... C07D 471/04 |
| WO | WO2004069245 A1 | 8/2004 | |
| WO | WO2006021213 | 3/2006 | |
| WO | WO2006097449 | 9/2006 | |

(Continued)

OTHER PUBLICATIONS

T. Matsufuji et al., 24 Bioorganic & Medicinal Chemistry Letters, 750-755 (2014) (Year: 2014).*

*Primary Examiner* — Alexander R Pagano
(74) *Attorney, Agent, or Firm* — Yong Zhao; Anna L. Cocuzzo

(57) ABSTRACT

The present invention is directed to tricyclic compounds of formula (I) which are inhibitors of one or more mutant IDH enzymes (I); wherein A is —C($R^1$)= or —N=; and X is selected from the group consisting of: (II-i), and (II-ii). The present invention is also directed to uses of the tricyclic compounds described herein in the potential treatment or prevention of cancers in which one or more mutant IDH enzymes are involved. The present invention is also directed to compositions comprising these compounds. The present invention is also directed to uses of these compositions in the potential prevention or treatment of such cancers.

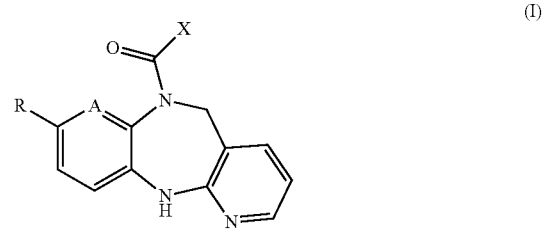

(I)

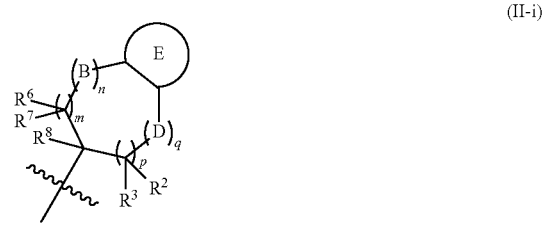

(II-i)

(Continued)

-continued

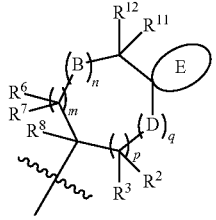

(II-ii)

20 Claims, No Drawings

(56) References Cited

U.S. PATENT DOCUMENTS

| | | | |
|---|---|---|---|
| 7,022,699 B2 | 4/2006 | Failli et al. | |
| 7,465,722 B2 | 12/2008 | Failli et al. | |
| 7,790,739 B2 | 9/2010 | Lim et al. | |
| 10,086,000 B2 * | 10/2018 | Fischer | C07D 471/04 |
| 2009/0227565 A1 | 9/2009 | Failli et al. | |
| 2017/0360800 A1 * | 12/2017 | Fischer | C07D 471/04 |

FOREIGN PATENT DOCUMENTS

| | | | | |
|---|---|---|---|---|
| WO | 2014141153 A1 | 9/2014 | | |
| WO | WO-2016089833 A1 * | 6/2016 | | C07D 471/04 |

* cited by examiner

TRICYCLIC COMPOUNDS AS INHIBITORS OF MUTANT IDH ENZYMES

CROSS REFERENCE TO RELATED APPLICATIONS

This application is a U.S. National Phase application under 35 U.S.C. § 371 of PCT Application No PCT/US2015/063127 filed Dec. 1, 2015, which claims priority from U.S. Provisional Application Ser. No. 62/088,272, filed Dec. 5, 2014.

BACKGROUND OF THE INVENTION

Isocitrate dehydrogenase (IDH) is a family of enzymes found in cellular metabolism. They are $NADP^+/NAD^+$ and metal dependent oxidoreductases of the enzyme class EC 1.1.1.42. The wild type proteins catalyze the oxidative decarboxylation of isocitrate to alpha-ketoglutarate, generating carbon dioxide and NADPH/NADH in the process. They are also known to convert oxalosuccinate into alpha-ketoglutarate. Mutations in IDH1 (cytosolic) and IDH2 (mitochondrial) have been identified in multiple cancer types including, but not limited to, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma. (See L. Dang et al., Trends Mol. Med., 2010, 16, 387; T. Shibata et al., Am. J. Pathol., 2011, 178(3), 1395; Gaal et al., J. Clin. Endocrinol. Metab. 2010, 95(3), 1274; Balss et al., Acta Neuropathol., 2008, 116, 597). The mutations have been found at or near key residues in the active site: G97D, R100Q, R132H, H133Q, and A134D for IDH1, and R140 and R172 for IDH2. (See L. Dang et al., Nature, 2009, 462, 739; L. Sellner et al., Eur. J. Haematol., 2010, 85, 457).

These mutant forms of IDH are believed to have a neomorphic activity, reducing alpha-ketoglutarate to 2-hydroxyglutarate (2-HG). (See P. S. Ward et al., Cancer Cell, 2010, 17, 225) In general, production of 2-HG is enantio-specific, resulting in generation of the D-enantiomer (also known as the R enantiomer or R-2-HG). Normal cells generally have low native levels of 2-HG, whereas cells harboring these mutations in IDH1 or IDH2 show significantly elevated levels of 2-HG. High levels of 2-HG have also been detected in tumors harboring the mutations. High levels of 2-HG have been detected in the plasma of patients with mutant IDH containing AML. (See S. Gross et al., J. Exp. Med., 2010, 207(2), 339).

Mutations in IDH1 have been associated with multiple cancers and patients having these disorders often have increased levels of 2-HG in their urine, plasma or cerebrospinal fluid. (See M. Kranendijk et al., Science, 2010, 330, 336) There is a continuing need for small molecule inhibitors of mutant IDH enzymes, or more specifically IDH1 enzymes, for the treatment of diseases and disorders associated with these enzymes.

SUMMARY OF THE INVENTION

The present invention is directed to tricyclic compounds of formula (I) which are inhibitors of one or more mutant IDH enzymes. The present invention is also directed to uses of the tricyclic compounds described herein in the potential treatment or prevention of cancers in which one or more mutant IDH enzymes are involved. The present invention is also directed to compositions comprising these compounds. The present invention is further directed to uses of these compositions in the potential prevention or treatment of such cancers.

DETAILED DESCRIPTION OF THE INVENTION

The present invention is directed to compounds of formula (I):

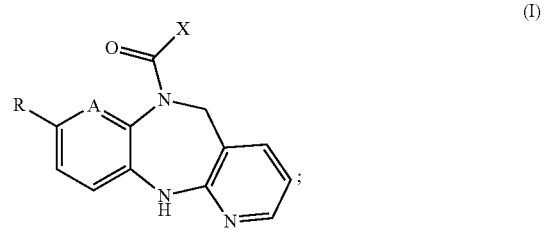

(I)

wherein A is $-C(R^1)=$ or $-N=$, and $R^1$ is hydrogen or hydroxyl;
X is selected from the group consisting of:

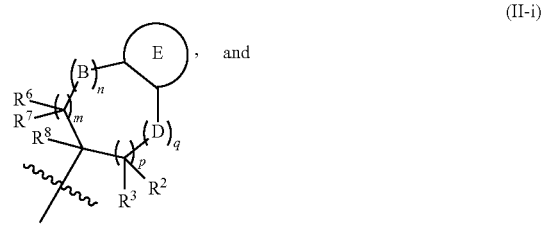

(II-i)

and

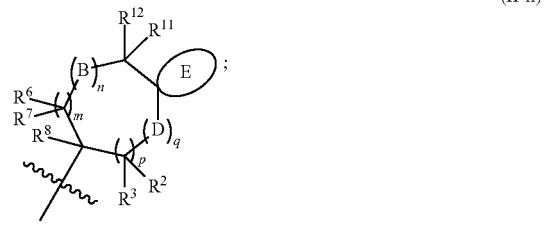

(II-ii)

B is $-C(R^9)(R^{10})-$, $-N(R^{10})-$, $-O-$, $-S-$ or $-S(O)_2-$;
D is $-C(R^4)(R^5)-$, $-N(R^5)-$, $-O-$ or $-S-$;
m is 0 or 1; n is 0 or 1; p is 0 or 1; q is 0 or 1;
the E ring is a $C_{3-6}$carbocyclic ring or a 3-6 membered saturated, partially unsaturated or aromatic heterocyclic ring containing 1-2 heteroatoms independently selected from O, S and N; the E ring is optionally substituted with one to four substituents independently selected from $R^b$; and optionally, the E ring is further fused to another 4-6 membered carbocyclic ring;
R is selected from the group consisting of:
(1) halogen,
(2) $-CN$, and
(3) $-(C=O)_t-R^a$, wherein t is 0 or 1;
$R^2$ and $R^3$ together form an oxo; or alternatively, each occurrence of $R^2$ and $R^3$ is independently selected from the group consisting of:
(1) hydrogen,
(2) $C_{1-6}$alkyl, and
(3) $-O-C_{1-6}$alkyl;

each occurrence of $R^4$, $R^6$, $R^7$, R9, $R^{11}$ and $R^{12}$ is independently selected from the group consisting of:
(1) halogen,
(2) —CN, and
(3) —(C=O)$_t$—$R^a$, wherein t is 0 or 1;
each occurrence of R5 and R10 is independently selected from the group consisting of:
(1) hydrogen, and
(2) $C_{1-6}$alkyl;
$R^8$ is selected from the group consisting of:
(1) hydrogen,
(2) —CN, and
(3) $C_{1-6}$alkyl;
each occurrence of Ra is independently selected from the group consisting of:
(1) hydrogen,
(2) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) phenyl;
  wherein each of the $C_{1-6}$alkyl of (b) and $C_{3-7}$cycloalkyl of (c) is optionally substituted with one to four substituents independently selected from $R^b$,
(3) —NR$^x$R$^y$, wherein each of R$^x$ and R$^y$ is independently selected from the group consisting of (a) hydrogen, (b) $C_{1-6}$alkyl, (c) $C_{3-6}$cycloalkyl, (d) —O—$C_{1-6}$alkyl, (e) phenyl optionally substituted with one to four halogens, and (f) heterocyclyl;
  wherein the $C_{1-6}$alkyl of (b) is optionally substituted with one to four substituents independently selected from halogen, —O—$C_{1-4}$alkyl, $C_{3-6}$cycloalkyl, and heterocyclyl; and
  the $C_{3-6}$cycloalkyl of (c) is optionally substituted with one to four substituents independently selected from halogen, —O—$C_{1-4}$alkyl, $C_{3-6}$cycloalkyl, heterocyclyl, and $C_{1-4}$alkyl, which is optionally substituted with one to four halogens,
  the heterocyclyl of (f) is optionally substituted with one to four substituents independently selected from halogen, $C_{1-4}$alkyl, —O—$C_{1-4}$alkyl, $C_{3-6}$cycloalkyl, and heterocyclyl,
(4) $C_{2-6}$alkenyl, optionally substituted with one to four substituents independently selected from $R^b$,
(5) $C_{5-6}$cycloalkenyl, optionally substituted with one to four substituents independently selected from $R^b$,
(6) aryl, optionally substituted with one to four substituents independently selected from $R^b$, and
(7) heterocyclyl, optionally substituted with one to four substituents independently selected from R$_b$;
each occurrence of $R^b$ is independently selected from the group consisting of:
(1) halogen,
(2) —CN,
(3) oxo,
(4) —(O)$_t$—$R^d$, wherein t is 0 or 1; $R^d$ is selected from the group consisting of (a) hydrogen, (b) $C_{1-6}$alkyl, (c) $C_{3-7}$cycloalkyl, and (d) heterocyclyl;
  wherein the $C_{1-6}$alkyl of (b) is optionally substituted with one to four substituents independently selected from (i) halogen, (ii) hydroxyl, (iii) —O—$C_{1-6}$alkyl, (iv) $C_{3-6}$cycloalkyl optionally substituted with 1-3 halogens, (v) —NR$^x$R$^y$, wherein each of R$^x$ and R$^y$ is independently selected from the group consisting of hydrogen, $C_{1-6}$alkyl, $C_{3-6}$cycloalkyl, phenyl optionally substituted with one to four halogens, and heterocyclyl, and (vi) heterocyclyl;
  the $C_{3-7}$cycloalkyl of (c) is optionally substituted with one to four substituents independently selected from (i) halogen, and (ii) $C_{1-6}$alkyl, which is optionally substituted with one to four halogens, and (iii) —CN; and
  the heterocyclyl of (d) is optionally substituted with one to four substituents independently selected from (i) halogen, (ii) hydroxyl, (iii) oxo, (iv) $C_{1-6}$alkyl optionally substituted with one to four halogens, (v) —O—$C_{1-6}$alkyl, (vi) heterocyclyl optionally substituted with halogen or hydroxyl, and (vii) —NR$^j$R$^k$;
  wherein each of R$^j$ and R$^k$ is independently selected from the group consisting of hydrogen and $C_{1-6}$alkyl,
(5) —(C=O)$_t$—$R^c$, wherein t is 0 or 1; $R^c$ is selected from the group consisting of hydrogen, hydroxyl, $C_{1-6}$alkyl, $C_{2-6}$alkenyl, —O—$C_{1-6}$alkyl, —NR$^x$R$^y$, and heterocyclyl;
  wherein each of R$^x$ and R$^y$ is independently selected from the group consisting of (a) hydrogen, (b) $C_{1-6}$alkyl, (c) $C_{2-6}$alkenyl, (d) $C_{3-6}$cycloalkyl, (e) phenyl optionally substituted with one to four halogens, and (f) heterocyclyl;
  wherein the $C_{1-6}$alkyl of (b) is optionally substituted with one to four substituents independently selected from halogen, —O—$C_{1-4}$alkyl, $C_{3-6}$cycloalkyl, heterocyclyl, and —(C=O)—NR$^j$R$^k$, wherein each of R$^j$ and R$^k$ is independently hydrogen or $C_{1-6}$alkyl;
  the $C_{3-6}$cyclolkyl of (d) is optionally substituted with one to four substituents independently selected from halogen and $C_{1-4}$alkyl, which is optionally substituted with one to four halogens, and
  the heterocyclyl of (f) is optionally substituted with one to four substituents independently selected from halogen, —CN, $C_{1-6}$alkyl, and —O—$C_{1-6}$alkyl,
(6) $C_{2-6}$alkenyl, and
(7) phenyl, optionally substituted with one to four substituents independently selected from halogen, $C_{1-6}$alkyl, and —O—$C_{1-6}$alkyl;
or pharmaceutically acceptable salts thereof.

In an embodiment of the previous embodiment, compounds disclose herein are of the following formula:

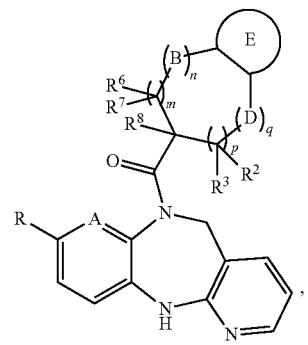

(Ia)

wherein A is —CH=, —C(OH)=, or —N=;
B is —CH(R$^9$)—, —NH—, or —O—;
D is —CH(R$^4$)—, —NH—, or —O—;
the E ring is a $C^{3-6}$carbocyclic ring or a 3-6 membered saturated, partially unsaturated or aromatic heterocyclic ring containing 1-2 heteroatoms independently selected from O, S and N; and the E ring is optionally substituted with one to four substituents independently selected from $R^b$; and
$R_2$, $R^3$, $R^6$, $R^7$, $R^8$, $R^b$, R, m, n, p, and q are as previously described.

In an embodiment of each previous embodiment, a compound is selected from the group consisting of:
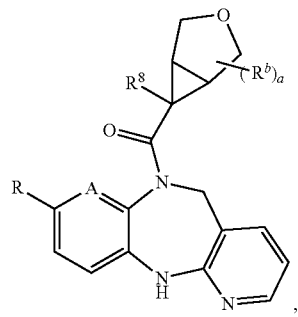
(Ia-i)
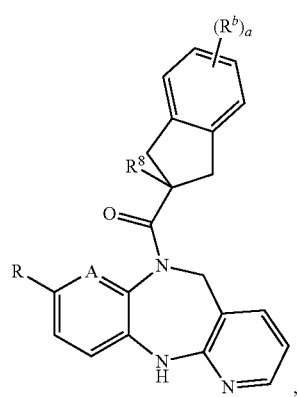
(Ia-ii)
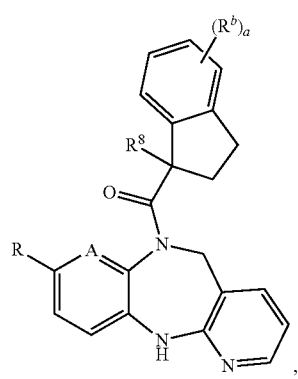
(Ia-iii)
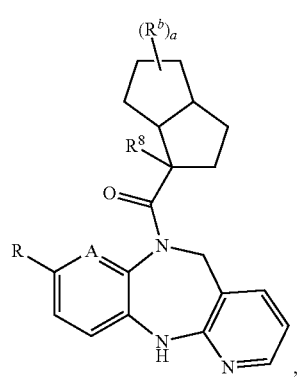
(Ia-iv)
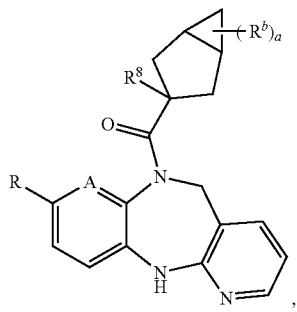
(Ia-v)
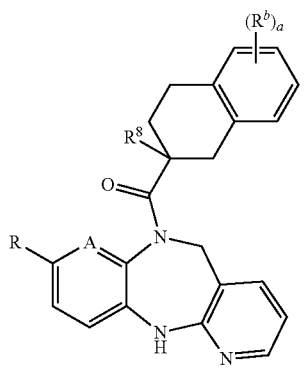
(Ia-vi)
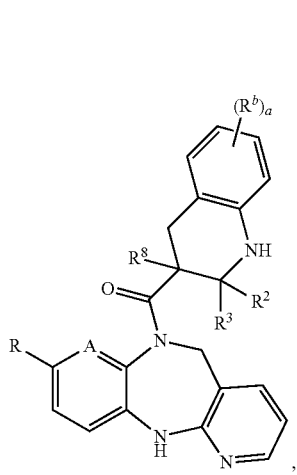
(Ia-vii)
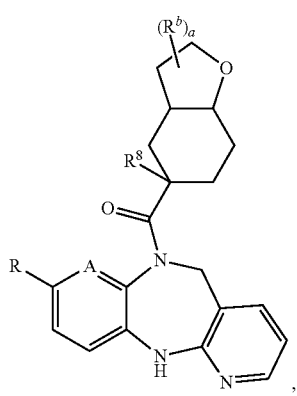
(Ia-viii)

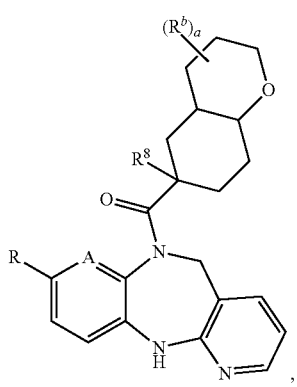
(Ia-ix)
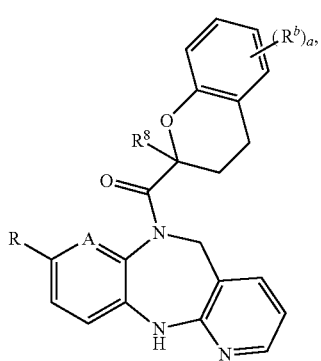
(Ia-x)
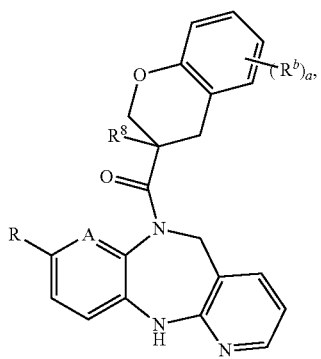
(Ia-xi)
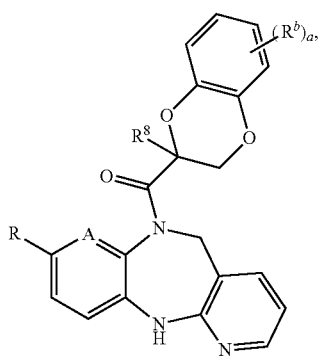
(Ia-xii)
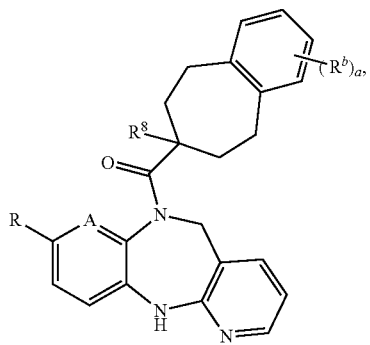
(Ia-xiii)
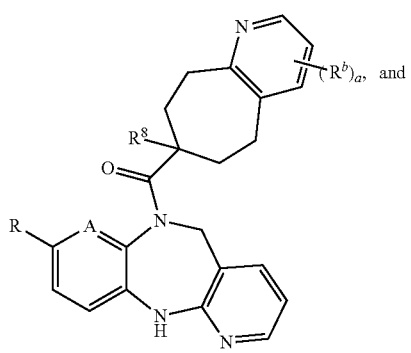
(Ia-xiv)
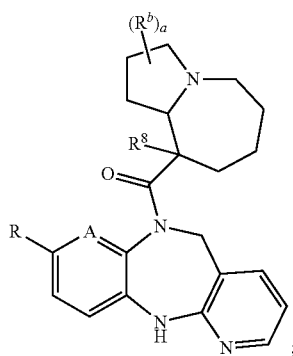
(Ia-xv)
wherein A is —CH=, —C(OH)=, or —N=;
$R^2$ and $R^3$ together form an oxo; or alternatively, each of $R^2$ and $R^3$ is hydrogen; and
a is 0, 1 or 2; when a is 2, the two $R^b$ substituents are attached to the same or different substitutable positions on the fused ring; and
$R^8$, $R_b$, and R are as previously described.

In an embodiment of each previous embodiment, a compound is of the following formula:

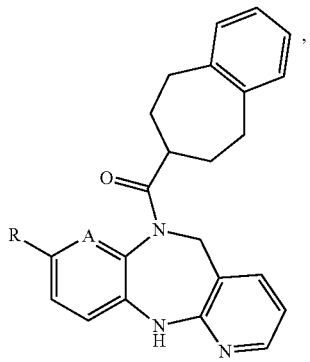

(Ia-xvi)

wherein A is —CH═, —C(OH)═, or —N═, and R is as previously described.

In one embodiment, a compound is of the following formula:

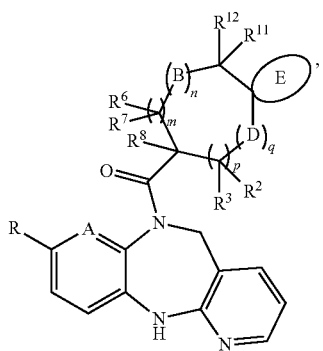

(Ib)

wherein A is —CH═, —C(OH)═, or —N═;

the E ring is a $C_{3-6}$carbocyclic ring or a 3-6 membered saturated, partially unsaturated or aromatic heterocyclic ring containing 1 or 2 heteroatoms independently selected from O, S and N; and the E ring is optionally substituted with one to three substituents independently selected from $R^b$; and $R^2$, $R^3$, $R^6$, $R^7$, $R^8$, $R^b$, B, D, R, m, n, p, and q are as previously described.

In an embodiment of each previous embodiment, when present, the E ring is selected from the group consisting of:

azetidinyl, $C_{3-6}$cycloalkyl, oxetanyl, phenyl, pyridinyl, pyrrolidinyl, tetrahydrofuranyl, and tetrahydropyranyl.

In one embodiment, a compound is of the following formula:

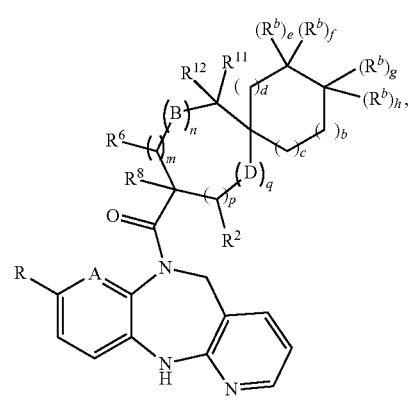

(Ib-i)

wherein A is —CH═, —C(OH)═, or —N═;
b is 0 or 1; c is 0 or 1; d is 0 or 1;
e is 0 or 1; f is 0 or 1; g is 0 or 1; h is 0 or 1; and
$R^2$, $R^6$, $R^8$, $R^{11}$, $R^{12}$, $R^b$, B, D, R, m, n, p, and q are as previously described.

In one embodiment, a compound is selected from the group consisting of:

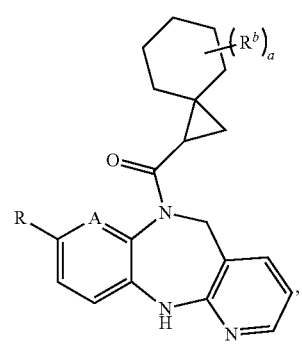

(Ib-ii)

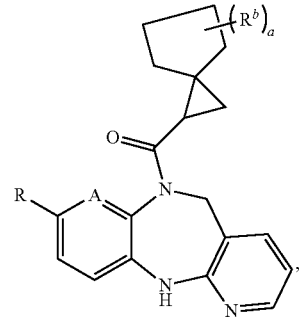

(Ib-iii)

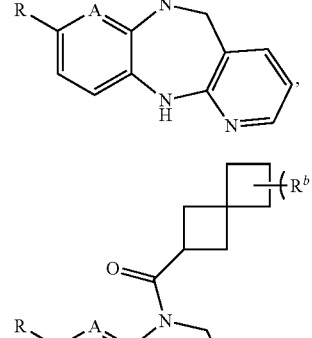

(Ib-iv)

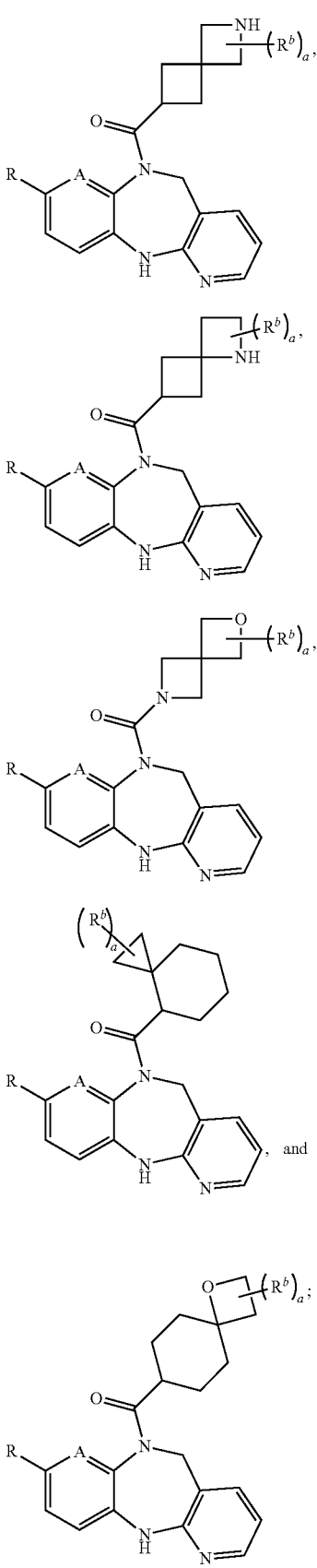

wherein a is 0, 1, or 2; when a is 2, the two $R^b$ substituents are attached to the same or different substitutable positions on the spiro ring; and $R^b$, A and R are as previously described.

In an embodiment of each previous embodiment, each occurrence of $R^4$, $R^6$, $R^7$, $R^9$, $R^{11}$ and $R^{12}$, when present, is independently selected from the group consisting of hydrogen and $C_{1-6}$alkyl, which is optionally substituted with one to four halogens.

In an embodiment of each previous embodiment, $R^8$ is hydrogen or $C_{1-4}$alkyl.

In an embodiment of each previous embodiment, R is selected from the group consisting of:
(1) hydrogen,
(2) halogen,
(3) $C_{1-6}$alkyl, optionally substituted with one to four substituents independently selected from (a) halogen, (b) —CN, (c) —$OR^d$, (d) —(C=O)—$R^e$, (e) —$NR^xR^y$, and (f) heterocyclyl; wherein $R^d$ is hydrogen or $C_{1-4}$alkyl, which is optionally substituted with heterocyclyl;
$R^e$ is hydroxyl or heterocyclyl;
each of $R^x$ and $R^y$ is independently selected from the group consisting of (i) hydrogen, (ii) $C_{1-6}$alkyl, which is optionally substituted with one to four substituents independently selected from halogen, —O—$C_{1-4}$alkyl, $C_{3-6}$cycloalkyl, and heterocyclyl, (iii) $C_{3-6}$cycloalkyl, which is optionally substituted with one to four substituents independently selected from halogen, and $C_{1-4}$alkyl, which is optionally substituted with one to four halogens, and (iv) heterocyclyl;
(4) —O—$C_{1-6}$alkyl,
(5) —(C=O)$_t$—$NR^xR^y$, wherein t is 0 or 1; each of $R^x$ and $R^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl; wherein the $C_{1-6}$alkyl of (b) is optionally substituted with one to four substituents independently selected from halogen, —O—$C_{1-4}$alkyl, $C_{3-6}$cycloalkyl, and heterocyclyl; and
the $C_{3-6}$cycloalkyl of (c) is optionally substituted with one to four substituents independently selected from halogen and $C_{1-4}$alkyl optionally substituted with one to four halogens, and
(6) —(C=O)$_t$-heterocyclyl, wherein t is 0 or 1; and the heterocyclyl is optionally substituted with one to four substituents independently selected from $R^b$.

In an embodiment of each previous embodiment, each occurrence of $R^b$ is independently selected from the group consisting of:
(1) halogen,
(2) hydroxyl,
(3) —CN,
(4) oxo,
(5) —O—$C_{1-6}$alkyl,
(6) —(C=O)—$R^c$, wherein Rc is selected from the group consisting of hydrogen, hydroxyl, $C_{1-6}$alkyl, —O—$C_{1-6}$alkyl, —$NR^jR^k$, and heterocyclyl; wherein the heterocyclyl is optionally substituted with one to four substituents independently selected from halogen and $C_{1-6}$alkyl; and each of $R^j$ and $R^k$ is independently selected from the group consisting of hydrogen and $C_{1-6}$alkyl,
(7) $C_{1-6}$alkyl, optionally substituted with one to four halogens, (8) phenyl, optionally substituted with one to four halogens, and (9) heterocyclyl, optionally substituted with one to four substituents independently selected from halogen, oxo, $C_{1-6}$alkyl optionally substituted with one to four halogens, —O—$C_{1-6}$alkyl, heterocyclyl optionally substituted with halogen or hydroxyl, and —NR$^j$R$^k$; wherein each of R$^j$ and R$^k$ is independently selected from the group consisting of hydrogen and $C_{1-6}$alkyl.

In an embodiment of each previous embodiment, each occurrence of R$^b$ is independently selected from the group consisting of:
(1) halogen,
(2) hydroxyl,
(3) oxo,
(4) —O—$C_{1-6}$alkyl,
(5) —(C=O)—R$^c$, wherein R$^c$ is selected from the group consisting of hydrogen, hydroxyl, and $C_{1-6}$alkyl, and
(6) $C_{1-6}$alkyl, optionally substituted with one to four halogens.

In an embodiment of each previous embodiment, each occurrence of the heterocyclyl of R and R$^b$ is independently selected from the group consisting of: 8-azabicyclo[3.2.1]octanyl, 2-azaspiro[3.3]heptanyl, azaindolyl, azetidinyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 3,4-dihydro-2H-pyrido[3,2-b][1,4]oxazinyl, 5,6-dihydro-4H-pyrrolo[1,2-b]pyrazolyl, 1,4-dioxanyl, hexahydro-1H-furo[3,4-c]pyrrolyl, 1,2,4,5,6,6a-hexahydropyrrolo[3,4-b]pyrrolyl, imidazolyl, 1H-imidazo[4,5-b]pyridinyl, isoindolinyl, isoxazolyl, morpholinyl, octahydrocyclopenta[1,4]oxazinyl, octahydro-1H-imidazo[4,5-c]pyridinyl, 2-oxa-5-azabicyclo[2.2.1]heptanyl, 3-oxa-6-azabicyclo[3.2.0]heptanyl, 6-oxa-3-azabicyclo[3.1.1]heptanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro[3.4]octanyl, 3-oxa-1,7-diazaspiro[4.4]nonanyl, 1,4-oxazepanyl, oxazolidinyl, oxetanyl, piperazinyl, piperidinyl, pyrazolo[1,5-b]pyridazinyl, pyrazolyl, pyridazinyl, pyridinyl, pyrimidinyl, pyrrolidinyl, pyrrolyl, tetrahydrofuranyl, 5,6,7,8-tetrahydroimidazo[1,5-a]pyrazinyl, tetrahydropyranyl, 4,5,6,7-tetrahydropyrazolo[1,5-a]pyrazinyl, 4,5,6,7-tetrahydro-2H-pyrazolo[4,3-c]pyridinyl, 1,2,3,6-tetrahydropyridinyl, 1,2,3,4-tetrahydropyrrolo[1,2-a]pyrazinyl, 4,5,6,7-tetrahydro-[1,2,3]triazolo[1,5-a]pyrazinyl, 5,6,7,8-tetrahydro-[1,2,4]triazolo[4,3-a]pyrazinyl, 5,6,7,8-tetrahydro-[1,2,4]triazolo[1,5-a]pyrazinyl, thiazolyl, and thiophenyl.

In an embodiment of each previous embodiment, R is selected from the group consisting of:
(1) hydrogen,
(2) $C_{1-6}$alkyl, optionally substituted with one to four substituents independently selected from halogen, —CN, and —OR$^d$; wherein R$^d$ is hydrogen or $C_{1-4}$alkyl optionally substituted with heterocyclyl,
(3) —NR$^j$R$^k$, wherein each of R$^j$ and R$^k$ is independently selected from the group consisting of hydrogen and $C_{1-6}$alkyl; wherein the $C_{1-6}$alkyl is optionally substituted with one to four halogens, and
(4) —(C=O)-heterocyclyl, wherein the heterocyclyl is optionally substituted with halogen or $C_{1-6}$alkyl, and
(5) heterocyclyl, optionally substituted with one to four substituents independently selected from the group consisting of halogen, oxo, —O—$C_{1-6}$alkyl, $C_{1-6}$alkyl optionally substituted with one to four halogens, —NR$^j$R$^k$, and heterocyclyl optionally substituted with halogen or hydroxyl; wherein each of R$^j$ and R$^k$ is independently selected from the group consisting of hydrogen and $C_{1-6}$alkyl, wherein each occurrence of the heterocyclyl of (2), (4) and (5) is independently selected from the group consisting of azaindolyl, azetidinyl, 1,4-dioxanyl, imidazolyl, isoindolinyl, isoxazolyl, morpholinyl, oxazolidinyl, piperidinyl, pyridinyl, pyrazolyl, pyrrolidinyl, tetrahydropyranyl, and thiazolyl.

In one embodiment, a compound is selected from the subject compounds of the Examples herein, or a pharmaceutically acceptable salt thereof. In one embodiment, the compound is selected from the compounds in Examples 3-5, 9-14, 18-21, 23, 34-56, 62-66, 68-72, 79-92, 94-100, and 102-108.

In one embodiment, disclosed herein is a composition which comprises an inert carrier and a compound of formula (I), or a pharmaceutically acceptable salt thereof.

In one embodiment, disclosed herein is a method for treating a disease or disorder associated with a mutant IDH enzyme in a subject which comprises administering to the subject an effective amount of a compound of formula (I), or a pharmaceutically acceptable salt thereof.

In one embodiment, disclosed herein is the use of a compound of formula (I), or a pharmaceutically acceptable salt thereof, for the manufacture of a medicament for the treatment or prevention of a disease or disorder associated with a mutant IDH enzyme.

In one embodiment, a method for treating a disease or disorder associated with a mutant IDH enzyme in a subject comprises administering to the subject an effective amount of a compound of formula (I), or a pharmaceutically acceptable salt thereof, in combination with another anti-cancer agent.

In one embodiment, the disease or disorder associated with a mutant IDH enzyme is cancer. In one embodiment, the cancer is selected from the group consisting of glioma, glioblastoma multiforme, paraganglioma, supratentorial primordial neuroectodermal tumors, acute myeloid leukemia (AML), breast cancer, prostate cancer, thyroid cancer, colon cancer, chondrosarcoma, cholangiocarcinoma, peripheral T-cell lymphoma, and melanoma. In one embodiment, the cancer is selected from glioma, glioblastoma multiforme, acute myeloid leukemia, and breast cancer.

As used herein, "alkenyl" refers to both branched- and straight-chain unsaturated aliphatic hydrocarbon groups of 2 to 12 carbon atoms and having at least one carbon-carbon double bond. Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkoxy" refers to any alkyl moiety attached through an oxygen bridge (e.g., a —O—$C_{1-6}$alkyl group wherein $C_{1-6}$alkyl is as defined herein). Examples of such groups include, but are not limited to, methoxy, ethoxy, propoxy, butyloxy and pentyloxy. Alkoxy groups may be optionally substituted with one or more substituents as defined herein. "$C_{1-6}$alkoxy" refers to an alkoxy group as defined herein having 1 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Carbocycle" refers to a saturated, partially unsaturated or aromatic ring moiety having only ring carbon atoms. Carbocyclyl moieties include both monocyclic and multicyclic (e.g., bicyclic) ring moieties. Bicyclic carbocyclyl moieties include fused, spirocyclic and bridged bicyclic rings. Examples of carbocyclyl moieties include, but are not limited to, cyclopentyl, cyclohexyl, cycloheptyl, cyclooctyl, cyclopentenyl, cyclohexenyl, cyclohexadienyl, phenyl, and naphthyl. Carbocyclic rings may be optionally substituted with one or more substituents as defined herein. "$C_{3-10}$carbocycle" refers to a carbocycle group as defined herein having 3 to 10 ring carbon atoms. In one embodiment, a carbocyclyl moiety is aryl.

In one embodiment, a carbocyclyl is a bridged bicyclic or multicyclic moiety. Non-limiting examples of this type of moieties include

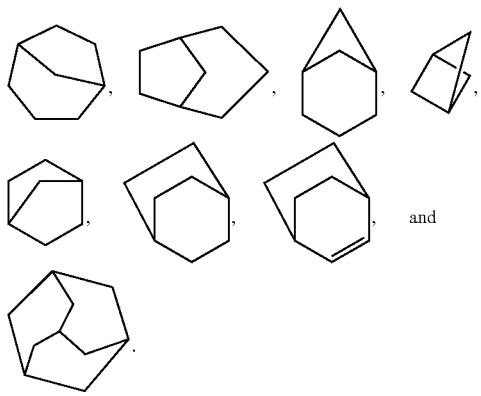

In one embodiment, a carbocycle is a $C_{3-7}$cycloalkyl. "Cycloalkyl" refers to a monocyclic saturated carbocyclic ring having the specified number of carbon atoms. For example, $C_{3-7}$ cycloalkyl refers to a cycloalkyl group as defined herein having 3 to 7 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein.

In one embodiment, a carbocyclyl moiety is a $C_{4-7}$cycloalkenyl. "Cycloalkenyl" refers to a monocyclic partially unsaturated carbocyclic ring having the specified number of carbon atoms and at least one carbon-carbon double bond. Examples of cycloalkenyl include, but are not limited to, cyclobutenyl, cyclopentenyl, cyclohexenyl, cyclohexa-1,4-dienyl, and cycloheptenyl.

"Halo" or "halogen" refers to fluoro, chloro, bromo or iodo, unless otherwise noted.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl.

In one embodiment, a heterocyclyl moiety is a fused bicyclic ring moiety wherein a 4-6 membered heterocyclic ring comprising 1-4 heteroatoms selected from oxygen, sulfur and nitrogen and a 5-6 membered heterocyclic ring comprising 1-4 heteroatoms selected from oxygen, sulfur and nitrogen are connected through two atoms. Exemplary heterocycles of this type include, but are not limited to, azaindolyl, dihydronaphthyridinyl, imidazopyridinyl, indolizinyl, naphthyridinyl, pteridinyl, purinyl, quinolizinyl, tetrahydroindolizinyl, tetrahydronaphthyridinyl, tetrahydroquinolizinyl,

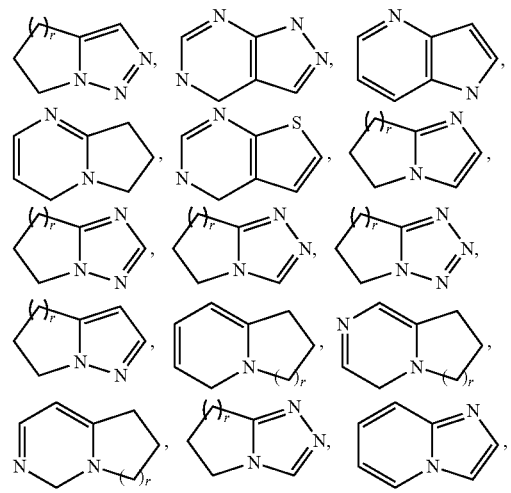

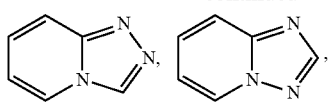 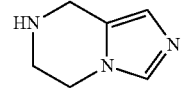

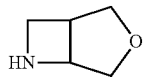

(3-oxa-6-azabicyclo[3.2.0]heptane), (5,6,7,8-tetrahydroimidazo[1,5-a]pyrazine)

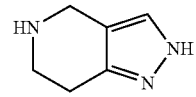

(4,5,6,7-tetrahydro-2H-pyrazolo[4,3-c]pyridine),

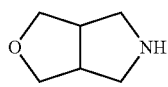

(hexahydro-1H-furo[3,4-c]pyrrole),

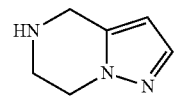

(4,5,6,7-tetrahydropyrazolo[1,5-a]pyrazine),

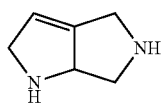

(1,2,4,5,6,6a-hexahydropyrrolo[3,4-b]pyrrole),

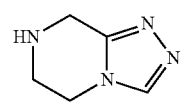

(5,6,7,8-tetrahydro-[1,2,4]triazolo[4,3-a]pyrazine),

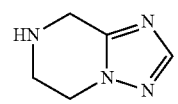

(5,6,7,8-tetrahydro-[1,2,4]triazolo[1,5-a]pyrazine),

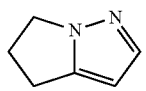

(5,6-dihydro-4H-pyrrolo[1,2-b]pyrazole),

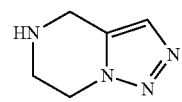

(4,5,6,7-tetrahydro-[1,2,3]triazolo[1,5-a]pyrazine),

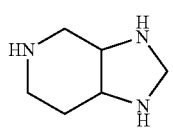

(octahydro-1H-imidazo[4,5-c]pyridine),

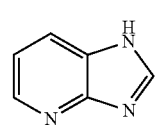

(1H-imidazo[4,5-b]pyridine),

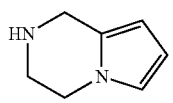

(1,2,3,4-tetrahydropyrrolo[1,2-a]pyrazine),

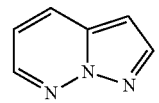

(pyrazolo[1,5-b]pyridazine), and

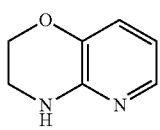

(3,4-dihydro-2H-pyrido[3,2-b][1,4]oxazine);
wherein r is 1 or 2. In one embodiment, an azaindole is

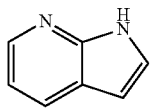

(1H-pyrrolo[2,3-b]pyridine),

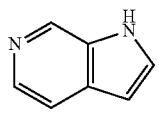

(1H-pyrrolo[2,3-c]pyridine),

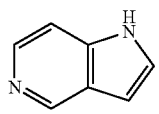

(1H-pyrrolo[3,2-c]pyridine), or

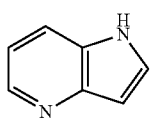

(1H-pyrrolo[3,2-b]pyridine). Such fused ring may be attached to the rest of the molecule via a carbon atom or a nitrogen atom on either ring. A heterocycle of this type includes a bicyclic ring comprising only one nitrogen as the sole heteroatom when the nitrogen is located at the bridgehead.

In one embodiment, a heterocyclyl is a fused bicyclic ring moiety wherein a 4-6 membered heterocyclic ring comprising 1-4 heteroatoms selected from oxygen, sulfur and nitrogen and a $C_{5-10}$ carbocyclic ring are connected through two carbon atoms. Exemplary heterocycles of this type include, but are not limited to, benzimidazolonyl, benzimidazolyl, benzisothiazolyl, benzisoxazolyl, benzofuranyl, benzofurazanyl, benzothienyl, benzotriazolyl, benzoxazolyl, benzthiazolyl, chromanyl, chromenyl, cinnolinyl, dihydroindazolyl, indazolyl, indolyl, isoindolyl, isoquinolinyl, quinazolinyl, quinolinyl, quinoxalinyl, tetrahydroindazolyl, tetrahydroquinolinyl,

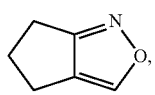 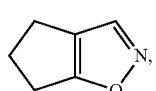 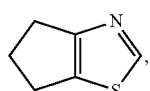

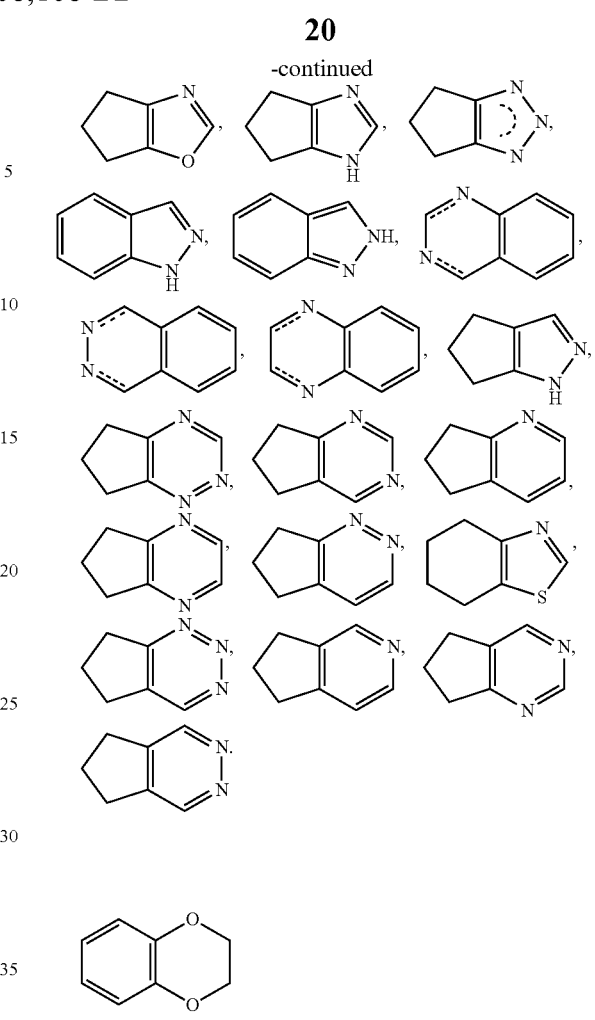

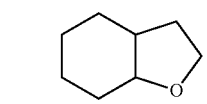

(2,3-dihydrobenzo[b][1,4]dioxine),

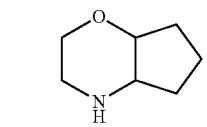

(octahydrobenzofuran),

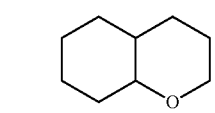

(octahydrocyclopenta[1,4]oxazine), and (octahydro-2H-chromene). Such fused ring may be attached to the rest of the molecule via a carbon atom or a nitrogen atom on either ring.

In one embodiment, a heterocyclyl is a spirocycle ("spiro") bicyclic moiety wherein two rings are connected through one atom, and either or both of the rings comprise at least one heteroatom. In one embodiment, a spiro bicyclic heterocycle comprises a 4-7 membered heterocyclic ring comprising 1-4 heteroatoms selected from oxygen, sulfur and nitrogen connected through a single atom to either a 3-6 membered ring comprising 1-2 heteroatoms selected from oxygen, sulfur and nitrogen or a 3-6 membered carbocyclic ring. Exemplary spiro heterocycles of this type include, but are not limited to:

(2-azaspiro[3.3]heptane),

(2-oxa-6-azaspiro[3.3]heptane),

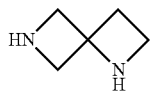

(1,6-diazaspiro[3.3]heptane),

(2,6-diazaspiro[3.3]heptane),

(6-oxa-2-azaspiro[3.4]octane),

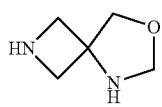

(7-oxa-2,5-diazaspiro[3.4]octane),

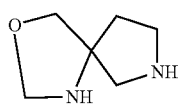

(3-oxa-1,7-diazaspiro[4.4]nonane),

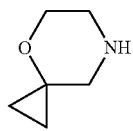

(4-oxa-7-azaspiro[2.5]octane), and

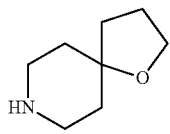

(1-oxa-8-azaspiro[4.5]decane).

Such spiro bicyclic moieties may be attached to the rest of the molecule via a carbon atom or a nitrogen atom on either ring.

In one embodiment, a heterocycle is a bridged bicyclic moiety selected from the group consisting of:

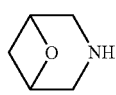

(6-oxa-3-azabicyclo[3.1.1]heptane),

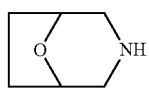

(8-oxa-3-azabicyclo[3.2.1]octane),

(2-oxa-5-azabicyclo[2.2.2]octane),

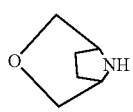

(3-oxa-8-azabicyclo[3.2.1]octane),

(2-oxa-5-azabicyclo[2.2.1]heptane),

(3,8-diazabicyclo[3.2.1]octane),

(2,5-diazabicyclo[2.2.2]octane),

(8-azabicyclo[3.2.1]octane), and

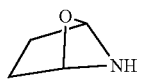

(5-oxa-6-azabicyclo[2.1.1]hexane). Such bridged bicyclic moieties may be attached to the rest of the molecule via a carbon atom or a nitrogen atom on either ring.

Heterocycles include ring moieties wherein a ring sulfur atom is oxidized to form SO and $SO_2$. In one embodiment, a heterocycle of this type is

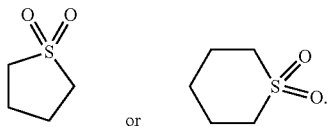 [SMILES: O=S1(=O)CCCC1 ; O=S1(=O)CCCCC1]

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

Optical Isomers—Diastereomers—Geometric Isomers—Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereoisomers). With regard to stereoisomers, a compound of formula (I) may have one or more asymmetric carbon atom and may occur as a racemic mixture or as individual enantiomers or diastereomers. All such isomeric forms are included herein, including mixtures thereof. If a compound of formula (I) contains a double bond, the substituent may be in the E or Z configuration. If a compound of formula (I) contains a disubstituted cycloalkyl, the cycloalkyl substituent may have a cis- or trans-configuration. All tautomeric forms are also intended to be included.

Any asymmetric atom (e.g., carbon) of a compound of formula (I) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula (I) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds of formula (I) can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

The compounds disclosed herein are inhibitors of a mutant IDH enzyme. These compounds are potentially useful in treating diseases or disorders associated with such enzymes including, but not limited to, cell proliferation disorders, such as cancer.

Examples of these mutant IDH enzymes are mutant IDH1 and mutant IDH2. A mutation in human IDH 1 enzyme include a mutation at amino acid residue 97, 100, or 132, e.g. G97D, R100Q, R132H, R132C, R132S, R132G, R132L, or R132V. A mutation in human IDH2 enzyme include a mutation at amino acid residue 140 or 172, e.g. R140Q, R140G, R172K, R172M, R172S, R172G, or R172W.

Cell-proliferation disorders that may be associated with a mutant IDH enzyme activity include, but are not limited to, cancer. Examples of such cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, a cancer potentially associated with mutant IDH enzyme activity is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, a cancer potentially associated with mutant IDH enzyme activity is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma and acute lymphoblastic leukemia.

In one embodiment, a cancer potentially associated with mutant IDH enzyme activity is skin cancer, including melanoma. In another embodiment, a cancer potentially associated with mutant IDH enzyme activity is prostate cancer, breast cancer, thyroid cancer, colon cancer, or lung cancer. In another embodiment, a cancer potentially associated with mutant IDH enzyme activity is sarcoma, including central chondrosarcoma, central and periosteal chondroma, and fibrosarcoma. In another embodiment, a cancer potentially associated with mutant IDH enzyme activity is cholangiocarcinoma.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder described herein that may be associated with mutant IDH enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit mutant IDH enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDH mutation by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I).

One embodiment of the present invention provides for a method of treating a disease or disorder associated with mutant IDH enzyme activity comprising administration of an effective amount of a compound of formula (I) to a subject in need of treatment thereof. In one embodiment, the disease or disorder associated with a mutant IDH enzyme is a cell proliferation disorder.

In one embodiment, the cell proliferation disorder is cancer. In another embodiment, the cancer is a cancer associated with mutant IDH1 enzyme activity. In another embodiment, the cancer is associated with human mutant IDH1 enzyme activity, having a mutation at amino acid residue 97, 100, or 132, such as G97D, R100Q, R132H, R132C, R132S, R132G, R132L, or R132V.

In one embodiment, the cancer is associated with human mutant IDH2 enzyme activity having a mutation at amino acid residue 140 or 172, e.g. R140Q, R140G, R172K, R172M, R172S, R172G, or R172W.

In one embodiment, the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of formula (I) in a therapy. The compound may be useful in a method of inhibiting mutant IDH enzyme activity in a subject, such as a mammal in need of such inhibition, comprising administering an effective amount of the compound to the subject.

In one embodiment, disclosed herein is a pharmaceutical composition comprising at least one compound of formula (I), or a pharmaceutically acceptable salt thereof, for use in potential treatment of a disorder or disease related to mutant IDH1 enzyme activity.

In one embodiment, disclosed herein is the use of a compound of formula (I) in the manufacture of a medicament for the treatment of a disease or disorder associated with mutant IDH enzyme activity. In one embodiment, the disease or disorder associated with a mutant IDH is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant a carrier or excipient is compatible with a compound disclosed herein and with other ingredients of the composition.

In one embodiment, disclosed herein is a composition comprising a compound of formula (I), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), or a pharmaceutically acceptable salt thereof.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) and one or more other active agent(s) together in the same pharmaceutical composition, or a compound of formula (I) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I) and at least one other therapeutic agent as a combined preparation for simultaneous, separate or sequential use in therapy. In one embodiment, the therapy is the treatment of a disease or disorder associated with mutant IDH enzyme activity.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

A kit of the invention may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I) for treating a disease or disorder associated with mutant IDH enzyme activity, wherein the medicament is prepared for administration with another active agent. The invention also provides the use of another active agent for treating a disease or disorder associated with a mutant IDH enzyme, wherein the medicament is administered with a compound of formula (I).

The invention also provides the use of a compound of formula (I) for treating a disease or disorder associated with mutant IDH enzyme activity, wherein the patient has previously (e.g. within 24 hours) been treated with another active agent. The invention also provides the use of another therapeutic agent for treating a disease or disorder associated with mutant IDH enzyme activity, wherein the patient has previously (e.g. within 24 hours) been treated with a compound of formula (I). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-y!)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, but are not limited to, doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-c/s-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename Keytruda®) and nivolumab (sold under the tradename Opdivo®).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename Trisenox®), asparaginase (also known as L-asparaginase, and Erwinia L-asparaginase, sold under the tradenames Elspar® and Kidrolase®).

EXPERIMENTAL

The following examples are intended to be illustrative only and not limiting in any way. Abbreviations used are those conventional in the art or the following.

ACN=acetonitrile, BSA=bovine serum albumin, ° C.=degree Celsius, DMF=N,N-dimethylformamide, DMSO=dimethylsulfoxide, DTT=dithiothreitol, EtOAc=ethyl acetate, EtOH=ethanol, g=gram, h=hour(s), HPLC=high pressure liquid chromatography, kg=kilogram, L=liter, LC=liquid chromatography, LCMS=liquid chromatography and mass spectrometry, MeOH=methanol, MS=mass spectrometry, min=minutes, ml.=milliliter(s), m/z=mass to charge ratio, nm=nanometer, nM=nanomolar, N=normal, NADPH=nicotinamide adenine dinucleotide phosphate, NMR=nuclear magnetic resonance, sat.=saturated, TEA=riethylamine, TFA=trifluoroacetic acid, THF=tetrahydrofuran, TLC=thin layer chromatography, General Synthetic Schemes The compounds of formula (I) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

Scheme 1

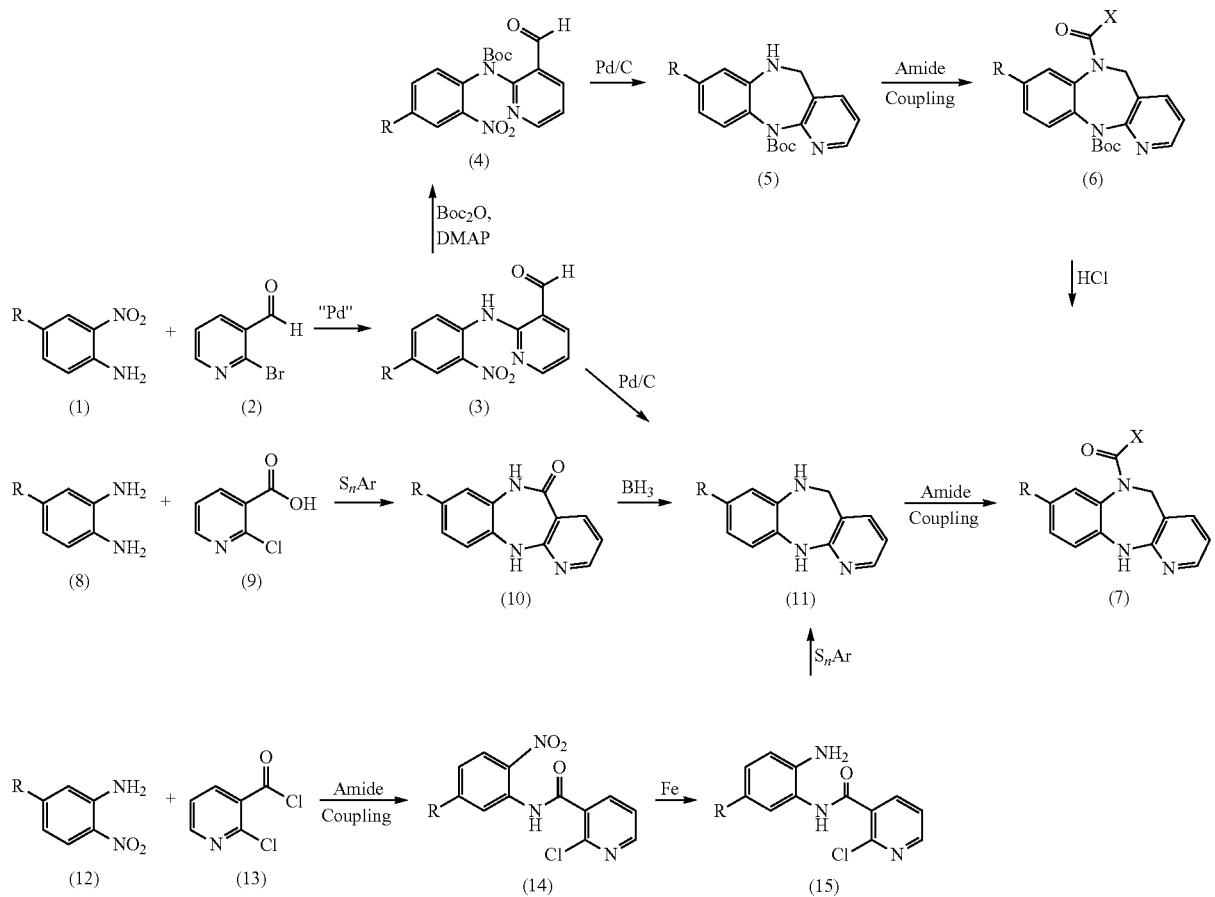

In general scheme 1, compounds of formula (7) can be formed in multiple ways. Substituted nitroaniline (1) and a formyl bromopyridine (2) can be combined in a palladium-mediated C—N coupling reaction to afford (3). Formation of a carbamate followed by reduction of the nitro group with palladium on carbon affords the substituted tricyclic compound (5). Amide coupling followed by deprotection affords the desired tricycle (7). Alternatively a substituted diaminophenyl compound (12) can be reacted via an SnAr reaction with a substituted nicotinic acid (9) to afford the tricyclic compound (10). Borane reduction followed by amide coupling affords the desired tricycle (7). Alternatively, substituted nitroaniline (12) and acyl chloride (13) can be reacted via an amide coupling to afford (14). Reduction of the nitrobenzene (14) with iron affords the aniline (15). A one-pot cyclization and reduction with borane affords the desired tricyclic compound (11) that can undergo an amide coupling to afford (7).

Scheme 2

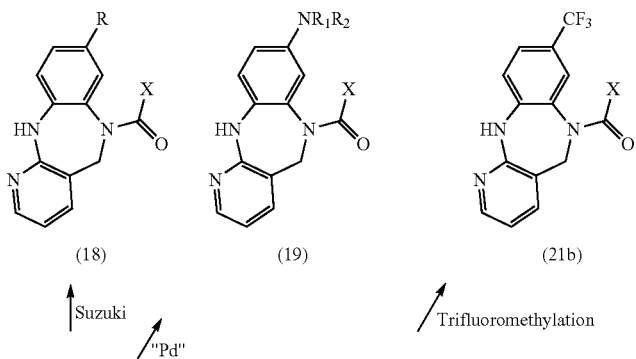

-continued

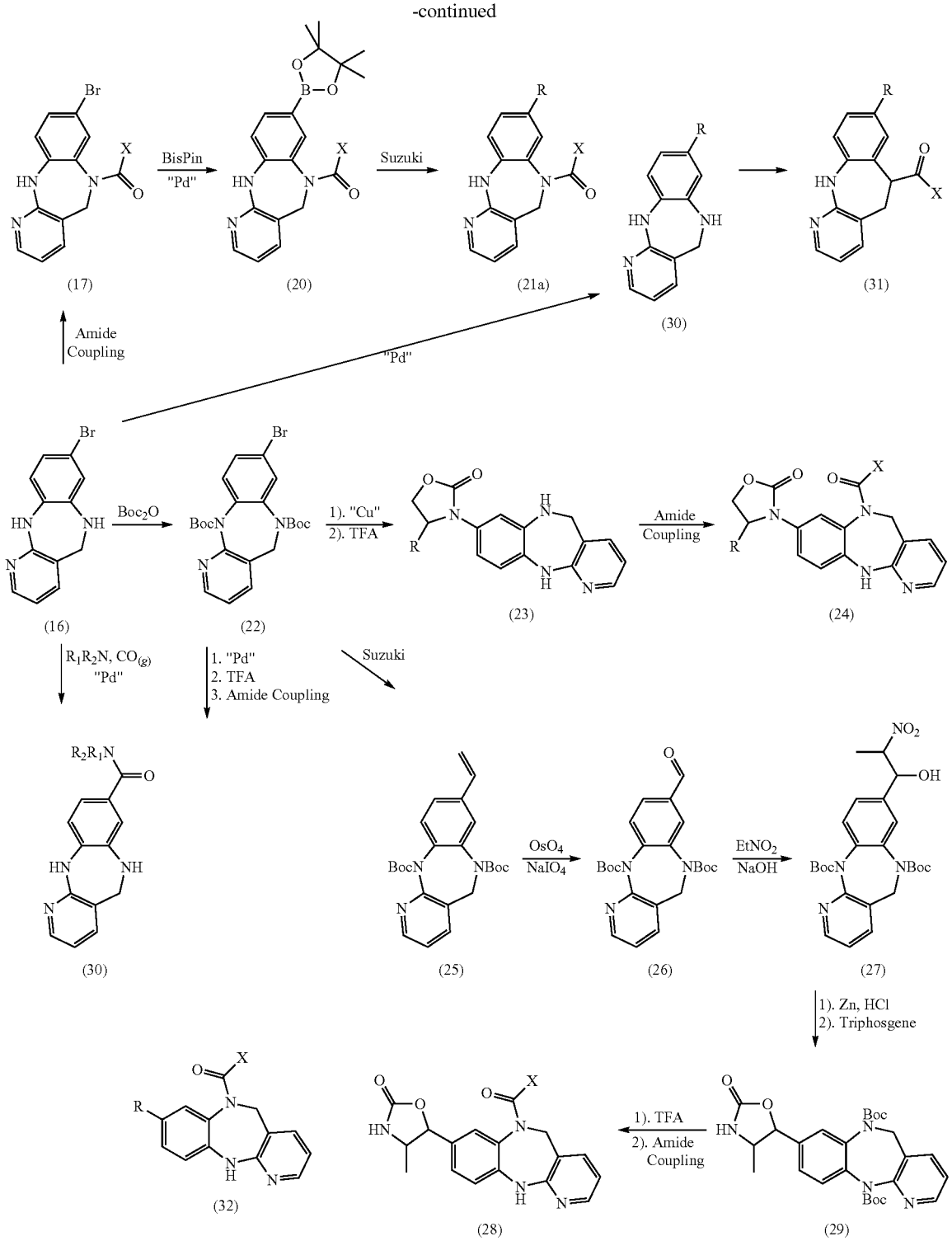

In general scheme 2, compound (16) can be used in a multitude of reactions. Amide coupling with (16) affords the tricycle (17). Suzuki reaction affords the final product (18). Alternatively, a palladium-mediated C—N coupling reaction between (17) and the appropriate amine affords (19). The aryl bromide can be converted to the boronate ester to afford (20). Suzuki reaction affords the final product (21a), or trifluoromethylation affords product (21b). Alternatively, a palladium-mediated C—N coupling reaction with compound (16) affords the C8 functionalized product (30), and amide coupling affords the final product (31). Alternatively, compound (16) can be protected to afford the bis-Boc protected tricycle (22). Ullmann coupling followed by deprotection affords (23). Amide coupling affords the final product (24). Alternatively, the bis-Boc protected tricycle (22) can be converted to the styrene (25). Dihydroxylation followed by oxidative cleavage with sodium periodate affords the aldehyde (26). 1,2-Addition with nitroethane affords the nitro alcohol (27). Reduction of the nitro group with zinc followed by cyclization in the presence of triphosgene affords the oxazolidinone (28). Deprotection followed by an amide coupling affords the final product (29). Alternatively, the bis-boc protected tricycle (22) can undergo a palladium-mediated CN coupling, followed by TFA deprotection and amide coupling to afford (32).

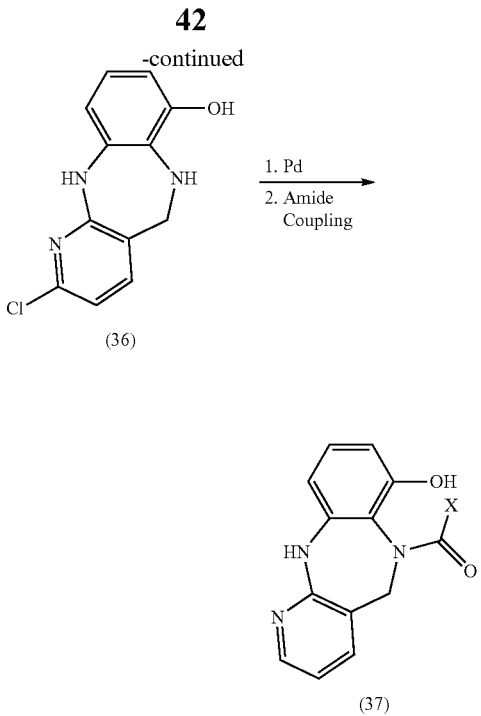

In general scheme 3, compounds of formula (37) can be prepared in the following sequence. A one-pot $S_NAr$/amide coupling with a substituted phenyl diamine (33) and an aldehyde affords the tricycle (35). Reduction with borane affords tricycle (36). Dehalogenation followed by an amide coupling affords the final compound (37).

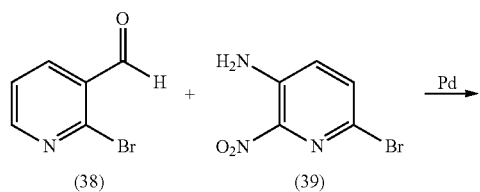

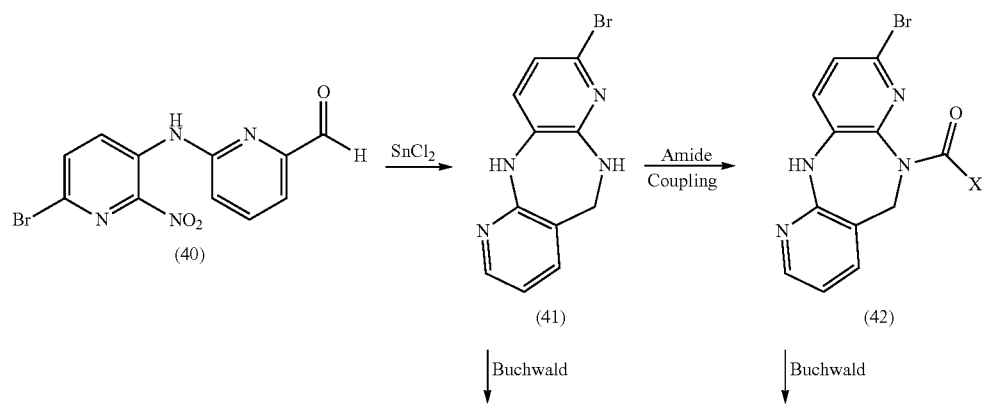

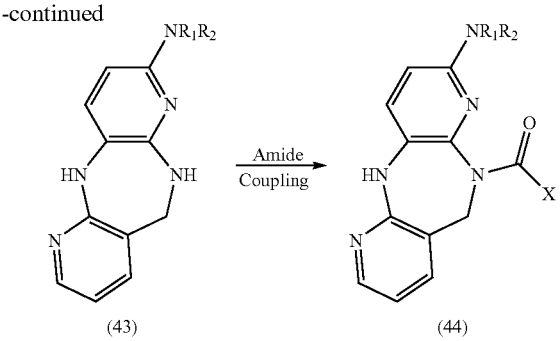

(43) (44)

In general scheme 4, compounds of formula (44) can be prepared in the following sequence. A palladium-mediated C—N coupling between bromopyridine (38) and substituted aminopyridine (39) affords (40). Reduction with SnCl$_2$ and cyclization yields (41). Final product (44) can be prepared from (41) by utilizing a two step sequence, a palladium-mediated C—N coupling reaction and an amide coupling, in either order.

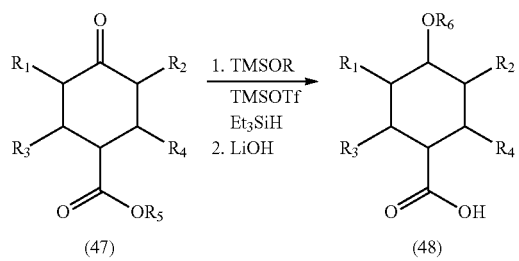

(47) (48)

Scheme 5

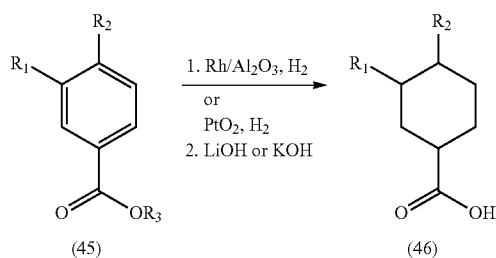

(45) (46)

In general scheme 5, compounds of formula (46) can be prepared via reduction under hydrogen pressure followed by saponification with (45). Reductive coupling of (47) followed by saponification with lithium hydroxide affords the carboxylic acid (48).

Scheme 6

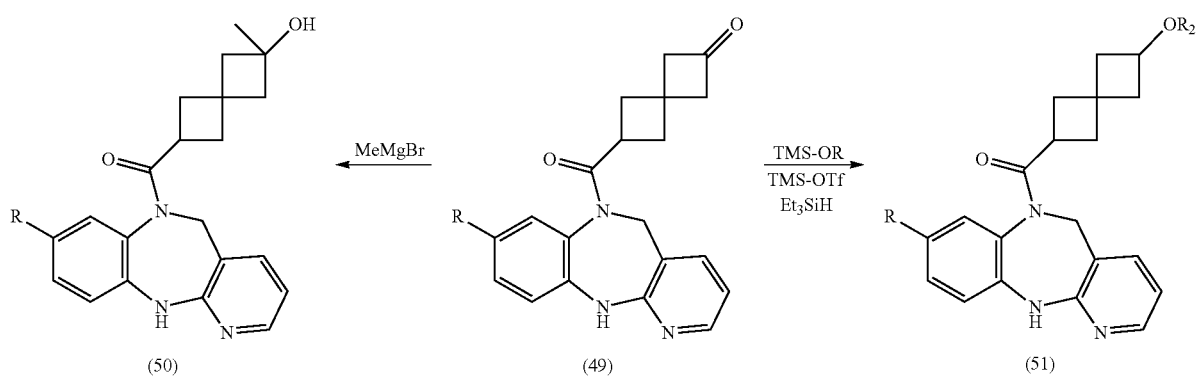

(50) (49) (51)

In general scheme 6, compounds of formula (49) can be used to prepare multiple compounds. Grignard reaction with (49) affords the substituted alcohol (50). Alternatively, reductive coupling of (49) affords the ether (51).

Scheme 7

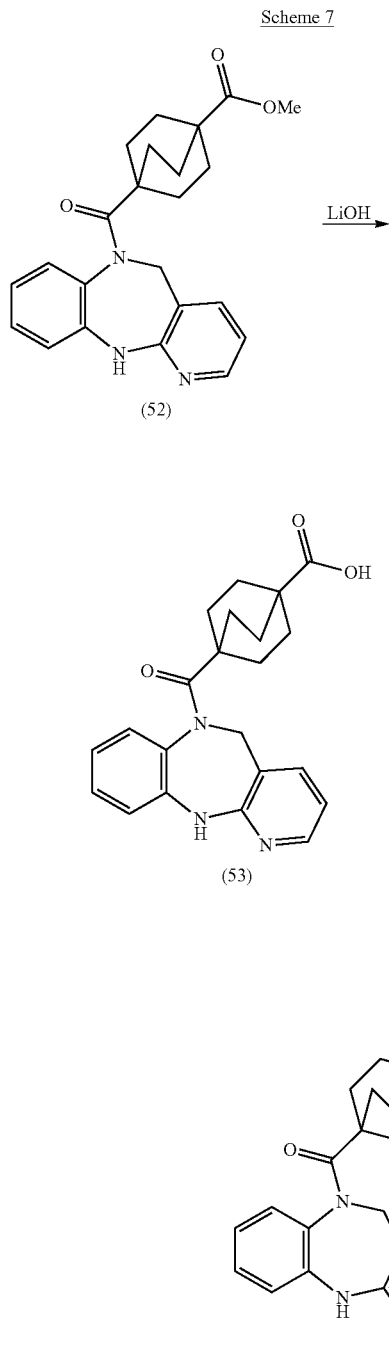

In general scheme 7, oxadiazole (54) can be prepared via a two step sequence starting with the ester (52). Saponification affords the carboxylic acid (53). Amide coupling and cyclization affords the oxadiazole (54).

Scheme 8

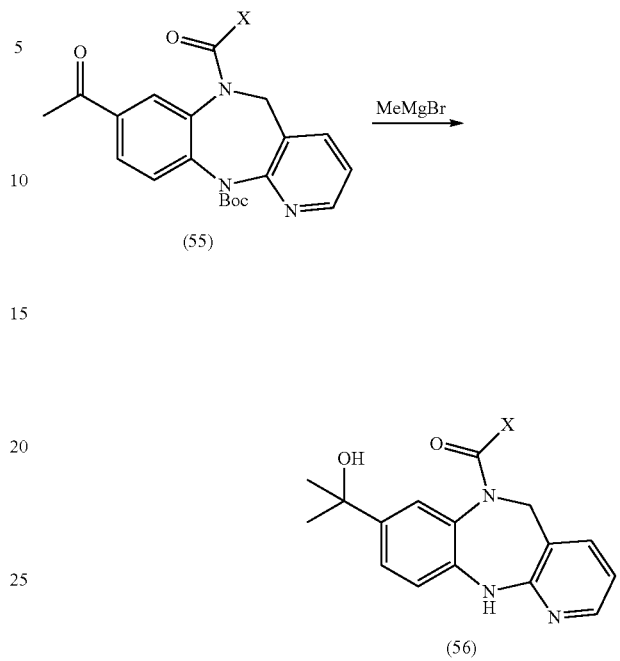

In general scheme 8, Grignard reaction with ketone (55) affords the tertiary alcohol (56).

Scheme 9

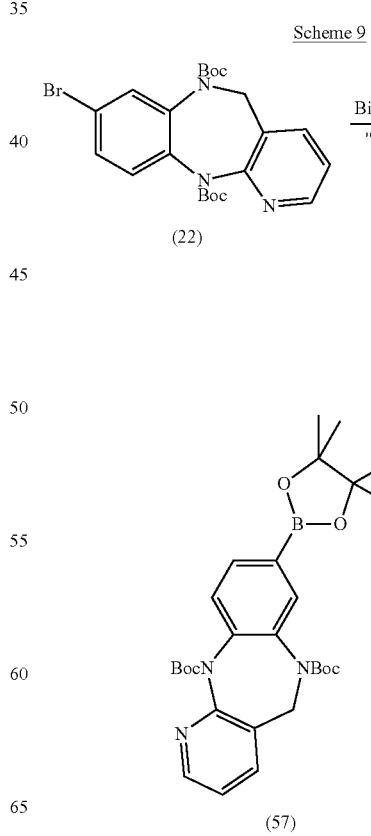

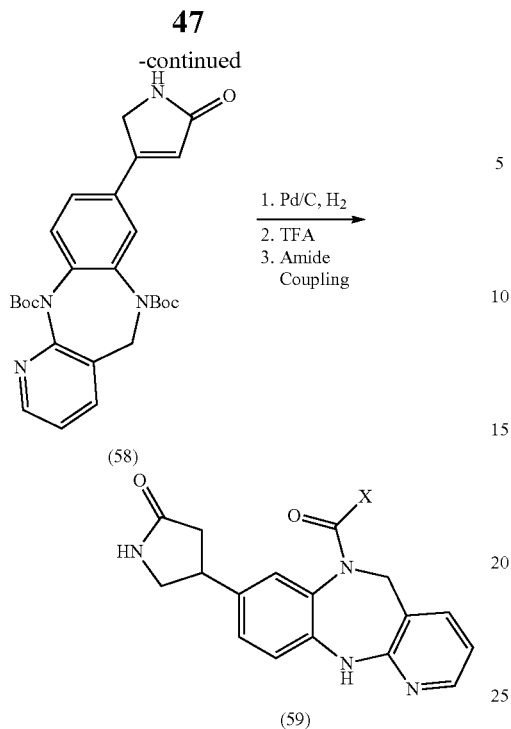

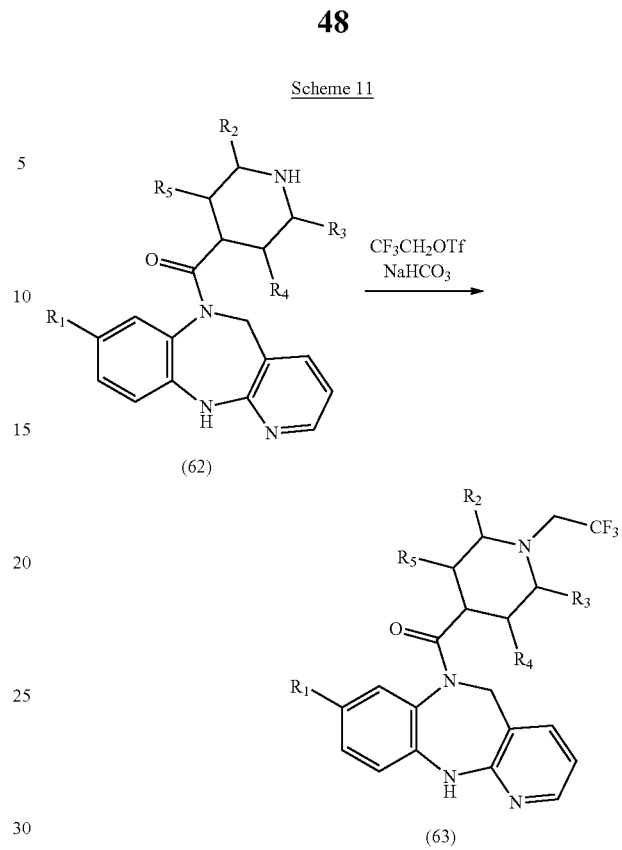

In general scheme 9, compounds of formula (59) can be prepared via the following sequence. Conversion of the aryl bromide (22) with bis(pinacolato)diboron affords the boronate ester (57). Suzuki reaction affords (58). Hydrogenation, acidic deprotection of the protecting group and then amide coupling affords the final product (59).

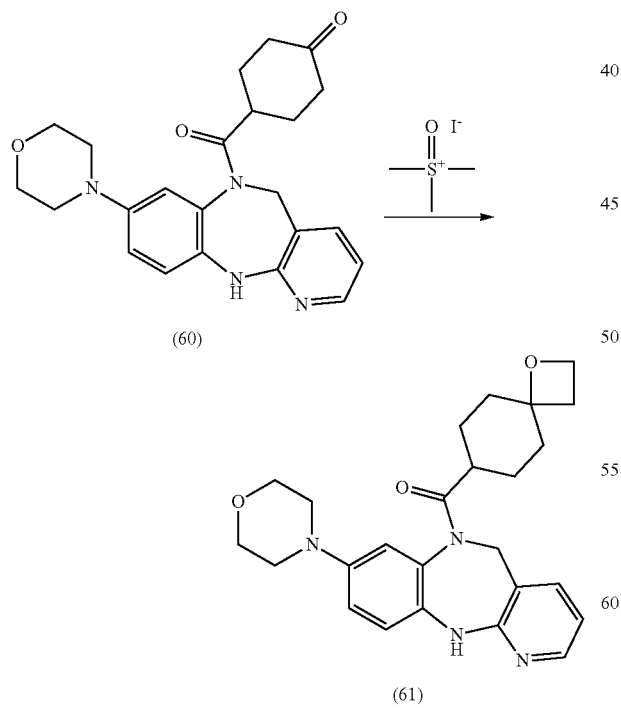

In general scheme 10, ketone (60) can be reacted with trimethylsulfoxonium iodide to afford the oxetane (61).

In general scheme 11, compounds with general structure (63) can be prepared via alkylation of substituted piperidine derivative (62) with 2,2,2-trifluoroethyl trifluoromethanesulfonate.

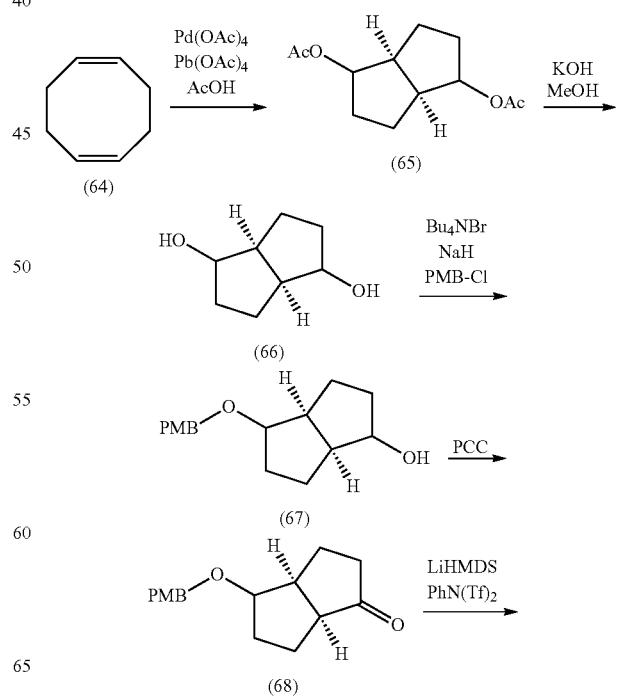

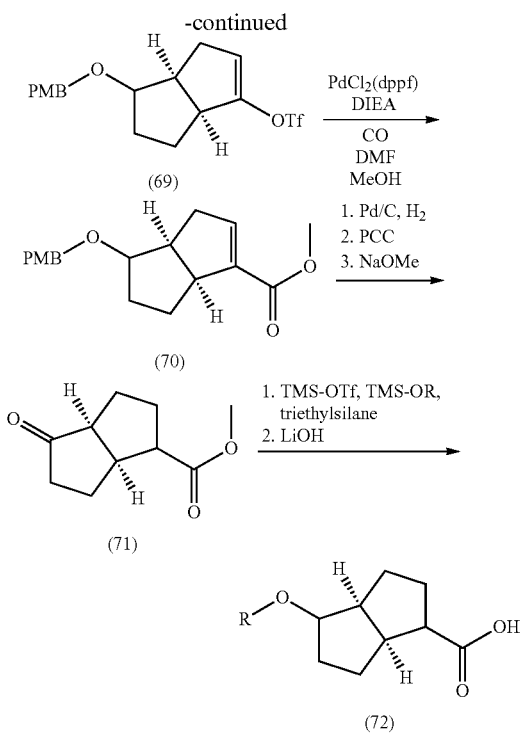

In general scheme 12, compound (72) can be prepared via the following sequence. Intramolecular cyclization of 1,5-cyclooctadiene (64) affords the diacetylated bicyclo[3.3.0] octane (65), followed by hydrolysis to afford diol (66). Mono PMB-protection affords (67), followed by oxidation gives ketone (68). Reaction with base and phenyl triflamide affords vinyl triflate (69), and carbonylation affords ester (70). Hydrogenation followed by oxidation and epimerization afford (71), and reductive coupling and hydrolysis afford carboxylic acid (72).

INTERMEDIATES

Intermediate 1

6,11-Dihydro-5H-benzo[b]pyrido[2,3-e][1,4]diazepine

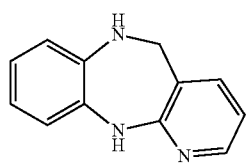 [SMILES: c1cnc2c(c1)CNc1ccccc1N2]

Step 1: To a 10-L 4-necked round-bottom flask purged and maintained with an inert atmosphere of nitrogen was added a mixture of benzene-1,2-diamine (520 g, 4.81 mol) in cyclohexanol (4.8 L) followed by 4-chloropyridine-3-carboxylic acid (760 g, 4.82 mol). The resulting mixture was heated to 150° C. for 2.5 h. Upon cooling to room temperature, the mixture was diluted with DCM (10 L). The resulting solid was collected by filtration and washed with DCM (4×300 mL) to afford 6,11-dihydro-5H-benzo[b]pyrido[2,3-e][1,4]diazepin-5-one as the HCl salt that was taken on to the next step without further characterization or purification.

Step 2: To a 10-L 4-necked round-bottom flask purged and maintained with an inert atmosphere of nitrogen was added a mixture of the HCl salt of 6,11-dihydro-5H-benzo[b]pyrido[2,3-e][1,4]diazepin-5-one (500 g, 2.02 mol) in 1,4-dioxane (4.6 L) followed by the dropwise addition of BH$_3$—SMe$_2$ (10M, 710 mL, 3.50 equiv). The resulting mixture was stirred at room temperature for 10 h. The reaction was then quenched by the addition of aqueous HCl (2 M, 2.0 L) and MTBE (800 mL), and then stirred at room temperature for an additional 10 hours. The pH value of the solution was adjusted to 9-10 with aqueous sodium hydroxide (aq. 50%). The resulting mixture was extracted with ethyl acetate (3×1.5 L). The combined organic layers were washed with brine (1 L), dried over anhydrous magnesium sulfate, filtered and concentrated under reduced pressure. The crude product was purified by re-crystallization from ether to afford 6,11-dihydro-5H-benzo[b]pyrido[2,3-e][1,4] diazepine as a solid. MS: 198 (M+1). $^1$H NMR (300 MHz, CDCl$_3$) δ 8.06-8.04 (m, 1H), 7.26-7.20 (m, 2H), 6.87-6.70 (m, 4H), 6.65-6.61 (m, 1H), 4.18 (m, 3H).

Intermediate 2

8-Bromo-6,11-dihydro-5H-benzo[b]pyrido[2,3-e][1,4]diazepine (HCl salt)

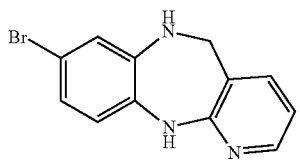 [SMILES: Brc1ccc2c(c1)NCc1cccnc1N2]

Step 1: To a 20-L round-bottom flask was added potassium tert-butoxide (2198 g, 19.54 mol), ethylene glycol dimethyl ether (6 L) and cuprous chloride (45.5 g, 0.460 mol). A mixture of 1-bromo-4-nitrobenzene (929 g, 4.62 mol) and methoxylamine hydrochloride (480 g, 5.75 mol) in N,N-dimethylformamide (7.5 L) was added dropwise over 60 min. The resulting mixture was stirred at room temperature for 12 h and then diluted with ethyl acetate (4 L). The organic phase was washed with aq. NH$_4$Cl (2×12 L) and brine (3×8 L), dried over anhydrous magnesium sulfate, filtered and concentrated under reduced pressure. The solid was washed with petroleum ether (3 L) to afford 5-bromo-2-nitroaniline as a solid that was used in the next reaction without further purification or characterization.

Step 2: To a 20-L 4-necked round-bottom flask was added 5-bromo-2-nitroaniline (792 g, 3.65 mol), 1,4-dioxane (3 L), cyclohexane (9 L) and pyridine (289 g, 3.65 mol) followed by the dropwise addition of a mixture of 2-chloropyridine-3-carbonyl chloride (738 g, 4.20 mol) in 1,4-dioxane (1 L). The resulting mixture was heated to 85° C. for 12 h. Upon cooling to room temperature, the solid was filtered out. The filtrate was extracted with ethyl acetate (3×5 L). The combined organic layers were dried over anhydrous sodium sulfate, filtered and concentrated under reduced pressure. The solid was washed with petroleum ether (2 L) to afford N-(5-bromo-2-nitrophenyl)-2-chloropyridine-3-carboxamide as a red solid that was used in the next reaction without further purification or characterization.

Step 3: To a 20-L 4-necked round-bottom flask was added N-(5-bromo-2-nitrophenyl)-2-chloropyridine-3-carboxamide (800 g, 2.24 mol), ethanol/H$_2$O (1:1 mixture, 10 L) and ammonium chloride (597 g, 11.3 mol) followed by the addition of Fe (629 g, 11.3 mol) in portions. The resulting mixture was heated to 80° C. for 1.5 h. Upon cooling to room temperature, the solid was filtered out. The filtrate was concentrated under reduced pressure. The residual mixture was extracted with ethyl acetate/tetrahydrofuran (1:3 mixture, 2×5 L). The combined organic layers were washed with brine (3 L), dried over anhydrous sodium sulfate, filtered and concentrated under reduced pressure to afford N-(2-amino-5-bromophenyl)-2-chloropyridine-3-carboxamide as a solid that was used in the next reaction without further purification or characterization.

Step 4: To a 20-L 4-necked round-bottom flask was added N-(2-amino-5-bromophenyl)-2-chloropyridine-3-carboxamide (330 g, 1.01 mol), tetrahydrofuran (5 L) and $BH_3$/THF (1M, 4.55 L, 4.55 mol). The resulting mixture was heated to 60° C. for 2 h. The reaction was then quenched by the addition of methanol (6.8 L) and heated to 70° C. for 2 h. Upon cooling to room temperature, the mixture concentrated under reduced pressure. The residue was taken up in MTBE (800 mL) and the mixture was acidified to a pH ~2 with aqueous HCl (2N). The pH was then adjusted to pH ~8-10 with aq. NaOH (2M). The resulting mixture was extracted with ethyl acetate/THF(1:3 mixture, 2×3 L). The combined organic layers were washed with brine (1×2 L), dried over anhydrous sodium sulfate, filtered and concentrated under reduced pressure. The resulting solid was washed with $H_2O$ (5×1 L) to afford 5-bromo-1-N-[(2-chloropyridin-3-yl)methyl]benzene-1,2-diamine as a solid that was used in the next reaction without further purification or characterization.

Step 5: To a 10-L 4-necked round-bottom flask was added 5-bromo-1-N-[(2-chloropyridin-3-yl)methyl]benzene-1,2-diamine (465 g, 1.49 mol) and cyclohexanol (4.5 L). The resulting mixture was heated to 140° C. for 3 h. Upon cooling to room temperature, the mixture was concentrated under reduced pressure. The crude product was re-crystallized from dichloromethane and then washed with diethyl ether (2 L) to afford 8-bromo-6,11-dihydro-5H-benzo[b]pyrido[2,3-e][1,4]diazepine (HCl salt) as a solid. MS 276 (M+1). $^1$H NMR (300 MHz, DMSO-$d_6$) δ 10.75 (s, 1H), 8.16-8.13 (q, 1H), 7.88-7.82 (t, 1H), 7.15-6.70 (m, 4H), 4.20-4.16 (d, 2H).

Intermediate 3

4-(6,11-Dihydro-5H-benzo[b]pyrido[2,3-e][1,4]diazepin-8-yl)morpholine

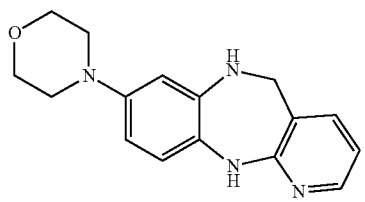 [SMILES: c1cnc2c(c1)CNc1cc(N3CCOCC3)ccc1N2]

Step 1: To a 5000-mL 3-necked round-bottom flask purged and maintained with an inert atmosphere of nitrogen was added 4-(morpholin-4-yl)-2-nitroaniline (65.0 g, 291 mmol), 2-bromopyridine-3-carbaldehyde (53.8 g, 289 mmol), tert-Butanol (3000 mL), sodium carbonate (43.2 g, 408 mmol), $Pd_2(dba)_3$ (30.1 g, 32.9 mmol) and xantphos (33.6 g, 58.1 mmol). The resulting mixture was heated to 80° C. for 18 h. Upon cooling to room temperature, the mixture was concentrated under reduced pressure. The residue was washed with ether (2×300 mL) and then purified by column chromatography on silica gel (dichloromethane/methanol, 100:1 mixture) to afford 2-[[4-(morpholin-4-yl)-2-nitrophenyl]amino]pyridine-3-carbaldehyde.

Step 2: To a 2000-mL round-bottom flask, was added 2-[[4-(morpholin-4-yl)-2-nitrophenyl]amino]pyridine-3-carbaldehyde (75.0 g, 228 mmol), methanol (900 mL), THF (300 mL) and palladium on carbon (10 wt % loading, 7.5 g, 7.1 mmol). The mixture was evacuated and then purged with hydrogen multiple times. The resulting mixture was stirred overnight at room temperature. The solids were then filtered out and the filtrate was concentrated under reduced pressure. The residue was purified by column chromatography on silica gel (dichloromethane/methanol, 100:1) to afford 4-(6,11-dihydro-5H-benzo[b]pyrido[2,3-e][1,4]diazepin-8-yl)morpholine as a solid. MS 283 (M+1). $^1$H NMR (300 MHz, DMSO-$d_6$) δ 8.46 (s, 1H), 7.30 (d, 1H), 7.27 (d, 1H), 6.95 (d, 1H), 6.52 (s, 1H), 6.35 (m, 2H), 5.63 (s, 1H), 3.97 (m, 2H), 3.70 (m, 4H), 2.94 (m, 4H).

Intermediate 4

Tert-butyl 8-morpholino-5H-benzo[b]pyrido[2,3-e][1,4]diazepine-11(6H)-carboxylate

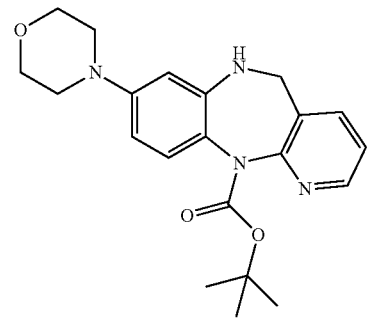 [SMILES: CC(C)(C)OC(=O)N1c2ccc(N3CCOCC3)cc2NCc2cccnc21]

Step 1: A mixture of 1-Fluoro-3-nitrobenzene (3.0 g, 21 mmol) in morpholine (12.0 mL, 138 mmol) was heated to 140° C. for 48 h. Upon cooling to room temperature, the mixture was concentrated under reduced pressure and purified by column chromatography on silica gel (hexanes/ethyl acetate, 0-100%) to afford 4-(3-Nitrophenyl)morpholine.

Step 2: A mixture of 4-(3-Nitrophenyl)morpholine (3.4 g, 16 mmol) and N-bromosuccinimide, (3.2 g, 18 mmol) in DMF (24 mL) was stirred for 30 minutes at room temperature. The mixture was then diluted with saturated aqueous sodium sulfite (40 mL) and then stirred for 30 minutes. The mixture was then filtered and the solids were washed with water (2×10 mL) to afford 4-(4-Bromo-3-nitrophenyl)morpholine that was used in the next reaction without further purification or characterization.

Step 3: To a mixture of 2-Aminonicotinaldehyde (2.5 g, 21 mmol), 4-(4-Bromo-3-nitrophenyl)morpholine, (6.47 g, 22.5 mmol), $Pd_2(dba)_3$, (0.937g, 1.02 mmol), xanthphos (1.30 g, 2.25 mmol) and cesium carbonate (10 g, 30 mmol) was added THF (20 mL) and the mixture was degassed via subsurface bubbling with nitrogen for 10 minutes. The mixture was heated to reflux for 18h. Upon cooling to room temperature, $Boc_2O$ (5.81 g, 26.6 mmol) and DMAP (2.5 g, 20.5 mmol) were added and the mixture was stirred at room temperature for 2 h. The mixture was then diluted with dichloromethane (10 mL) and filtered through celite. The filtrate was absorbed on to silica gel and purified by column chromatography on silica gel (hexanes/ethyl acetate, 0-100%) to afford tert-butyl (3-formylpyridin-2-yl)(4-morpholino-2-nitrophenyl)carbamate.

Step 4: To tert-butyl (3-formylpyridin-2-yl)(4-morpholino-2-nitrophenyl)carbamate (2.7 g, 6.3 mmol) in methanol (27 mL) and ethyl acetate (14 mL) was added Pd/C, (10% by weight, 0.67 g, 0.63 mmol). The mixture was fitted with a hydrogen balloon and the mixture was evacuated and then purged with hydrogen multiple times and the mixture was stirred overnight at room temperature. The mixture was diluted with DCM and filtered through a pad of celite. The filtrate was absorbed on silica gel and purified by column chromatography on silica gel (0 to 100% EtOAc/Hex) to afford tert-butyl 8-morpholino-5H-benzo[b]pyrido[2,3-e][1,4]diazepine-11(6H)-carboxylate as a solid. MS: 383 (M+1). $^1$H NMR (499 MHz, CDCl$_3$) δ 8.47 (dd, J=4.9, 1.6, 1H), 7.65 (dd, J=7.5, 1.7, 1H), 7.33-7.20 (m, 3H), 6.35 (dd, J=8.8, 2.6, 1H), 5.99 (d, J=2.6, 1H), 4.14 (s, 1H), 3.90-3.74 (m, 4H), 3.10-2.97 (m, 4H), 1.43 (s, 9H).

Intermediate 5

Tert-butyl 8-morpholino-6-(6-oxospiro[3.3]heptane-2-carbonyl)-5H-benzo[b]pyrido[2,3-e][1,4]diazepine-11(6H)-carboxylate

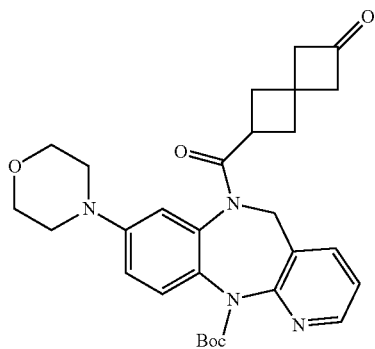 [SMILES: CC(C)(C)OC(=O)N1c2ccc(N3CCOCC3)cc2N(C(=O)C2CC3(CC(=O)C3)C2)Cc2cccnc21]

To a mixture of 6-oxospiro[3.3]heptane-2-carboxylic acid (0.089 g, 0.58 mmol) in DCM (1 mL) in a vial was added 1-chloro-N,N,2-trimethylpropenylamine (0.083 mL, 0.63 mmol) and the mixture was allowed to stir for 35 minutes. To a second vial was added tert-butyl 8-morpholino-5H-benzo[b]pyrido[2,3-e][1,4]diazepine-11(6H)-carboxylate (0.20 g, 0.52 mmol), DCM (4 mL) and DIEA (0.365 mL, 2.09 mmol) and the mixture was allowed to stir for 2 minutes. The mixture in vial 1 was added dropwise to the mixture in vial 2 and the mixture was allowed to stir at room temperature for one hour. The mixture was then concentrated under reduced pressure and the material was purified by column chromatography on silica gel (40-100% EtOAc/Hex) to afford tert-butyl 8-morpholino-6-(6-oxospiro[3.3]heptane-2-carbonyl)-5H-benzo[b]pyrido[2,3-e][1,4]diazepine-11(6H)-carboxylate. MS: 519 (M+1).

Intermediate 6

2-(6,11-Dihydro-5H-benzo[b]pyrido[2,3-e][1,4]diazepin-8-yl)-2-methylpropanenitrile

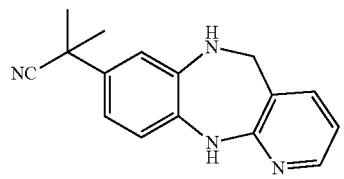 [SMILES: CC(C)(C#N)c1ccc2c(c1)NCc1cccnc1N2]

Step 1: To a mixture of N-(4-(2-cyanopropan-2-yl)phenyl)acetamide (124 g, 0.614 mol) in conc. H$_2$SO$_4$ (494 mL) at −10° C. was added HNO$_3$ (10 M, 73 mL, 0.73 mol) dropwise. The mixture was stirred at −5° C. for 20 min. The mixture was then poured into ice-water (2 L) and extracted with MTBE (4×2 L). The combined organic layers were washed with sat. potassium carbonate, brine, dried over sodium sulfate, filtered and concentrated under reduced pressure to afford crude N-(4-(2-cyanopropan-2-yl)-2-nitrophenyl)acetamide as a solid that was used in the next reaction without further purification or characterization.

Step 2: To a mixture of crude N-(4-(2-cyanopropan-2-yl)-2-nitrophenyl)acetamide (250 g, 1.01 mol) in methanol (2.5 L) at 0° C. was added sodium hydroxide (243 g, 6.06 mol) and the mixture was warmed to room temperature overnight. The mixture was concentrated and the residue was poured into water (1500 mL) and extracted with ethyl acetate (2×2 L). The combined organic layers were dried over sodium sulfate, filtered and concentrated under reduced pressure. The residue was purified by column chromatography on silica gel (petroleum ether/ethyl acetate, 10/1 to 1/1) to afford 2-(4-amino-3-nitrophenyl)-2-methylpropanenitrile as a solid.

Step 3: To a mixture of 2-(4-amino-3-nitrophenyl)-2-methylpropanenitrile (100 g, 0.487 mol), 2-chloronicotinaldehyde (138 g, 0.975 mol) and Cs$_2$CO$_3$ (397 g, 1.22 mol) in 1,4-dioxane (1.5 L) was added Pd$_2$(dba)$_3$ (45 g, 0.049 mol) and Xantphos (28 g, 0.049 mol) under N$_2$. The mixture was heated to reflux for 2 h. Upon cooling to room temperature, the mixture was diluted with H$_2$O (1 L) and extracted with ethyl acetate (3×1 L). The combined organic layers were dried over sodium sulfate, filtered and concentrated under reduced pressure. The residue was purified by column chromatography on silica gel (petroleum ether/ethyl acetate, 100/1 to 1/5) to afford 2-(4-((3-formylpyridin-2-yl)amino)-3-nitrophenyl)-2-methylpropanenitrile as a solid.

Step 4: To a mixture of 2-(4-((3-formylpyridin-2-yl)amino)-3-nitrophenyl)-2-methylpropanenitrile (25 g, 81 mmol) in ethyl acetate (1.0 L) and ethanol (1.0 L) was added palladium on carbon (10 wt % loading, 7.5 g, 7.1 mmol). The flask was fitted with a hydrogen balloon and the mixture was evacuated and then purged multiple times with hydrogen. The mixture was stirred under a H$_2$ balloon at room temperature for 30 h. The mixture was then filtered and the filtrate was concentrated and the residue was purified by column chromatography on silica gel (petroleum ether/ethyl acetate, 10/1 to 3/1) to afford 2-(6,11-dihydro-5H-benzo[b]pyrido[2,3-e][1,4]diazepin-8-yl)-2-methylpropanenitrile as a solid. MS: 265 (M+1). $^1$H NMR (400 MHz, CDCl$_3$) δ 8.08 (dd, J=4.8 Hz, 1H), 7.27 (s, 1H), 7.19 (s, 1H), 6.88 (m, 2H), 6.85 (d, J=3.6 Hz, 1H), 6.79 (d, J=8.0 Hz, 1H), 4.27 (s, 1H), 4.20 (s, 2H), 1.71 (s, 6H).

Intermediate 7

(R)-3-(6,11-Dihydro-5H-benzo[b]pyrido[2,3-e][1,4]diazepin-8-yl)-4-iso propyloxazolidin-2-one

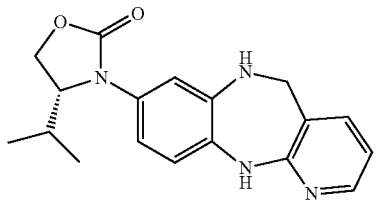 [SMILES: CC(C)[C@@H]1COC(=O)N1c1ccc2c(c1)NCc1cccnc1N2]

Step 1: To a mixture of di-tert-butyl 8-bromo-5H-benzo[b]pyrido[2,3-e][1,4]diazepine-6,11-dicarboxylate (500 mg, 1.05 mmol), (R)-4-isopropyloxazolidin-2-one (271 mg, 2.10 mmol), copper(I) iodide (40 mg, 0.21 mmol), N,N'-dimethyl-1,2-cyclohexanediamine (60 mg, 0.42 mmol) and potassium phosphate tribasic (446 mg, 2.10 mmol) was added dioxane (4 mL). The microwave vial was sealed and placed under a nitrogen atmosphere by performing 6 vacuum/nitrogen cycles. The mixture was heated 120° C. for 2 hours in a microwave reactor. Upon cooling to room temperature, the solvent was removed under reduced pressure. The residue was purified by column chromatography on silica gel (0-100% EtOAc/hexanes) to afford (R)-di-tert-butyl 8-(4-isopropyl-2-oxooxazolidin-3-yl)-5H-benzo[b]pyrido[2,3-e][1,4]diazepine-6,11-dicarboxylate.

Step 2: To a mixture of (R)-di-tert-butyl 8-(4-isopropyl-2-oxooxazolidin-3-yl)-5H-benzo[b]pyrido[2,3-e][1,4]diazepine-6,11-dicarboxylate (0.35 g, 0.67 mmol) in dichloromethane (1 mL) was added trifluoroacetic acid (1 mL) and the mixture was stirred at room temperature for 1 h. The solvent was removed under reduced pressure to afford (R)-3-(6,11-dihydro-5H-benzo[b]pyrido[2,3-e][1,4]diazepin-8-yl)-4-isopropyloxazolidin-2-one as TFA salt. MS: 325 (M+1).

Intermediate 8

1,3-Dihydro-2H-isoindol-2-yl(6,11-dihydro-5H-pyrido[2,3-b][1,5]benzodiazepin-8-yl)methanone

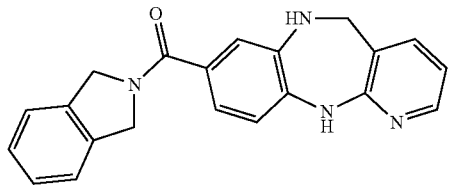 [SMILES: O=C(c1ccc2c(c1)NCc1cccnc1N2)N1Cc2ccccc2C1]

A vial was charged with 2,3-dihydro-1H-isoindole (173 mg, 1.45 mmol), 8-bromo-6,11-dihydro-5H-pyrido[2,3-b][1,5]benzodiazepine (200 mg, 0.724 mmol), sodium carbonate (384 mg, 3.62 mmol), palladium (II) acetate (16 mg, 0.072 mmol), (9,9-dimethyl-9H-xanthene-4,5-diyl)bis(diphenylphosphane) (63 mg, 0.11 mmol), and dioxane (2.0 mL). The vial was sealed and connected through a needle to a balloon charged with carbon monoxide (g). The reaction mixture, under an atmosphere of carbon dioxide was heated to 90° C. for 18 hours. Upon cooling to room temperature, the mixture was diluted with DMSO, filtered, and purified by mass triggered reverse phase HPLC (ACN/water with 0.1% TFA modifier) to afford 1,3-dihydro-2H-isoindol-2-yl (6, 11-dihydro-5H-pyrido[2,3-b][1,5]benzodiazepin-8-yl)methanone as the TFA salt. MS: 343 (M+1). $^1$H NMR (600 MHz, CD$_3$OD) δ 8.01 (dd, J=6.0, 1.2 Hz, 1H), 7.78 (d, J=7.2 Hz, 1H), 7.35 (d, J=7.8 Hz, 1H), 7.30-7.25 (m, 2H), 7.22 (d, J=7.2 Hz, 1H), 7.17-7.14 (m, 3H), 6.96 (t, J=6.6 Hz, 1H), 4.93 (s, 2H), 4.87 (s, 2H), 4.25 (s, 2H).

Intermediate 9

(8-Bromo-5,11-dihydro-6H-pyrido[2,3-b][1,5]benzodiazepin-6-yl)(6,7,8,9-tetrahydro-5H-benzo[7]annulen-7-yl)methanone

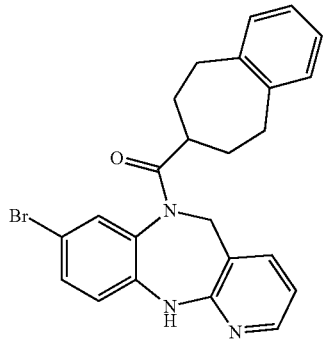 [SMILES: O=C(C1CCc2ccccc2CC1)N1Cc2cccnc2Nc2ccc(Br)cc21]

To a vial was added 6,7,8,9-tetrahydro-5H-benzo[7]annulene-7-carboxylic acid (254 mg, 1.33 mmol), 8-bromo-6,11-dihydro-5H-benzo[b]pyrido[2,3-e][1,4]diazepine HCl salt (500 mg, 1.60 mmol), trichloroacetonitrile (0.668 mL, 6.66 mmol), polymer supported triphenylphosphine (1.94 mmol/g loading, 2.06 g, 4.00 mmol), and acetonitrile (13.3 mL). The vial was sealed and heated to 150° C. for 15 minutes in a microwave reactor. Upon cooling to room temperature, the mixture was diluted with methanol (20 mL), filtered and the solids were washed with methanol (20 mL). The filtrate was concentrated under reduced pressure, and the residue was purified by column chromatography on silica (20-100% 3:1 EtOAc:EtOH/Hexanes) to afford (8-bromo-5,11-dihydro-6H-pyrido[2,3-b][1,5]benzodiazepin-6-yl)(6,7,8,9-tetrahydro-5H-benzo[7]annulen-7-yl)methanone as a solid. MS: 448, 450 (M+1, M+3). $^1$H NMR (600 MHz, DMSO-d$_6$) δ 9.64 (s, 1H), 8.03 (dd, J=4.9, 1.5 Hz, 1H), 7.55 (d, J=2.3 Hz, 1H), 7.47 (d, J=6.6 Hz, 1H), 7.41 (dd, J=8.8, 2.3 Hz, 1H), 7.29 (d, J=8.8 Hz, 1H), 7.04 (d, J=7.1 Hz, 1H), 7.02-6.94 (m, 2H), 6.92 (d, J=7.1 Hz, 1H), 6.72 (dd, J=7.3, 4.9 Hz, 1H), 5.12 (d, J=15.1 Hz, 1H), 3.91 (d, J=14.9 Hz, 1H), 2.79-2.67 (m, 2H), 2.61 (t, J=13.0 Hz, 1H), 2.43 (d, J=6.8 Hz, 1H), 2.40-2.30 (m, 1H), 2.09 (s, 1H), 1.46-1.27 (m, 2H), 0.91 (q, J=11.9 Hz, 1H).

Intermediate 10

6,11-Dihydro-5H-benzo[b]pyrido[2,3-e][1,4]diazepin-7-ol

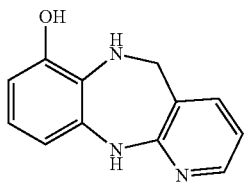 [SMILES: Oc1cccc2c1NCc1cccnc1N2]

Step 1: To a flask was added 2,3-diaminophenol (1.0 g, 8.1 mmol), 2,6-dichloro-nicotinic acid (1.6 g, 8.1 mmol) and 2-butoxyethanol (10 mL) and the mixture was heated to 150° C. for 5 h. Upon cooling to room temperature, the mixture was diluted with ethyl acetate (20 mL), and washed with water (2×). The organic layer was dried over anhydrous sodium sulfate, filtered and concentrated under reduced pressure. The residue was purified by column chromatography on silica gel (petroleum ether/ethyl acetate, 5:1 ratio) to afford 2-chloro-7-hydroxy-6,11-dihydro-5H-benzo[b]pyrido[2,3-e][1,4]diazepin-5-one.

Step 2: To a mixture of 2-chloro-7-hydroxy-6,11-dihydro-5H-benzo[b]pyrido[2,3-e][1,4]diazepin-5-one (85 mg, 0.33 mmol) in THF (10 mL) was added borane tetrahydrofuran complex (1.0 M in THF, 1.0 mL, 1.0 mmol) dropwise. The mixture was then refluxed for 12 h. Upon cooling to room temperature, the mixture was acidified with conc. HCl to pH=1 and the resulting mixture solution was refluxed for 3 h. Upon cooling to room temperature, the mixture was neutralized to pH=8 with saturated aq. sodium bicarbonate and extracted with EtOAc. The organic layer was dried over anhydrous sodium sulfate, filtered, concentrated and purified by column chromatography on silica gel (petroleum ether:ethyl acetate=5:1) to afford 2-chloro-6,11-dihydro-5H-benzo[b]pyrido[2,3-e][1,4]diazepin-7-ol.

Step 3: To a vial containing 2-chloro-6,11-dihydro-5H-benzo[b]pyrido[2,3-e][1,4]diazepin-7-ol (200 mg, 0.807 mmol), tris(dibenzylideneacetone)dipalladium(0) (74 mg, 0.081 mmol), tricyclohexylphosphine (45 mg, 0.16 mmol) and sodium formate (550 mg, 8.07 mmol) was added dioxane (3.3 mL) and water (3.3 mL). The mixture was evacuated and then purged three times with nitrogen. The mixture was heated to 100° C. for 4 hours. Upon cooling to room temperature, the mixture was concentrated under reduced pressure and then purified by HPLC (acetonitrile/water with 0.01% TFA modifier). The fractions containing product were diluted with ethyl acetate and washed with aqueous saturated sodium bicarbonate. The organic layer was then dried over anhydrous magnesium sulfate, filtered and concentrated to afford 6,11-dihydro-5H-benzo[b]pyrido[2,3-e][1,4]diazepin-7-ol. MS 214 (M+1). $^1$H NMR (600 MHz, CD3OD) δ 7.94 (d, J=4.8 Hz, 1H), 7.34 (d, J=7.1 Hz, 1H), 6.65 (t, J=5.5 Hz, 1H), 6.61 (t, J=8.0 Hz, 1H), 6.46 (d, J=8.1 Hz, 1H), 6.33 (d, J=7.8 Hz, 1H), 4.11 (s, 2H).

Intermediate 11

6,7,8,9-Tetrahydro-5H-benzo[7]annulen-7-yl[8-(4,4,5,5-tetramethyl-1,3,2-dioxaborolan-2-yl)-5,11-dihydro-6H-pyrido[2,3-b][1,5]benzodiazepin-6-yl]methanone

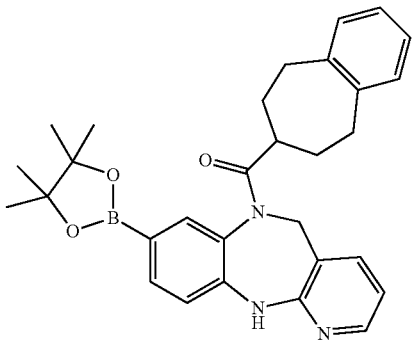 [SMILES: CC1(C)OB(c2ccc3c(c2)N(C(=O)C2CCc4ccccc4CC2)Cc2cccnc2N3)OC1(C)C]

To an oven-dried, nitrogen-cooled vial was added (8-bromo-5,11-dihydro-6H-pyrido[2,3-b][1,5]benzodiazepin-6-yl)(6,7,8,9-tetrahydro-5H-benzo[7]annulen-7-yl) methanone (225 mg, 0.502 mmol), bis(pinacolato)diboron (255 mg, 1.00 mmol), potassium acetate (99 mg, 1.0 mmol), and 1,1'-bis(di-tert-butylphosphino)ferrocene palladium dichloride (33 mg, 0.050 mmol). DMA (2.5 mL) was added, and the mixture was degassed for 10 minutes under a nitrogen atmosphere. The reaction mixture was heated to 90° C. for 16 h. Upon cooling to room temperature, the mixture was filtered through celite. The filtrate was diluted with water, and extracted with EtOAc (3×). The combined organic extracts were washed with brine, dried over sodium sulfate, filtered, and concentrated under reduced pressure. The residue was purified by column chromatography on silica gel (0-100% EtOAc/Hexanes) to afford 6,7,8,9-tetrahydro-5H-benzo[7]annulen-7-yl[8-(4,4,5,5-tetramethyl-1,3,2-dioxaborolan-2-yl)-5,11-dihydro-6H-pyrido[2,3-b][1,5]benzodiazepin-6-yl]methanone as a solid. MS 496 (M+1).

Intermediate 12

(2R)-2,3-Dihydro-1,4-benzodioxin-2-yl[8-(4,4,5,5-tetramethyl-1,3,2-dioxaborolan-2-yl)-5,11-dihydro-6H-pyrido[2,3-b][1,5]benzodiazepin-6-yl]methanone

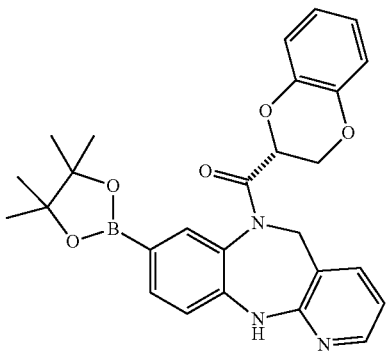

Intermediate 12 was prepared using the procedure described for Intermediate 11. MS: 486 (M+1)

Intermediate 13

Tert-butyl 8-acetyl-5H-benzo[b]pyrido[2,3-e][1,4]diazepine-11(6H)-carboxylate

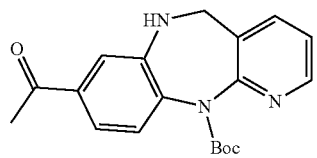 [SMILES: CC(=O)c1ccc2c(c1)NCc1cccnc1N2C(=O)OC(C)(C)C]

Step 1: To a mixture of 2-Aminonicotinaldehyde (1.0 g, 8.2 mmol), 1-(4-bromo-3-nitrophenyl)ethanone (2.2 g, 9.0 mmol), Pd$_2$(dba)$_3$, (0.38 g, 0.41 mmol), xanthphos (0.52 g, 0.11 mmol) and cesium carbonate (4.0 g, 12 mmol) was added THF (8 mL) and the mixture was degassed via subsurface bubbling with nitrogen for 10 minutes. The mixture was heated to reflux for 2 hours. Upon cooling to room temperature the mixture was diluted with dichlormethane and then filtered through celite. The filtrate was concentrated and purified by column chromatography on silica gel to afford 2-((4-acetyl-2-nitrophenyl)amino)nicotinaldehyde.

Step 2: To a mixture of 2-((4-acetyl-2-nitrophenyl)amino)nicotinaldehyde (1.2 g, 4.2 mmol) in THF (2.1 mL) was added di-tert-butyl dicarbonate (1.1 g, 4.8 mmol) and DMAP (0.67 g, 5.5 mmol) and the mixture was stirred for 30 minutes at room temperature. The mixture was then diluted with dichloromethane and absorbed on silica gel. The mixture was purified by column chromatography on silica gel to afford tert-butyl (4-acetyl-2-nitrophenyl)(3-formylpyridin-2-yl)carbamate.

Step 3: To a mixture of tert-butyl (4-acetyl-2-nitrophenyl)(3-formylpyridin-2-yl)carbamate (800 mg, 2.08 mmol) in methanol (8 mL) and ethyl acetate (4 mL) was added Pd/C, (10% by weight, 221 mg, 0.208 mmol). The mixture was fitted with a hydrogen balloon and the mixture was evacuated and then purged with hydrogen multiple times and the mixture was stirred overnight at room temperature. The mixture was diluted with DCM and filtered through a pad of celite. The filtrate was absorbed on silica gel and purified by column chromatography on silica gel (0 to 100% EtOAc/Hex) to afford tert-butyl 8-acetyl-5H-benzo[b]pyrido[2,3-e][1,4]diazepine-11(6H)-carboxylate that was ~80% pure. The impure product was used without further purification. MS: 340 (M+1).

Intermediate 14

Tert-butyl 8-acetyl-6-(6,7,8,9-tetrahydro-5H-benzo[7]annulene-7-carbonyl)-5H-benzo[b]pyrido[2,3-e][1,4]diazepine-11(6H)-carboxylate

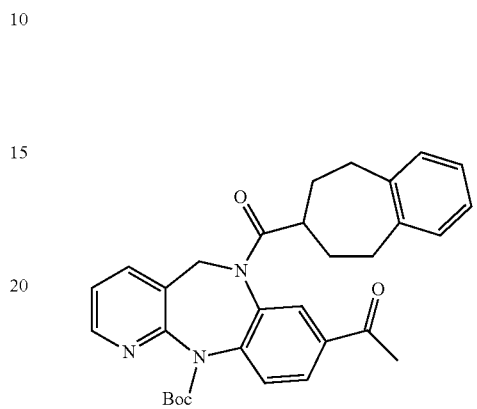

Step 1: To a mixture of 6,7,8,9-tetrahydro-5H-benzo[7]annulene-7-carboxylic acid (102 mg, 0.537 mmol) in DCM (1 mL) and a few drops of DMF was added oxalyl chloride (75 mg, 0.59 mmol) and the mixture was stirred for 1 h at room temperature. The mixture was concentrated under reduced pressure to afford 6,7,8,9-tetrahydro-5H-benzo[7]annulene-7-carbonyl chloride that was used immediately without further purification.

Step 2: To a mixture of tert-butyl 8-acetyl-5H-benzo[b]pyrido[2,3-e][1,4]diazepine-11(6H)-carboxylate (135 mg, 0.398 mmol) in DCM (200 μL) was added 6,7,8,9-tetrahydro-5H-benzo[7]annulene-7-carbonyl chloride (112 mg, 0.537 mmol). After 10 minutes at room temperature, pyridine (32 μL, 0.40 mmol) was added and the mixture was stirred for 30 minutes at room temperature. The mixture was then diluted with DCM and absorbed onto silica gel. The mixture was purified by column chromatography on silica gel (0-100% ethyl acetate gradient in hexanes) to afford tert-butyl 8-acetyl-6-(6,7,8,9-tetrahydro-5H-benzo[7]annulene-7-carbonyl)-5H-benzo[b]pyrido[2,3-e][1,4]diazepine-11(6H)-carboxylate. MS ESI calc'd for $C_{26}H_{26}N_3O_2$ [M-$C_5H_8O_2$+H]$^+$ 412, found 412. $^1$H NMR (600 MHz, CDCl$_3$) δ 8.38 (d, J=3.6 Hz, 1H), 8.01 (dd, J=8.3, 1.8 Hz, 1H), 7.96 (d, J=1.8 Hz, 1H), 7.80 (d, J=8.3 Hz, 1H), 7.48 (d, J=7.3 Hz, 1H), 7.16 (dd, J=7.6, 4.7 Hz, 1H), 7.04 (dd, J=10.9, 7.7, 4H), 6.18 (s, 1H), 4.07-3.93 (m, 1H), 2.80-2.61 (m, 5H), 2.60-2.50 (m, 2H), 2.08 (s, 1H), 1.90-1.80 (m, 1H), 1.59 (s, 3H), 1.48 (s, 9H).

Intermediate 15

(2-Bromo-5H-dipyrido[2,3-b:2',3'-e][1,4]diazepin-11(10H)-yl)(6,7,8,9-tetrahydro-5H-benzo[7]annulen-7-yl)methanone

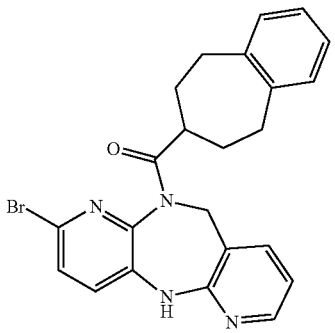 [SMILES: O=C(C1CCc2ccccc2CC1)N1Cc2cccnc2Nc2ccc(Br)nc21]

Step 1: A 10 L, 4-necked round-bottom flask was purged and maintained with an inert atmosphere of nitrogen while a mixture of 2-bromopyridine-3-carbaldehyde (78.5 g, 422 mmol) in tert-Butanol (6 L), 6-bromo-2-nitropyridin-3-amine (100 g, 422 mmol), XantPhos (24.43 g, 42.22 mmol), $Pd_2(dba)_3$ (19.35 g, 18.69 mmol), and sodium carbonate (56.5 g, 533 mmol) was added. The resulting mixture was heated to 90° C. for 18 h. Upon cooling the mixture to 30° C., the mixture was quenched by the addition of water/ice (10 L). The solids were filtered out and the filtrate was extracted with dichloromethane (3×3 L). The combined organic layers were dried over anhydrous sodium sulfate, filtered and concentrated under reduced pressure. The residue was washed with methanol (2×500 mL) to afford 2-[(6-bromo-2-nitropyridin-3-yl)amino]pyridine-3-carbaldehyde as a solid that was taken on to the next step without further purification.

Step 2: A 2 L, 4-necked round-bottom flask was purged and maintained with an inert atmosphere of nitrogen while a mixture of 2-[(6-bromo-2-nitropyridin-3-yl)amino]pyridine-3-carbaldehyde (70.0 g, 217 mmol) in ethanol/EA (700 mL) was added. This was followed by the addition of $SnCl_2.H_2O$ (195.5 g, 866.4 mmol) in several batches and the resulting mixture was stirred at room temperature for 18 h. The mixture was then concentrated under reduced pressure. The residue was diluted with brine (300 mL) and then extracted with ethyl acetate (2×800 mL). The combined organic layers were dried over anhydrous sodium sulfate, filtered and concentrated under reduced pressure. The residue was diluted with THF/MeOH (1:1 mixture, 400 mL), followed by the addition of $NaCNBH_3$ (38.1 g, 606 mmol) in several batches. The resulting mixture was stirred at room temperature for 2 h and then concentrated under reduced pressure. The residue was purified by column chromatography on silica gel (ethyl acetate/petroleum ether, 1:1) to afford 2-bromo-10,11-dihydro-5H-dipyrido[2,3-b:2',3'-e][1,4]diazepine as a solid.

Step 3: To a mixture of 2-bromo-10,11-dihydro-5H-dipyrido[2,3-b:2',3'-e][1,4]diazepine (200 mg, 0.722 mmol) and 6,7,8,9-tetrahydro-5H-benzo[7]annulene-7-carboxylic acid (137 mg, 0.722 mmol) in acetonitrile (11 mL) was added resin-bound triphenylphosphine (2.05 mmol/g loading, 1.06 g, 2.17 mmol) and trichloroacetonitrile (0.36 mL, 3.6 mmol). The mixture was then heated to 120° C. for 5 minutes. Upon cooling to room temperature, the mixture was filtered and then concentrated under reduced pressure. The residue was purified by reverse phase HPLC (acetonitrile/water with a 0.1% TFA modifier). The desired fractions were combined, diluted with ethyl acetate and washed sequentially with aqueous saturated sodium bicarbonate and then brine. The organic layer was separated, dried over magnesium sulfate, filtered and concentrated under reduced pressure to afford (2-bromo-5H-dipyrido[2,3-b:2',3'-e][1,4]diazepin-11(10H)-yl)(6,7,8,9-tetrahydro-5H-benzo[7]annulen-7-yl)methanone. MS 449, 451 (M+1, M+3). $^1H$ NMR (600 MHz, DMSO-$d_6$) δ 9.80 (s, 1H), 8.07 (d, J=4.4 Hz, 1H), 7.66 (d, J=8.4 Hz, 1H), 7.49 (d, J=7.7 Hz, 2H), 7.12-6.92 (m, 4H), 6.77 (d, J=4.9 Hz, 1H), 5.39-4.06 (m, 2H), 2.82-2.70 (m, 1H), 2.70-2.49 (m, 4H), 1.32-1.15 (m, 4H).

Intermediate 16

8,8-Difluorobicyclo[3.2.1]octane-3-carboxylic acid

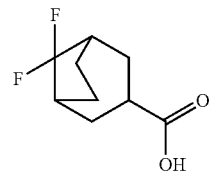

Step 1: A mixture of diethylaminosulfur trifluoride in DCM (5 mL) was added dropwise to a mixture of ethyl 8-oxobicyclo[3.2.1]octane-3-carboxylate (3.0 g, 15 mmol) in DCM (25 mL) at 0° C. The resulting mixture was allowed to warm to room temperature and was then stirred for 18 h at room temperature. The mixture was poured into aqueous saturated sodium bicarbonate at 0° C. and then extracted with DCM. The organic layer was dried over magnesium sulfate, filtered and concentrated under reduced pressure. The crude oil was purified by column chromatography on silica gel (10% petroleum ether with ethyl acetate) to afford ethyl 8,8-difluorobicyclo[3.2.1]octane-3-carboxylate that was taken on to the next step without characterization.

Step 2: LiOH (0.60 g, 25 mmol) was added to a mixture of ethyl 8,8-difluorobicyclo[3.2.1]octane-3-carboxylate (1.0 g, 4.6 mmol) in THF/$H_2O$ (10 mL/10 mL). The resulting mixture was heated to 60° C. for 18 h. Upon cooling to room temperature, the mixture was extracted with ethyl acetate. The water layer was separated, the pH was adjusted to ~4 at 0° C. and then extracted with ethyl acetate (2×). The combined organic layers were dried over magnesium sulfate, filtered and concentrated under reduced pressure to afford 8,8-difluorobicyclo[3.2.1]octane-3-carboxylic acid. 1H NMR (300 MHz, DMSO-$d_6$) δ 2.6 (m 1H), 2.2 (t, 2H), 1.8-1.7 (m, 6H), 1.6-1.5 (t, 2H).

Intermediate 17

Di-tert-Butyl 8-bromo-5H-benzo[b]pyrido[2,3-e][1,4]diazepine-6,11-dicarboxylate

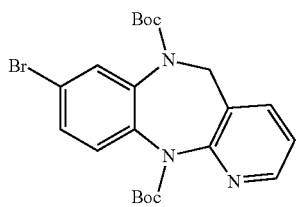 [SMILES: CC(C)(C)OC(=O)N1Cc2cccnc2N(C(=O)OC(C)(C)C)c2ccc(Br)cc21]

TEA (1.8 ml, 13 mmol) was added to a mixture of 8-Bromo-6,11-dihydro-5H-benzo[b]pyrido[2,3-e][1,4]diazepine (500 mg, 1.81 mmol), di-tert-butyl dicarbonate (1.98 g, 9.05 mmol) and DMAP (442 mg, 3.62 mmol) in THF (12 mL). The mixture was heated to 75° C. for 18 hours. Upon cooling to room temperature, the mixture was diluted with ethyl acetate, washed with water (2×50 mL), dried over anhydrous magnesium sulfate, filtered and concentrated under reduced pressure. The residue was purified by reverse phase liquid chromatography (ACN/water with 0.1% TFA modifier). The desired fractions were concentrated under reduced pressure, reconstituted in ethyl acetate, and washed saturated sodium bicarbonate. The organic layer was dried over magnesium sulfate, filtered and concentrated under reduced pressure to afford di-tert-butyl 8-bromo-5H-benzo[b]pyrido[2,3-e][1,4]diazepine-6,11-dicarboxylate. MS 477 (M+1). $^1$H NMR (600 MHz, CDCl$_3$) δ 8.44 (s, 1H), 7.52 (m, 2H), 7.45 (m, 2H), 7.20 (m, 1H), 4.99 (m, 2H), 1.48 (s, 9H), 1.42 (s, 9H).

Intermediate 18

(3aR,7aR)-Octahydrobenzofuran-5-carboxylic acid and (3aS,7aS)-octahydrobenzofuran-5-carboxylic acid

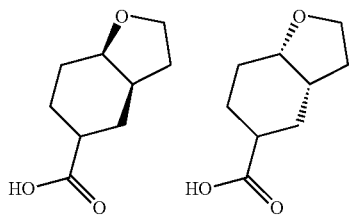

Step 1: A mixture of methyl 2,3-dihydrobenzofuran-5-carboxylate (4.29 g, 24.1 mmol) in methanol (100 mL) was degassed via subsurface bubbling with argon for 10 minutes. 5% Rhodium/Alumina (1.48 g, 7.22 mmol) was added and the mixture was evacuated and backfilled with hydrogen two times. The mixture was then stirred for 72 h at a hydrogen pressure of 55 psi. The mixture was filtered through celite and the filtrate was concentrated under reduced pressure to afford a crude mixture of (3aR,7aR)-methyl octahydrobenzofuran-5-carboxylate and (3aS,7aS)-methyl octahydrobenzofuran-5-carboxylate that was used in the subsequent reaction without further purification.

Step 2: To the crude mixture of (3aR,7aR)-methyl octahydrobenzofuran-5-carboxylate and (3aS,7aS)-methyl octahydrobenzofuran-5-carboxylate (1.50 g, 8.14 mmol) was added sodium methoxide (25% by weight in methanol, 7.0 g, 33 mmol) and the mixture was heated to 50° C. for 18 h. Upon cooling to room temperature, the mixture was concentrated under reduced pressure. To the residue was added water (10 mL) and the mixture was stirred at room temperature for 10 minutes. The water layer was acidified with aqueous HCl (1 N, 15 mL) and then extracted with EtOAc (2×50 mL). The combined organic layers were washed with brine, dried over sodium sulfate, filtered and concentrated under reduced pressure to afford (3aR,7aR)-octahydrobenzofuran-5-carboxylic acid and (3aS,7aS)-octahydrobenzofuran-5-carboxylic acid as a mixture of 4 diastereomers. MS: 171 (M+1)

Intermediate 19

(2S,3aR,7aR)-Octahydrobenzofuran-5-carboxylic acid and (2R,3aS,7aS)-octahydrobenzofuran-5-carboxylic acid

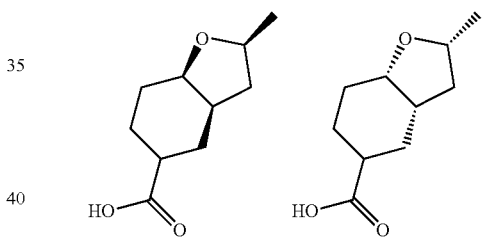

Step 1: A mixture of (2S,3aR,7aR)-methyl 2-methyloctahydrobenzofuran-5-carboxylate and (2R,3aS,7aS)-methyl 2-methyloctahydrobenzofuran-5-carboxylate was prepared from methyl 2-methylbenzofuran-5-carboxylate (2.3 g, 12 mmol) using the reaction conditions described in Intermediate 17, step 1.

Step 2: To a mixture of (2S,3aR,7aR)-methyl 2-methyloctahydrobenzofuran-5-carboxylate and (2R,3aS,7aS)-methyl 2-methyloctahydrobenzofuran-5-carboxylate (1.0 g, 5.0 mmol) in MeOH (20 mL) was added KOtBu (1.7 g, 15 mmol) and the mixture was stirred overnight at room temperature. Water (2 mL) was then added and the mixture was stirred for 30 minutes at room temperature. The mixture was acidified with aqueous HCl (2 N, 7.6 mL, 15 mmol) and then extracted with EtOAc (2×50 mL). The combined organics were washed with brine, dried over sodium sulfate, filtered and concentrated under reduced pressure to afford a mixture of (2S,3aR,7aR)-octahydrobenzofuran-5-carboxylic acid and (2R,3aS,7aS)-octahydrobenzofuran-5-carboxylic acid as a mixture of 4 isomers. MS: 185 (M+1).

Intermediate 20

Octahydro-1,4-benzodioxine-2-carboxylic acid

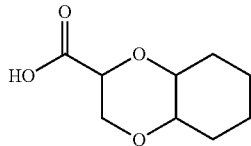 [SMILES: O=C(O)C1COC2CCCCC2O1]

Intermediate 20 was prepared using the procedure described for Intermediate 19 using LiOH instead of KOtBu as base in Step 2. MS: 187 (M+1).

Intermediate 21

Octahydro-2H-chromene-6-carboxylic acid

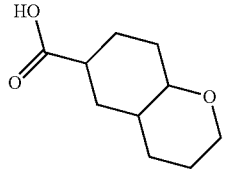 [SMILES: O=C(O)C1CCC2OCCCC2C1]

Step 1: A mixture of methyl chroman-6-carboxylate (3.39 g, 17.6 mmol) in acetic acid (75 mL) was degassed via subsurface bubbling with argon for 10 minutes. Platinum oxide (0.80 g, 3.5 mmol) was added and the mixture was stirred for 24 h at a hydrogen pressure of 55 psi. The mixture was then filtered through celite and the filtrate was concentrated under reduced pressure to afford a crude mixture of methyl octahydro-2H-chromene-6-carboxylate that was used in the subsequent step without further purification.

Step 2: A mixture of methyl octahydro-2H-chromene-6-carboxylate (626 mg, 3.16 mmol) in THF (10 mL) was added sodium hydride (60% mixture in mineral oil, 253 mg, 6.31 mmol) and the mixture was heated to 55° C. for 3 h to epimerize the ester. Upon cooling to room temperature, a mixture of potassium hydroxide (266 mg, 4.74 mmol) in 1:1 methanol:water (3 mL) was added and allowed to stir until the reaction was complete by TLC. The mixture was then acidified with aqueous HCl (2 N, 10 mL) and then extracted with ethyl acetate (50 mL). The organic layer was then washed with brine, dried over sodium sulfate, filtered and concentrated under reduced pressure to afford octahydro-2H-chromene-6-carboxylic acid as a mixture of isomers. MS 185 (M+1).

Intermediate 22

5-Methoxybicyclo[2.2.2]octane-2-carboxylic acid

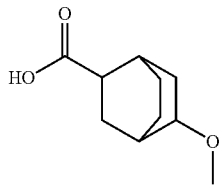

Step 1: To a mixture of methyl 5-oxobicyclo[2.2.2]octane-2-carboxylate (625 mg, 3.43 mmol) in DCM (17 mL) at −78° C. was added methoxytrimethylsilane (0.52 mL, 3.8 mmol) followed by trimethylsilyl trifluoromethanesulfonate (62 µL, 3.4 mmol). The mixture was stirred at −78° C. for 20 minutes. Triethylsilane (600 µL, 3.77 mmol) was added, the dry ice bath was removed and the mixture was allowed to warm to room temperature overnight. The mixture was then quenched with methanol, concentrated under reduced pressure and purified by column chromatography on silica gel (0-5% ethyl acetate gradient in DCM) to afford methyl 5-methoxybicyclo[2.2.2]octane-2-carboxylate as a mixture of isomers that was used in the next step without further purification or characterization.

Step 2: To a mixture of methyl 5-methoxybicyclo[2.2.2]octane-2-carboxylate (500 mg, 2.52 mmol) in THF (10 mL) and water (2.5 mL) was added lithium hydroxide (242 mg, 10.1 mmol) and the mixture was heated to 60° C. for 5 h. Upon cooling to room temperature, the mixture was quenched with aqueous HCl (2.0 N, 5.3 mL) to pH=5. The mixture was extracted with ethyl acetate (2×) and the combined organic layers were dried over sodium sulfate, filtered and concentrated under reduced pressure to afford 5-methoxybicyclo[2.2.2]octane-2-carboxylic acid as a mixture of isomers that was used without further purification. 1H NMR (500 MHz, CDCl$_3$) δ 3.49-3.41 (m, 1H), 3.35-3.28 (m, 3H), 2.74-2.49 (m, 1H), 2.20-1.98 (m, 2H), 1.98-1.89 (m, 2H), 1.88-1.76 (m, 2H), 1.72-1.44 (m, 2H), 1.31 (m, 2H).

Intermediate 23

(3aS,6aS)-4-methoxyoctahydropentalene-1-carboxylic acid

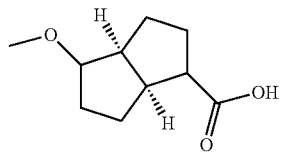

Intermediate 24

(3aS,6aS)-4-ethoxyoctahydropentalene-1-carboxylic acid

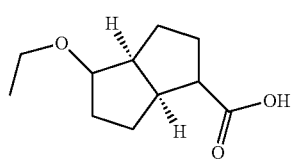

Intermediates 23-24 were prepared using the procedure described for Intermediate 22 from methyl (3aS,6aS)-4-oxooctahydropentalene-1-carboxylate described below. Intermediate 23 MS: 185 (M+1). Intermediate 24 MS: 199 (M+1).

Intermediate 25

(R)-(8-bromo-5,11-dihydro-6H-benzo[b]pyrido[2,3-e][1,4]diazepin-6-yl)(2,3-dihydrobenzo[b][1,4]dioxin-2-yl)methanone

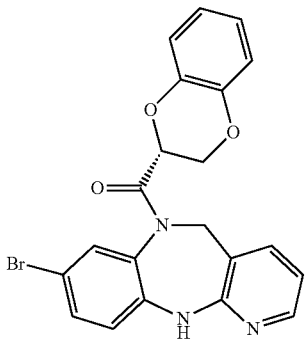 [SMILES: O=C([C@H]1COc2ccccc2O1)N1Cc2cccnc2Nc2ccc(Br)cc21]

To a vial containing (R)-2,3-dihydrobenzo[b][1,4]dioxine-2-carboxylic acid (300 mg, 1.67 mmol) in DCM (10 mL) was added oxalyl chloride (0.200 mL, 2.28 mmol) and DMF (20 μL) slowly. The resulting reaction was stirred at ambient temperature for 1 h. The solvent was concentrated under reduced pressue and then DCE (4 mL) was added. The resulting mixture was added dropwise to a vial containing a mixture of 8-bromo-6,11-dihydro-5H-benzo[b]pyrido[2,3-e][1,4]diazepine (420 mg, 1.52 mmol) and N,N-dimethylpyridin-4-amine (19 mg, 0.15 mmol) in DCE (6 mL) at 80° C. The resulting reaction mixture was stirred at 80° C. for 16 h. The reaction was allowed to cool to room temperature and diluted with EtOAc (50 mL). The mixture was then washed with saturated aqueous Na$_2$CO$_3$ (20 mL) and then brine (20 mL). The organic layer was separated, dried over magenisum sulfate, filtered, and concentrated under reduced pressure. The residue was purified by column chromatography on silica gel (10-100% EtOAc/hexane) to afford (R)-(8-bromo-5,11-dihydro-6H-benzo[b]pyrido[2,3-e][1,4]diazepin-6-yl)(2,3-dihydrobenzo[b][1,4]dioxin-2-yl)methanone as a solid. MS: 438, 440 (M, M+2).

Intermediate 26

3-(6,11-Dihydro-5H-benzo[b]pyrido[2,3-e][1,4]diazepin-8-yl)-8-oxa-3-azabicyclo[3.2.1]octane

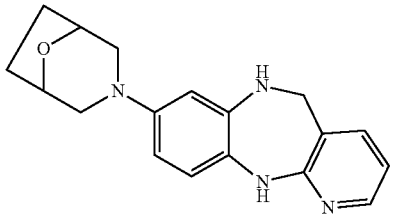 [SMILES: c1cnc2c(c1)CNc1cc(N3CC4CCC(C3)O4)ccc1N2]

A reaction vessel was charged with lithium bis(trimethylsilyl)amide (1.0 M in THF, 64 mL, 64 mmol) followed by 8-bromo-6,11-dihydro-5H-pyrido[2,3-b][1,5]benzodiazepine, HCl (2.0 g, 6.4 mmol), 8-oxa-3-azabicyclo[3.2.1]octane hydrochloride (1.4 g, 9.6 mmol), and (2-dicyclohexylphosphino-2',6'-diisopropoxy-1,1'-biphenyl) [2-(2'-amino-1,1'-biphenyl)]palladium(II) methanesulfonate (RuPhos G3) (0.53 g, 0.64 mmol). The vessel was sealed and heated to 80° C. for 16 hours. The reaction mixture was allowed to cool to room temperature, diluted with saturated aqueous sodium bicarbonate and extracted with EtOAc (2×). The combined organic layers were washed with brine, dried over anhydrous magnesium sulfate, filtered, and concentrated under reduced pressure. The residue was purified by flash chromatography (30-100% EtOAc:Hex) to afford 3-(6,11-dihydro-5H-benzo[b]pyrido[2,3-e][1,4]diazepin-8-yl)-8-oxa-3-azabicyclo[3.2.1]octane. MS: 309 (M+1).

Intermediate 27

8-(4-fluoropiperidin-1-yl)-6,11-dihydro-5H-pyrido[2,3-b][1,5]benzodiazepine

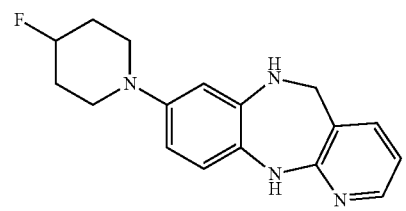 [SMILES: FC1CCN(c2ccc3c(c2)NCc2cccnc2N3)CC1]

Intermediate 27 was prepared using the procedure described for intermediate 26. MS: 299 (M+1).

Intermediates 28 and 29

(1R,4R)-5-(6,11-Dihydro-5H-benzo[b]pyrido[2,3-e][1,4]diazepin-8-yl)-2-oxa-5-azabicyclo[2.2.2]octane and (1S,4S)-5-(6,11-dihydro-5H-benzo[b]pyrido[2,3-e][1,4]diazepin-8-yl)-2-oxa-5-azabicyclo[2.2.2]octane

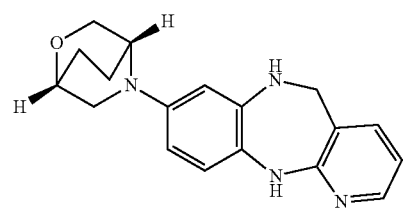

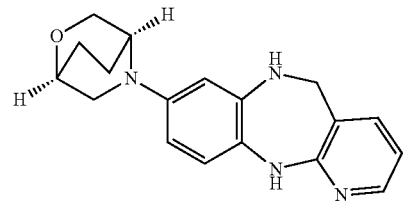

Step 1: To a mixture of 8-bromo-6,11-dihydro-5H-pyrido[2,3-b][1,5]benzodiazepine, HCl (5.0 g, 16 mmol) in THF (300 mL) was added triethylamine (18.0 mL, 130 mmol), di-tert-butyl dicarbonate (14 g, 64 mmol) and DMAP (2.3 g, 19 mmol). The mixture was heated to 70° C. for 18 h. Upon cooling to room temperature, the mixture was diluted with ethyl acetate, washed with water, dried over magnesium sulfate, filtered and concentrated under reduced pressure. The mixture was purified by column chromatography to afford di-tert-butyl 8-bromo-5H-benzo[b]pyrido[2,3-e][1,4]diazepine-6,11-dicarboxylate. MS: 376, 378 (M-C$_5$H$_8$O$_2$, M-C$_5$H$_8$O$_2$+2).

Step 2: To a mixture of di-tert-butyl 8-bromo-5H-benzo[b]pyrido[2,3-e][1,4]diazepine-6,11-dicarboxylate (1.0 g, 2.1 mmol), RuPhos-G1-palladacycle (171 mg, 0.210 mmol) and sodium tert-butoxide (1.0 g, 11 mmol) was added THF (22 mL) and water (5 mL). The mixture was evacuated and then purged with nitrogen 5 times and then heated to 80° C. for 18 h. Upon cooling to room temperature, the mixture was diluted with ethyl acetate and water. The organic layer was separated, dried over magnesium sulfate, filtered and concentrated under reduced pressure. The mixture was purified by column chromatography to afford di-tert-butyl 8-(2-oxa-5-azabicyclo[2.2.2]octan-5-yl)-5H-benzo[b]pyrido[2,3-e][1,4]diazepine-6,11-dicarboxylate as a mixture of enantiomers. The enantiomers were separated by SFC (Chiralcel OD-H column, 10%/90% methanol/CO$_2$ with 0.25% N,N-dimethylethanamine modifier) to afford di-tert-butyl 8-((1R,4R)-2-oxa-5-azabicyclo[2.2.2]octan-5-yl)-5H-benzo[b]pyrido[2,3-e][1,4]diazepine-6,11-dicarboxylate and di-tert-butyl 8-((1S,4S)-2-oxa-5-azabicyclo[2.2.2]octan-5-yl)-5H-benzo[b]pyrido[2,3-e][1,4]diazepine-6,11-dicarboxylate.

Characterization data for di-tert-butyl 8-((1R,4R)-2-oxa-5-azabicyclo[2.2.2]octan-5-yl)-5H-benzo[b]pyrido[2,3-e][1,4]diazepine-6,11-dicarboxylate (early eluting): MS: 409 (M-C$_5$H$_8$O$_2$+H).

Characterization data for di-tert-butyl 8-((1S,4S)-2-oxa-5-azabicyclo[2.2.2]octan-5-yl)-5H-benzo[b]pyrido[2,3-e][1,4]diazepine-6,11-dicarboxylate (late eluting): MS: 409 (M-C$_5$H$_8$O$_2$+H).

Step 3: To a mixture of di-tert-butyl 8-((1R,4R)-2-oxa-5-azabicyclo[2.2.2]octan-5-yl)-5H-benzo[b]pyrido[2,3-e][1,4]diazepine-6,11-dicarboxylate (177 mg, 0.348 mmol) in dichloromethane (2 mL) was added trifluoroacetic acid (200 µL, 2.61 mmol) and the mixture was allowed to stir overnight at room temperature. The mixture was concentrated and then taken up in ethyl acetate. The mixture was washed with saturated aqueous sodium bicarbonate, dried over magnesium sulfate, filtered and concentrated to afford (1R,4R)-5-(6,11-dihydro-5H-benzo[b]pyrido[2,3-e][1,4]diazepin-8-yl)-2-oxa-5-azabicyclo[2.2.2]octane. MS: 309 (M+H). 1 S,4S)-5-(6,11-dihydro-5H-benzo[b]pyrido[2,3-e][1,4]diazepin-8-yl)-2-oxa-5-azabicyclo[2.2.2]octane can be prepared using the procedure described in Step 3. MS: 309 (M+H).

Intermediate 30

8-(2-Oxa-5-azabicyclo[2.2.1]hept-5-yl)-6,11-dihydro-5H-pyrido[2,3-b][1,5]benzodiazepine

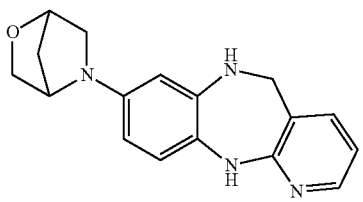 [SMILES: c1cnc2c(c1)CNc1cc(N3CC4CC3CO4)ccc1N2]

Intermediate 30 was prepared using the procedure described for intermediate 29. MS: 295 (M+1).

Intermediate 31

Methyl (3aS,6aS)-4-oxooctahydropentalene-1-carboxylate

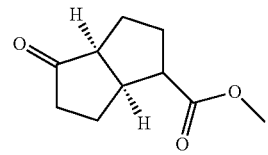

Step 1: Into a 3 L 4-necked round-bottom flask that was purged and maintained with an inert atmosphere of nitrogen, was added (1Z,5Z)-cycloocta-1,5-diene (200 g, 1.85 mol) in AcOH (1.2 L), diacetoxypalladium (8.30 g, 37.0 mmol), and plumbanetetrayl tetraacetate (820 g, 1.85 mol). The mixture was stirred for 48 h at room temperature. The reaction mixture was poured into 3 L of crushed ice/H$_2$O. The aqueous layer was extracted with Et$_2$O (3×3 L), washed with water (2×2 L) and Brine (2×200 mL). The combined organic layers were dried over anhydrous sodium sulfate, filtered, and concentrated under reduced pressure to give crude (3aS,6aS)-octahydropentalene-1,4-diyl diacetate.

Step 2: Into a 5 L 4-necked round-bottom flask that was purged and maintained with an inert atmosphere of nitrogen, was added (3aS,6aS)-octahydropentalene-1,4-diyl diacetate (410 g, 1.81 mol) in MeOH (2 L). Potassium hydroxide (203 g, 3.62 mol) was added in portions at 0° C. over 30 mins. The mixture was stirred for 30 mins at room temperature. The reaction mixture was poured into 5 L of crushed ice/H$_2$O. The aqueous layer was extracted with EtOAc (5×3 L), washed with water (1 L), and brine (1 L). The combined organic layers were dried over anhydrous sodium sulfate, filtered, and concentrated under reduced pressure. The residue was purified by column chromatography on silica gel (ethyl acetate/petroleum ether, 1:20-1:6) to give (3aS,6aS)-octahydropentalene-1,4-diol.

Step 3: Into a 3 L 4-necked round-bottom flask that was purged and maintained with an inert atmosphere of nitrogen, was added (3aS,6aS)-octahydropentalene-1,4-diol (109 g, 767 mmol) and tetrabutylammonium bromide (247 g, 767 mmol) in THF (1.1 L). Sodium hydride (30.7 g, 767 mmol) was added portionwise at 0° C. The mixture was stirred for 1 h at room temperature, and then 1-(chloromethyl)-4-methoxybenzene (120 g, 767 mmol) was added dropwise at room temperature. The mixture was stirred overnight at room temperature. The reaction mixture was poured into 2 L of crushed ice/H$_2$O. The aqueous layer was extracted with EtOAc (3×1.5 L), and the combined organic layers were washed with water (1 L) and brine (2×1 L). The combined organic layers were dried over anhydrous sodium sulfate, filtered, and concentrated under reduced pressure. The residue was purified by column chromatography on silica gel (ethyl acetate/petroleum ether, 1:100~1:50) to give (3aS,6aS)-4-((4-methoxybenzyl)oxy)octahydropentalen-1-ol.

Step 4: Into a 3 L 4-necked round-bottom flask that was purged and maintained with an inert atmosphere of nitrogen, was added (3aS,6aS)-4-((4-methoxybenzyl)oxy)octahydropentalen-1-ol (143 g, 545 mmol) and DCM (1.4 L). PCC (176 g, 818 mmol) was added portionwiase at room temperature and the mixture was stirred overnight at room temperature. The mixture was filtered, and the filtrate was concentrated under reduced pressure. The residue was purified by column chromatography on silica gel (ethyl acetate/petroleum ether, 1:100~1:30) to give (3aS,6aS)-4-((4-methoxybenzyl)oxy)hexahydropentalen-1(2H)-one.

Step 5: Into a 5 L 4-necked round-bottom flask that was purged and maintained with an inert atmosphere of nitrogen, was added (3aS,6aS)-4-((4-methoxybenzyl)oxy)hexahydropentalen-1(2H)-one (92.3 g, 355 mmol) and THF (923 ml). Lithium bis(trimethylsilyl)amide (1.0 M in THF, 425 mL, 425 mmol) was added dropwise at −78° C. The mixture was stirred for 30 mins at −78° C. To the mixture was added 1,1,1-trifluoro-N-phenyl-N-((trifluoromethyl)sulfonyl)methanesulfonamide (139 g, 390 mmol) in THF (462 mL) dropwise at −78° C. The mixture was allowed to warm to room temperature and stirred overnight. The reaction mixture was poured into 1 L of saturated aqueous sodium bicarbonate. The aqueous layer was extracted with EtOAc (3×2 L), washed with water (1 L), and brine (2×1 L). The combined organic layer was dried over anhydrous sodium sulfate, filtered, and concentrated under reduced pressure. The residue was purified by column chromatography on silica gel (ethyl acetate/petroleum ether, 1:100~1/80) to give (3aS,6aS)-4-((4-methoxybenzyl)oxy)-3,3a,4,5,6,6a-hexahydropentalen-1-yl trifluoromethanesulfonate.

Step 6: Into a 3 L 4-necked round-bottom flask that was purged and maintained with an inert atmosphere of nitrogen, was added (3aS,6aS)-4-((4-methoxybenzyl)oxy)-3,3a,4,5,6,6a-hexahydropentalen-1-yl trifluoromethanesulfonate (90.0 g, 229 mmol) and N,N-diisopropylethylamine (41.5 g, 321 mmol) in DMF (450 mL)/MeOH (450 mL). The flask was evacuated and flushed three times with CO. To the mixture was added [1,1′-bis(diphenylphosphino)ferrocene]dichloropalladium(II) (10.1 g, 13.8 mmol). The flask was evacuated and flushed two times with CO. The mixture was heated for to 50° C. for 3 h. Upon cooling to room temperature, the reaction mixture was poured into 1 L of crushed ice/H$_2$O and the aqueous layer was extracted with EtOAc (3×2 L). The combined organic layers were washed with water (1 L), and brine (2×1 L). The organic layer was dried over anhydrous sodium sulfate, filtered, and concentrated under reduced pressure. The residue was purified by column chromatography on silica gel (ethyl acetate/petroleum ether, 1:10) to give (3aS,6aS)-methyl 4-((4-methoxybenzyl)oxy)-3,3a,4,5,6,6a-hexahydropentalene-1-carboxylate.

Step 7: Into a 2 L round-bottom flask that was purged and maintain with an inert atmosphere of nitrogen, was added (3aS,6aS)-methyl 4-((4-methoxybenzyl)oxy)-3,3a,4,5,6,6a-hexahydropentalene-1-carboxylate (52 g, 172 mmol) and Pd/C (10% loading, 21 g, 20 mmol) in MeOH (520 mL). The flask was evacuated and flushed three times with hydrogen. The mixture was stirred for two days at room temperature under an atmosphere of hydrogen. The solids were filtered and washed with MeOH (3×500 mL). The combined organic layers were concentrated under reduced pressure. The residue was purified by column chromatography on silica gel (ethyl acetate/petroleum ether, 1:10) to give (1S,3aS,6aS)-methyl 4-hydroxyoctahydropentalene-1-carboxylate.

Step 8: Into a 1 L 4-necked round-bottom flask that was purged and maintained with an inert atmosphere of nitrogen, was added (1S,3aS,6aS)-methyl 4-hydroxyoctahydropentalene-1-carboxylate (25 g, 136 mmol) and DCM (375 mL). PCC (58.5 g, 271 mmol) was added in portions at room temperature. The mixture was stirred overnight at room temperature. The solids were filtered, and the residue was concentrated under reduced pressure. The residue was purified by column chromatography on silica gel (ethyl acetate/petroleum ether, 1:50~1/20) to give (1S,3aS,6aS)-methyl 4-oxooctahydropentalene-1-carboxylate.

Step 9: Into a 50 mL 3-necked round-bottom flask that was purged and maintained with an inert atmosphere of nitrogen, was added (1S,3aS,6aS)-methyl 4-oxooctahydropentalene-1-carboxylate (2.0 g, 11 mmol) and MeOH (20 mL). Sodium methanolate (0.59 g, 11 mmol) was added portionwise at room temperature. The mixture was stirred for 3 days at room temperature. The mixture was poured into HCl (0.5 N in water, 50 mL), and the aqueous layer was extracted with EtOAc (3×100 mL). The combined organic layers were washed with water (50 mL) and brine (2×50 mL). The organic layer was dried over anhydrous sodium sulfate, filtered, and concentrated under reduced pressure. The residue was purified by column chromatography on silica gel (ethyl acetate/petroleum ether, 1:10) to give (3aS,6aS)-methyl 4-oxooctahydropentalene-1-carboxylate. GCMS: 182 [M]. $^1$H NMR (300 MHz, CDCl$_3$): δ 3.71 (s, 3H), 3.05-2.99 (m, 1H), 2.77-2.65 (m, 1H), 2.56-2.49 (m, 1H), 2.35-2.3 (m, 2H), 2.28-2.10 (m, 2H), 2.06-1.77 (m, 4H).

EXAMPLES

Examples 1 and 2

6-{[(3r,8r)-3-Methoxybicyclo[3.2.1]oct-8-yl]carbonyl}-8-morpholin-4-yl-6,11-dihydro-5H-pyrido[2,3-b][1,5]benzodiazepine (Ex. 1) and 6-{[(3s,8s)-3-methoxybicyclo[3.2.1]oct-8-yl]carbonyl}-8-morpholin-4-yl-6,11-dihydro-5H-pyrido[2,3-b][1,5]benzodiazepine (Ex. 2)

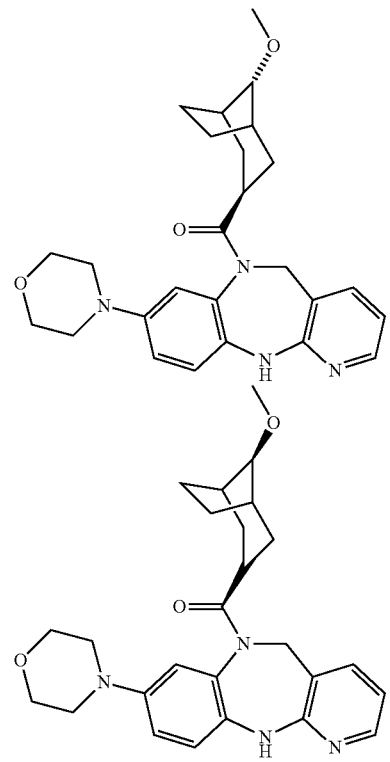

Step 1: To a mixture of methoxytrimethylsilane (0.53 ml, 3.8 mmol) in DCM (19 mL) at −78° C. was added ethyl 8-oxobicyclo[3.2.1]octane-3-carboxylate (0.68 g, 3.5 mmol). Trimethylsilyl trifluoromethanesulfonate (0.10 mL, 0.58 mmol) was added and the mixture was stirred for 1 h at −78° C. Triethylsilane (0.67 mL, 4.2 mmol) was added, the cooling bath was removed and the reaction was allowed to warm to room temperature for 18 h. The reaction was quenched with saturated aqueous sodium bicarbonate and extracted with DCM. The organic layer was then dried over sodium sulfate, filtered, and concentrated under reduced pressure. The mixture was purified by column chromatography on silica gel (0-40% EtOAc/hexanes) to afford ethyl 8-methoxybicyclo[3.2.1]octane-3-carboxylate. MS 213 (M+1).

Step 2: To a mixture of ethyl 8-methoxybicyclo[3.2.1]octane-3-carboxylate (500 mg, 2.36 mmol) in THF (1.3 mL) and water (6.5 mL) was added lithium hydroxide (0.14 g, 5.9 mmol) and the mixture was allowed to stir at room temperature for 18 h. The mixture was then acidified to pH=4 with aqueous HCl (1 N) and then extracted with ethyl acetate (2×). The combined organic layers were dried over sodium sulfate, filtered, and concentrated under reduced pressure to afford 8-methoxybicyclo[3.2.1]octane-3-carboxylic acid as a mixture of isomers that was taken on to the next step.

Step 3: To a mixture of 4-(6,11-dihydro-5H-benzo[b]pyrido[2,3-e][1,4]diazepin-8-yl)morpholine (70 mg, 0.25 mmol), polymer supported triphenylphosphine (2.06 mmol/g loading, 0.361 g, 0.744 mmol) and 8-methoxybicyclo[3.2.1]octane-3-carboxylic acid (55 mg, 0.30 mmol) was added acetonitrile (10 mL). Trichloroacetonitrile (0.124 ml, 1.24 mmol) was added and the mixture was heated to 110° C. for 15 minutes in a microwave reactor. Upon cooling to room temperature, the mixture was filtered through a fritted funnel and the solids were washed with 1:1 DCM/MeOH (10 mL). The filtrate was concentrated under reduced pressure and purified by reverse phase HPLC (ACN/water with 0.1% TFA modifier). The purified product was then purified by achiral SFC (ES Basic, 2.1×25 cm, 90/10 CO$_2$/MeOH with 0.25% N,N-dimethylethylamine modifier, flow rate: 70 mL/min, 6 min run time, WL: 220 nM) to afford 6-{[(3r,8r)-3-methoxybicyclo[3.2.1]oct-8-yl]carbonyl}-8-morpholin-4-yl-6,11-dihydro-5H-pyrido[2,3-b][1,5]benzodiazepine and 6-{[(3s,8s)-3-methoxybicyclo[3.2.1]oct-8-yl]carbonyl}-8-morpholin-4-yl-6,11-dihydro-5H-pyrido[2,3-b][1,5]benzodiazepine.

Characterization data for isomer 1 (first eluting) enantiomer: MS: 449 (M+1). $^1$H NMR (600 MHz, DMSO-d$_6$) δ 9.10 (s, 1H), 7.96-7.93 (m, 1H), 7.38 (d, J=7.2 Hz, 1H), 7.14 (d, J=8.9 Hz, 1H), 6.83-6.79 (m, 1H), 6.74-6.73 (m, 1H), 6.61-6.57 (m, 1H), 5.21 (d, J=14.8 Hz, 1H), 3.78 (d, J=15.3 Hz, 1H), 3.70-3.67 (m, 3H), 3.13-3.11 (m, 2H), 3.09 (s, 3H), 3.01-2.97 (m, 4H), 2.12-2.07 (m, 1H), 1.96-1.91 (m, 1H), 1.83-1.80 (m, 1H), 1.71-1.68 (m, 1H), 1.63-1.57 (m, 1H), 1.35-1.31 (m, 1H), 1.24-1.18 (m, 2H), 1.03-1.00 (m, 1H), 0.92-0.87 (m, 1H), 0.59-0.52 (m, 1H).

Characterization data for isomer 2 (second eluting) enantiomer: MS: 449 (M+1). $^1$H NMR (600 MHz, DMSO-d$_6$) δ 9.07 (s, 1H), 7.95 (d, J=4.8 Hz, 1H), 7.37 (d, J=7.2 Hz, 1H), 7.18 (d, J=8.9 Hz, 1H), 6.89 (d, J=8.9 Hz, 1H), 6.85 (s, 1H), 6.67-6.57 (m, 1H), 5.12 (d, J=15.0 Hz, 1H), 3.85 (d, J=14.8 Hz, 1H), 3.70 (m, 4H), 3.19-3.15 (m, 1H), 3.12 (s, 3H), 3.06-3.02 (m, 2H), 2.98-2.93 (m, 2H), 2.06-1.78 (m, 4H), 1.52 (m, 1H), 1.40 (m, 1H), 1.25-1.15 (m, 3H), 0.72-0.63 (m, 1H), 0.60-0.51 (m, 1H).

Example 3

2-Methyl-2-[6-(6,7,8,9-tetrahydro-5H-benzo[7]annulen-7-ylcarbonyl)-6,11-dihydro-5H-pyrido[2,3-b][1,5]benzodiazepin-8-yl]propanenitrile

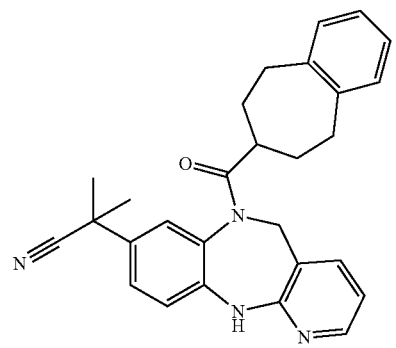 [SMILES: CC(C)(C#N)c1ccc2c(c1)N(C(=O)C1CCc3ccccc3CC1)Cc1cccnc1N2]

To a microwave vial was added 2-(6,11-dihydro-5H-benzo[b]pyrido[2,3-e][1,4]diazepin-8-yl)-2-methylpropanenitrile, HCl salt (110 mg, 0.366 mmol), 6,7,8,9-tetrahydro-5H-benzo[7]annulene-7-carboxylic acid (73 mg, 0.38 mmol) and polymer supported triphenylphosphine (1.94 mmol/g, 566 mg, 1.10 mmol). The mixture was suspended in acetonitrile (3.0 mL), and trichloroacetonitrile (0.18 mL, 1.8 mmol) was added. The mixture was heated to 150° C. for 10 minutes in a microwave reactor. Upon cooling to room temperature, the mixture was filtered and purified by reverse phase HPLC (ACN/water with 0.1% TFA modifier). The fractions containing product were combined, diluted with ethyl acetate, and then neutralized with saturated aqueous sodium bicarbonate. The organic layer was dried over magnesium sulfate, filtered, and concentrated under reduced pressure to afford 2-methyl-2-[6-(6,7,8,9-tetrahydro-5H-benzo[7]annulen-7-ylcarbonyl)-6,11-dihydro-5H-pyrido[2,3-b][1,5]benzodiazepin-8-yl]propanenitrile as a solid. MS 437 (M+1). $^1$H NMR (600 MHz, DMSO-d$_6$) δ 9.66 (s, 1H), 8.06-8.01 (m, 1H), 7.49 (d, J=7.0 Hz, 1H), 7.43 (s, 1H), 7.39-7.35 (m, 2H), 7.05-7.03 (m, 1H), 7.02-6.95 (m, 2H), 6.93-6.90 (m, 1H), 6.75-6.72 (m, 1H), 5.17 (d, J=15.0 Hz, 1H), 3.93 (d, J=14.8 Hz, 1H), 2.78-2.67 (m, 2H), 2.60-2.53 (m, 1H), 2.45-2.42 (m, 1H), 2.36-2.27 (m, 1H), 2.21-2.14 (m, 1H), 1.67 (s, 6H), 1.44-1.34 (m, 1H), 1.33-1.26 (m, 1H), 1.03-0.92 (m, 1H).

The compounds in the following table were prepared using the methodology herein and the general procedure described in Example 3.

| Ex. No. | Structure | Chemical Name | [M + H]+ |
| --- | --- | --- | --- |
| 4 | 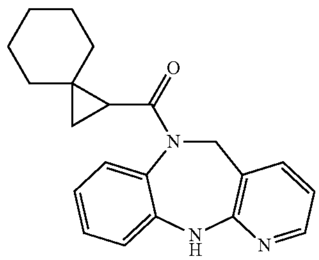 [SMILES: O=C(C1CC12CCCCC2)N1Cc2cccnc2Nc2ccccc21] | 6-(spiro[2.5]oct-1-ylcarbonyl)-6,11-dihydro-5H-pyrido[2,3-b][1,5]benzodiazepine | 334 |
| 5 | 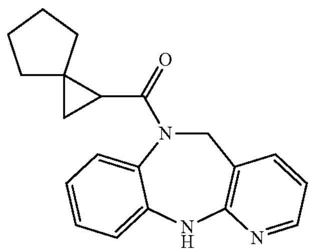 [SMILES: O=C(C1CC12CCCC2)N1Cc2cccnc2Nc2ccccc21] | 6-(spiro[2.4]hept-1-ylcarbonyl)-6,11-dihydro-5H-pyrido[2,3-b][1,5]benzodiazepine | 320 |
| 6 | 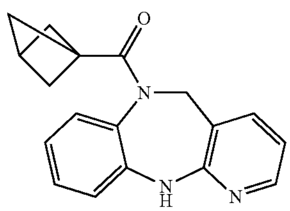 [SMILES: O=C(N1Cc2cccnc2Nc2ccccc21)C12CC(C1)C2] | 6-(bicyclo[1.1.1]pent-1-ylcarbonyl)-6,11-dihydro-5H-pyrido[2,3-b][1,5]benzodiazepine | 292 |
| 7 | 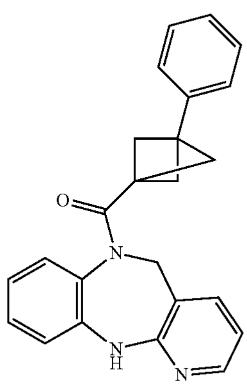 [SMILES: O=C(N1Cc2cccnc2Nc2ccccc21)C12CC(c3ccccc3)(C1)C2] | 6-[(3-phenylbicyclo[1.1.1]pent-1-yl)carbonyl]-6,11-dihydro-5H-pyrido[2,3-b][1,5]benzodiazepine | 368 |
| 8 | 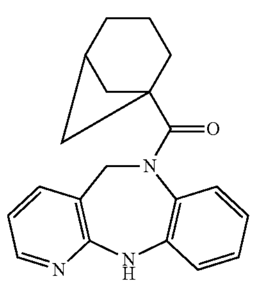 [SMILES: O=C(N1Cc2cccnc2Nc2ccccc21)C12CCCC(C1)C2] | 6-(bicyclo[3.1.1]hept-1-ylcarbonyl)-6,11-dihydro-5H-pyrido[2,3-b][1,5]benzodiazepine | 320 |

| Ex. No. | Structure | Chemical Name | [M + H]+ |
|---|---|---|---|
| 9 | 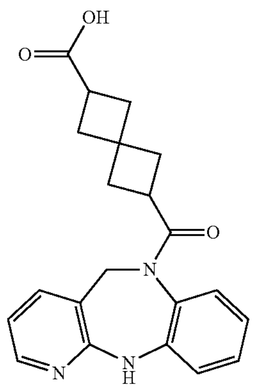 [SMILES: O=C(O)C1CC2(C1)CC(C(=O)N1Cc3cccnc3Nc3ccccc31)C2] | 6-(5,11-dihydro-6H-pyrido[2,3-b][1,5]benzodiazepin-6-ylcarbonyl)spiro[3.3]heptane-2-carboxylic acid | 364 |
| 10 | 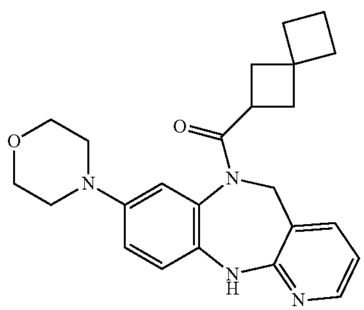 [SMILES: O=C(C1CC2(CCC2)C1)N1Cc2cccnc2Nc2ccc(N3CCOCC3)cc21] | 8-morpholin-4-yl-6-(spiro[3.3]hept-2-ylcarbonyl)-6,11-dihydro-5H-pyrido[2,3-b][1,5]benzodiazepine | 405 |
| 11 | 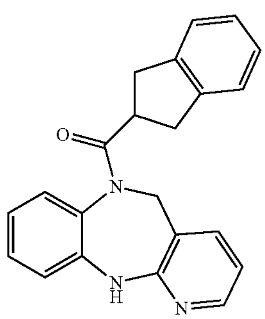 [SMILES: O=C(C1Cc2ccccc2C1)N1Cc2cccnc2Nc2ccccc21] | 6-(2,3-dihydro-1H-inden-2-ylcarbonyl)-6,11-dihydro-5H-pyrido[2,3-b][1,5]benzodiazepine | 342 |
| 12 | 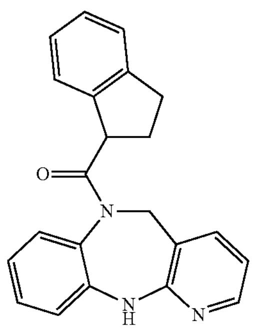 [SMILES: O=C(C1CCc2ccccc21)N1Cc2cccnc2Nc2ccccc21] | 6-(2,3-dihydro-1H-inden-1-ylcarbonyl)-6,11-dihydro-5H-pyrido[2,3-b][1,5]benzodiazepine | 342 |

-continued

| Ex. No. | Structure | Chemical Name | [M + H]+ |
|---|---|---|---|
| 13 | 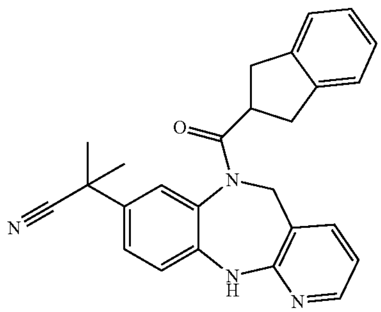 [SMILES: CC(C)(C#N)c1ccc2c(c1)N(C(=O)C1Cc3ccccc3C1)Cc1cccnc1N2] | 2-[6-(2,3-dihydro-1H-inden-2-ylcarbonyl)-6,11-dihydro-5H-pyrido[2,3-b][1,5]benzodiazepin-8-yl]-2-methylpropanenitrile | 409 |
| 14 | 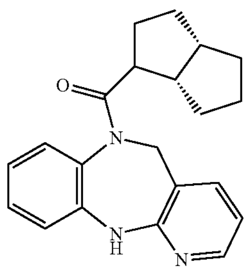 | 6-[(3aS,6aS)-octahydropentalen-1-ylcarbonyl]-6,11-dihydro-5H-pyrido[2,3-b][1,5]benzodiazepine | 334 |
| 15 | 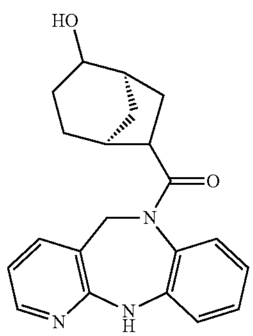 [SMILES: O=C(C1C[C@H]2C[C@@H]1CCC2O)N1Cc2cccnc2Nc2ccccc21] | (1R,5S)-6-(5,11-dihydro-6H-pyrido[2,3-b][1,5]benzodiazepin-6-ylcarbonyl)bicyclo[3.2.1]octan-2-ol | 350 |
| 16 | 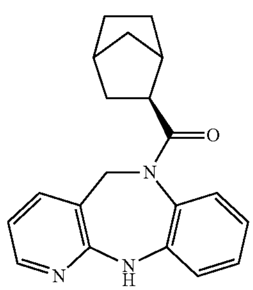 [SMILES: O=C([C@H]1CC2CCC1C2)N1Cc2cccnc2Nc2ccccc21] | 6-[(2S)-bicyclo[2.2.1]hept-2-ylcarbonyl]-6,11-dihydro-5H-pyrido[2,3-b][1,5]benzodiazepine | 320 |
| 17 | 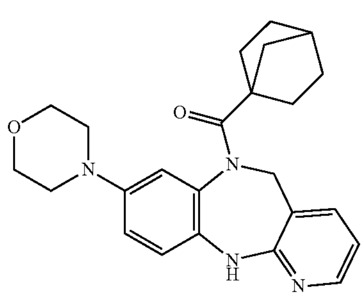 [SMILES: O=C(N1Cc2cccnc2Nc2ccc(N3CCOCC3)cc21)C12CCC(CC1)C2] | 6-(bicyclo[2.2.1]hept-1-ylcarbonyl)-8-morpholin-4-yl-6,11-dihydro-5H-pyrido[2,3-b][1,5]benzodiazepine | 405 |

| Ex. No. | Structure | Chemical Name | [M + H]+ |
|---|---|---|---|
| 18 | 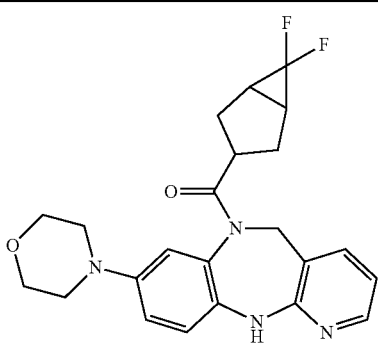 Racemic | 6-[(6,6-difluorobicyclo[3.1.0]hex-3-yl)carbonyl]-8-morpholin-4-yl-6,11-dihydro-5H-pyrido[2,3-b][1,5]benzodiazepine | 427 |
| 19 | 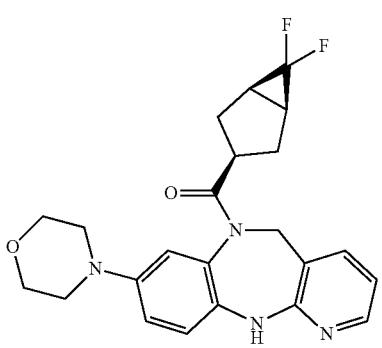 Isomer 1 | 6-{[(1R,3r,5S)-6,6-difluorobicyclo[3.1.0]hex-3-yl]carbonyl}-8-morpholin-4-yl-6,11-dihydro-5H-pyrido[2,3-b][1,5]benzodiazepine | 427 |
| 20 | 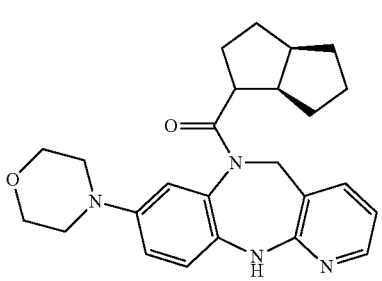 Racemic | 8-morpholin-4-yl-6-[(3aR,6aR)-octahydropentalen-1-ylcarbonyl]-6,11-dihydro-5H-pyrido[2,3-b][1,5]benzodiazepine | 419 |
| 21 | 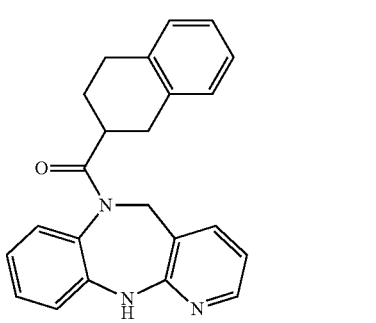 [SMILES: O=C(C1CCc2ccccc2C1)N1Cc2cccnc2Nc2ccccc21] | 6-(1,2,3,4-tetrahydronaphthalen-2-ylcarbonyl)-6,11-dihydro-5H-pyrido[2,3-b][1,5]benzodiazepine | 356 |

| Ex. No. | Structure | Chemical Name | [M + H]+ |
| --- | --- | --- | --- |
| 22 | 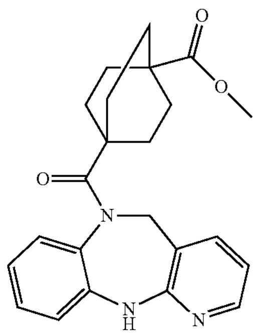 [SMILES: COC(=O)C12CCC(C(=O)N3Cc4cccnc4Nc4ccccc43)(CC1)CC2] | methyl 4-(5,11-dihydro-6H-pyrido[2,3-b][1,5]benzodiazepin-6-ylcarbonyl)bicyclo[2.2.2]octane-1-carboxylate | 392 |
| 23 | 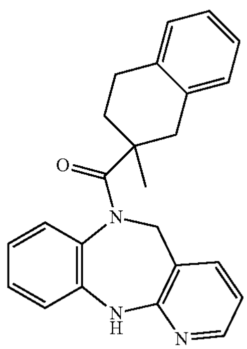 [SMILES: CC1(C(=O)N2Cc3cccnc3Nc3ccccc32)CCc2ccccc2C1] | 6-[(2-methyl-1,2,3,4-tetrahydronaphthalen-2-yl)carbonyl]-6,11-dihydro-5H-pyrido[2,3-b][1,5]benzodiazepine | 370 |
| 24 | 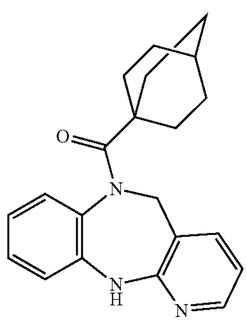 [SMILES: O=C(N1Cc2cccnc2Nc2ccccc21)C12CCC(CC1)CC2] | 6-(bicyclo[2.2.2]oct-1-ylcarbonyl)-6,11-dihydro-5H-pyrido[2,3-b][1,5]benzodiazepine | 334 |
| 25 | 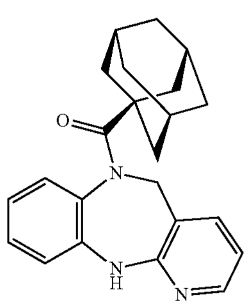 [SMILES: O=C(N1Cc2cccnc2Nc2ccccc21)[C@]12C[C@H]3C[C@H](C[C@H](C3)C1)C2] | 6-[(3s,5s,7s)-tricyclo[3.3.1.1~3,7~]dec-1-ylcarbonyl]-6,11-dihydro-5H-pyrido[2,3-b][1,5]benzodiazepine | 360 |

-continued

| Ex. No. | Structure | Chemical Name | [M + H]+ |
| --- | --- | --- | --- |
| 26 | 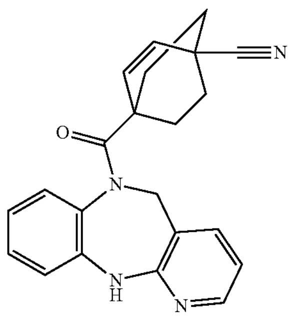 [SMILES: N#CC12C=CC(C(=O)N3Cc4cccnc4Nc4ccccc43)(CC1)CC2] | 4-(5,11-dihydro-6H-pyrido[2,3-b][1,5]benzodiazepin-6-ylcarbonyl)bicyclo[2.2.2]oct-2-ene-1-carbonitrile | 357 |
| 27 | 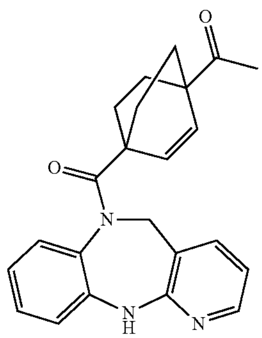 [SMILES: CC(=O)C12C=CC(C(=O)N3Cc4cccnc4Nc4ccccc43)(CC1)CC2] | 1-[4-(5,11-dihydro-6H-pyrido[2,3-b][1,5]benzodiazepin-6-ylcarbonyl)bicyclo[2.2.2]oct-2-en-1-yl]ethanone | 374 |
| 28 | 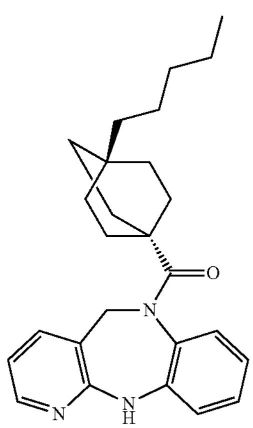 [SMILES: CCCCC[C@]12CC[C@](C(=O)N3Cc4cccnc4Nc4ccccc43)(CC1)CC2] | 6-[(4-pentylbicyclo[2.2.2]oct-1-yl)carbonyl]-6,11-dihydro-5H-pyrido[2,3-b][1,5]benzodiazepine | 404 |
| 29 | 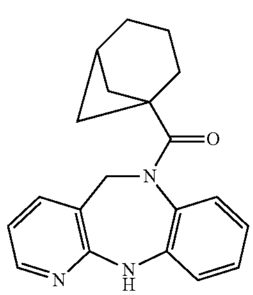 [SMILES: O=C(N1Cc2cccnc2Nc2ccccc21)C12CCCC(C1)C2] | 6-(bicyclo[3.1.1]hept-1-ylcarbonyl)-6,11-dihydro-5H-pyrido[2,3-b][1,5]benzodiazepine | 320 |

| Ex. No. | Structure | Chemical Name | [M + H]+ |
| --- | --- | --- | --- |
| 30 | 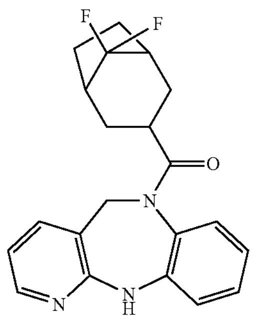 [SMILES: O=C(C1CC2CCC(C1)C2(F)F)N1Cc2cccnc2Nc2ccccc21] | 6-[(8,8-difluorobicyclo[3.2.1]oct-3-yl)carbonyl]-6,11-dihydro-5H-pyrido[2,3-b][1,5]benzodiazepine | 370 |
| 31 | 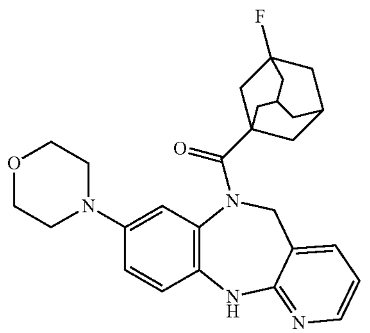 [SMILES: O=C(N1Cc2cccnc2Nc2ccc(N3CCOCC3)cc21)C12CC3CC(CC(F)(C3)C1)C2] | 6-[(3-fluorotricyclo[3.3.1.1~3,7~]dec-1-yl)carbonyl]-8-morpholin-4-yl-6,11-dihydro-5H-pyrido[2,3-b][1,5]benzodiazepine | 463 |
| 32 | 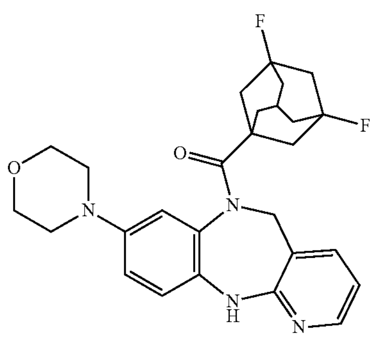 [SMILES: O=C(N1Cc2cccnc2Nc2ccc(N3CCOCC3)cc21)C12CC3CC(F)(CC(F)(C3)C1)C2] | 6-[(3,5-difluorotricyclo[3.3.1.1~3,7~]dec-1-yl)carbonyl]-8-morpholin-4-yl-6,11-dihydro-5H-pyrido[2,3-b][1,5]benzodiazepine | 481 |
| 33 | 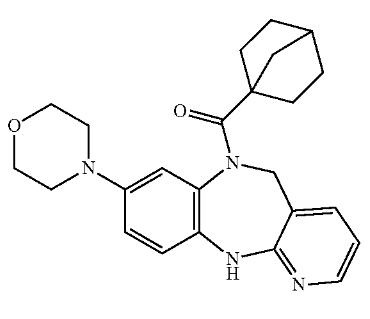 [SMILES: O=C(N1Cc2cccnc2Nc2ccc(N3CCOCC3)cc21)C12CCC(CC1)C2] | 6-(bicyclo[2.2.1]hept-1-ylcarbonyl)-8-morpholin-4-yl-6,11-dihydro-5H-pyrido[2,3-b][1,5]benzodiazepine | 405 |

| Ex. No. | Structure | Chemical Name | [M + H]+ |
|---|---|---|---|
| 34 | Isomer 1 | 8-morpholin-4-yl-6-[(3aS,5R,7aS)-octahydro-1-benzofuran-5-ylcarbonyl]-6,11-dihydro-5H-pyrido[2,3-b][1,5]benzodiazepine | 435 |
| 35 | Isomer 2 | 8-morpholin-4-yl-6-[(3aR,5S,7aR)-octahydro-1-benzofuran-5-ylcarbonyl]-6,11-dihydro-5H-pyrido[2,3-b][1,5]benzodiazepine | 435 |
| 36 | Isomer 3 | 8-morpholin-4-yl-6-[(3aS,5R,7aS)-octahydro-1-benzofuran-5-ylcarbonyl]-6,11-dihydro-5H-pyrido[2,3-b][1,5]benzodiazepine | 435 |
| 37 | Isomer 4 | 8-morpholin-4-yl-6-[(3aR,5S,7aR)-octahydro-1-benzofuran-5-ylcarbonyl]-6,11-dihydro-5H-pyrido[2,3-b][1,5]benzodiazepine | 435 |

| Ex. No. | Structure | Chemical Name | [M + H]+ |
|---|---|---|---|
| 38 | And enantiomer | 8-morpholin-4-yl-6-[(4aR,6S,8aS)-octahydro-2H-chromen-6-ylcarbonyl]-6,11-dihydro-5H-pyrido[2,3-b][1,5]benzodiazepine | 449 |
| 39 | And enantiomer | 8-morpholin-4-yl-6-[(4aR,6R,8aS)-octahydro-2H-chromen-6-ylcarbonyl]-6,11-dihydro-5H-pyrido[2,3-b][1,5]benzodiazepine | 449 |
| 40 | 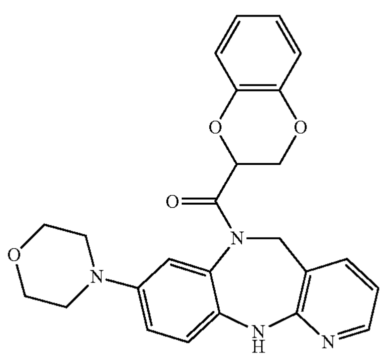 | 6-(2,3-dihydro-1,4-benzodioxin-2-ylcarbonyl)-8-morpholin-4-yl-6,11-dihydro-5H-pyrido[2,3-b][1,5]benzodiazepine | 445 |
| 41 | 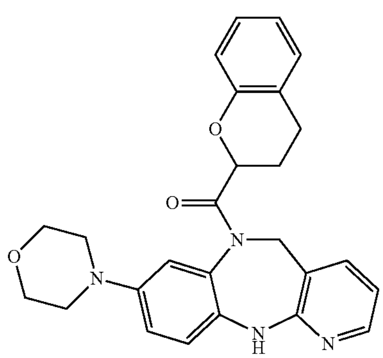 [SMILES: O=C(C1CCc2ccccc2O1)N1Cc2cccnc2Nc2ccc(N3CCOCC3)cc21] | 6-(3,4-dihydro-2H-chromen-2-ylcarbonyl)-8-morpholin-4-yl-6,11-dihydro-5H-pyrido[2,3-b][1,5]benzodiazepine | 443 |

| Ex. No. | Structure | Chemical Name | [M + H]+ |
|---|---|---|---|
| 42 | 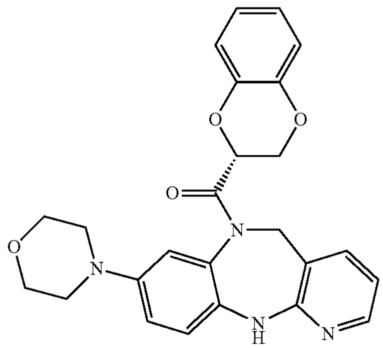 | 6-[(2R)-2,3-dihydro-1,4-benzodioxin-2-ylcarbonyl]-8-morpholin-4-yl-6,11-dihydro-5H-pyrido[2,3-b][1,5]benzodiazepine | 445 |
| 43 | 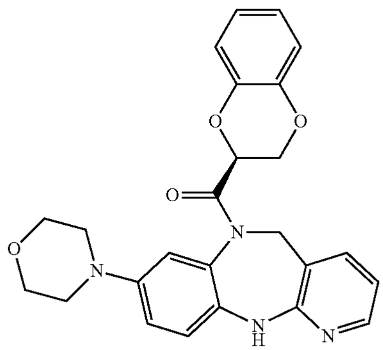 [SMILES: O=C([C@@H]1COc2ccccc2O1)N1Cc2cccnc2Nc2ccc(N3CCOCC3)cc21] | 6-[(2S)-2,3-dihydro-1,4-benzodioxin-2-ylcarbonyl]-8-morpholin-4-yl-6,11-dihydro-5H-pyrido[2,3-b][1,5]benzodiazepine | 445 |
| 44 | 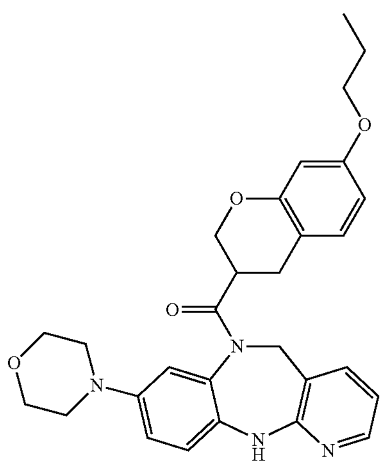 [SMILES: CCCOc1ccc2c(c1)OCC(C(=O)N1Cc3cccnc3Nc3ccc(N4CCOCC4)cc31)C2] | 8-morpholin-4-yl-6-[(7-propoxy-3,4-dihydro-2H-chromen-3-yl)carbonyl]-6,11-dihydro-5H-pyrido[2,3-b][1,5]benzodiazepine | 501 |
| 45 | Isomer 1 | 8-morpholin-4-yl-6-[(4aR,6S,8aS)-octahydro-2H-chromen-6-ylcarbonyl]-6,11-dihydro-5H-pyrido[2,3-b][1,5]benzodiazepine | 449 |

-continued

| Ex. No. | Structure | Chemical Name | [M + H]+ |
| --- | --- | --- | --- |
| 46 | Isomer 2 | 8-morpholin-4-yl-6-[(4aS,6R,8aR)-octahydro-2H-chromen-6-ylcarbonyl]-6,11-dihydro-5H-pyrido[2,3-b][1,5]benzodiazepine | 449 |
| 47 | Isomer 3 | 8-morpholin-4-yl-6-[(4aS,6S,8aS)-octahydro-2H-chromen-6-ylcarbonyl]-6,11-dihydro-5H-pyrido[2,3-b][1,5]benzodiazepine | 449 |
| 48 | Isomer 4 | 8-morpholin-4-yl-6-[(4aR,6R,8aR)-octahydro-2H-chromen-6-ylcarbonyl]-6,11-dihydro-5H-pyrido[2,3-b][1,5]benzodiazepine | 449 |
| 49 | Isomer 5 | 8-morpholin-4-yl-6-[(4aS,6R,8aS)-octahydro-2H-chromen-6-ylcarbonyl]-6,11-dihydro-5H-pyrido[2,3-b][1,5]benzodiazepine | 449 |

| Ex. No. | Structure | Chemical Name | [M + H]+ |
|---|---|---|---|
| 50 | Isomer 6 | 8-morpholin-4-yl-6-[(4aR,6S,8aR)-octahydro-2H-chromen-6-ylcarbonyl]-6,11-dihydro-5H-pyrido[2,3-b][1,5]benzodiazepine | 449 |
| 51 | Isomer 7 | 8-morpholin-4-yl-6-[(4aR,6R,8aS)-octahydro-2H-chromen-6-ylcarbonyl]-6,11-dihydro-5H-pyrido[2,3-b][1,5]benzodiazepine | 449 |
| 52 | Isomer 8 | 8-morpholin-4-yl-6-[(4aS,6S,8aR)-octahydro-2H-chromen-6-ylcarbonyl]-6,11-dihydro-5H-pyrido[2,3-b][1,5]benzodiazepine | 449 |
| 53 | Isomer 1 | 6-{[(2R,3aS,5R,7aS)-2-methyloctahydro-1-benzofuran-5-yl]carbonyl}-8-morpholin-4-yl-6,11-dihydro-5H-pyrido[2,3-b][1,5]benzodiazepine | 449 |

| Ex. No. | Structure | Chemical Name | [M + H]+ |
|---|---|---|---|
| 54 | Isomer 2 | 6-{[(2S,3aR,5S,7aR)-2-methyloctahydro-1-benzofuran-5-yl]carbonyl}-8-morpholin-4-yl-6,11-dihydro-5H-pyrido[2,3-b][1,5]benzodiazepine | 449 |
| 55 | Isomer 3 | 6-{[(2R,3aS,5R,7aS)-2-methyloctahydro-1-benzofuran-5-yl]carbonyl}-8-morpholin-4-yl-6,11-dihydro-5H-pyrido[2,3-b][1,5]benzodiazepine | 449 |
| 56 | Isomer 4 | 6-{[(2S,3aR,5S,7aR)-2-methyloctahydro-1-benzofuran-5-yl]carbonyl}-8-morpholin-4-yl-6,11-dihydro-5H-pyrido[2,3-b][1,5]benzodiazepine | 449 |
| 57 | 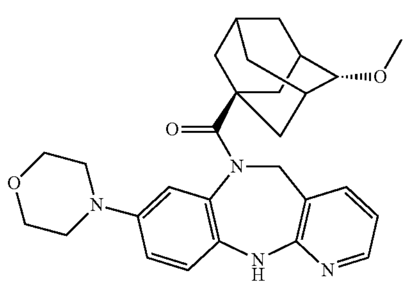 [SMILES: CO[C@H]1C2CC3CC1C[C@](C(=O)N1Cc4cccnc4Nc4ccc(N5CCOCC5)cc41)(C3)C2] | 6-{[(1r,4s)-4-methoxytricyclo[3.3.1.1~3,7~]dec-1-yl]carbonyl}-8-morpholin-4-yl-6,11-dihydro-5H-pyrido[2,3-b][1,5]benzodiazepine | 475 |

| Ex. No. | Structure | Chemical Name | [M + H]+ |
|---|---|---|---|
| 58 | 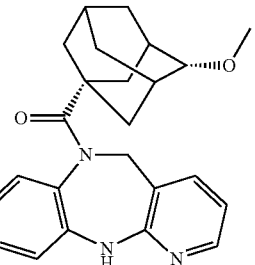 | 6-{[(1s,4r)-4-methoxytricyclo[3.3.1.1~3,7~]dec-1-yl]carbonyl}-8-morpholin-4-yl-6,11-dihydro-5H-pyrido[2,3-b][1,5]benzodiazepine | 475 |
| 59 | 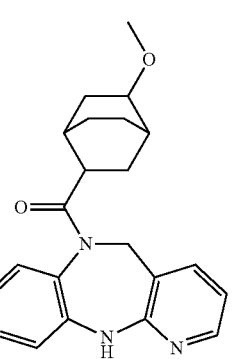<br>Isomer 1 | 6-[(5-methoxybicyclo[2.2.2]oct-2-yl)carbonyl]-8-morpholin-4-yl-6,11-dihydro-5H-pyrido[2,3-b][1,5]benzodiazepine | 449 |
| 60 | 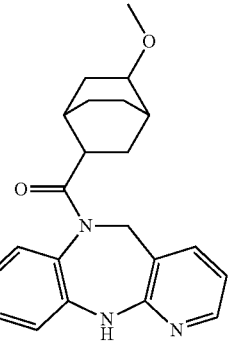<br>Isomer 2 | 6-[(5-methoxybicyclo[2.2.2]oct-2-yl)carbonyl]-8-morpholin-4-yl-6,11-dihydro-5H-pyrido[2,3-b][1,5]benzodiazepine | 449 |
| 61 | 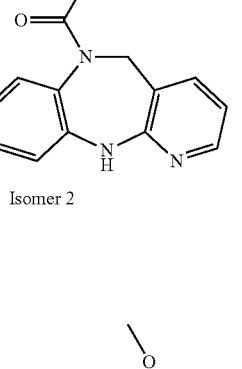<br>Isomer 3 | 6-[(5-methoxybicyclo[2.2.2]oct-2-yl)carbonyl]-8-morpholin-4-yl-6,11-dihydro-5H-pyrido[2,3-b][1,5]benzodiazepine | 449 |

| Ex. No. | Structure | Chemical Name | [M + H]+ |
|---|---|---|---|
| 62 | 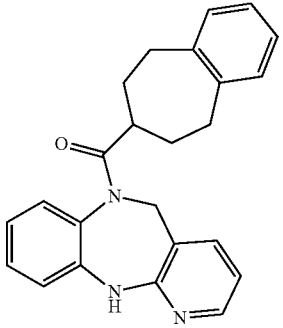 [SMILES: O=C(C1CCc2ccccc2CC1)N1Cc2cccnc2Nc2ccccc21] | 6-(6,7,8,9-tetrahydro-5H-benzo[7]annulen-7-ylcarbonyl)-6,11-dihydro-5H-pyrido[2,3-b][1,5]benzodiazepine | 370 |
| 63 | 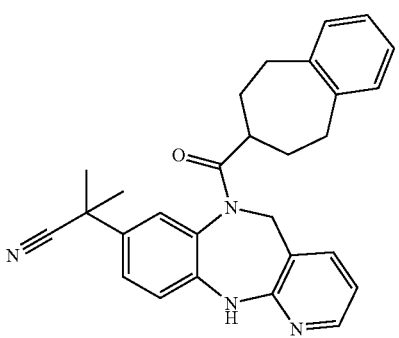 [SMILES: CC(C)(C#N)c1ccc2c(c1)N(C(=O)C1CCc3ccccc3CC1)Cc1cccnc1N2] | 2-methyl-2-[6-(6,7,8,9-tetrahydro-5H-benzo[7]annulen-7-ylcarbonyl)-6,11-dihydro-5H-pyrido[2,3-b][1,5]benzodiazepin-8-yl]propanenitrile | 437 |
| 64 | 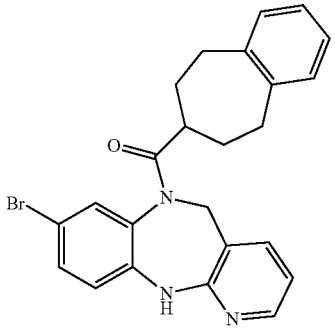 | 8-bromo-6-(6,7,8,9-tetrahydro-5H-benzo[7]annulen-7-ylcarbonyl)-6,11-dihydro-5H-pyrido[2,3-b][1,5]benzodiazepine | 448 |
| 65 | 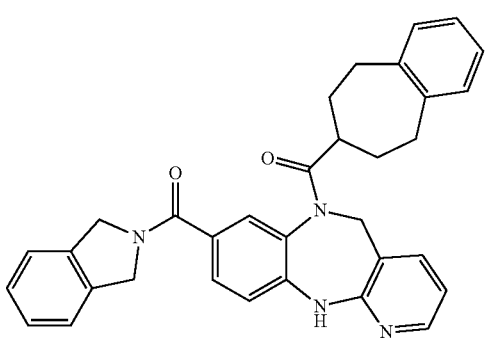 [SMILES: O=C(c1ccc2c(c1)N(C(=O)C1CCc3ccccc3CC1)Cc1cccnc1N2)N1Cc2ccccc2C1] | 8-(1,3-dihydro-2H-isoindol-2-ylcarbonyl)-6-(6,7,8,9-tetrahydro-5H-benzo[7]annulen-7-ylcarbonyl)-6,11-dihydro-5H-pyrido[2,3-b][1,5]benzodiazepine | 515 |
| 66 | 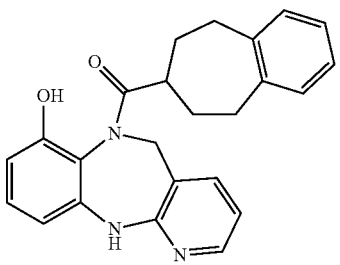 [SMILES: O=C(C1CCc2ccccc2CC1)N1Cc2cccnc2Nc2cccc(O)c21] | 6-(6,7,8,9-tetrahydro-5H-benzo[7]annulen-7-ylcarbonyl)-6,11-dihydro-5H-pyrido[2,3-b][1,5]benzodiazepin-7-ol | 386 |

| Ex. No. | Structure | Chemical Name | [M + H]+ |
| --- | --- | --- | --- |
| 67 | 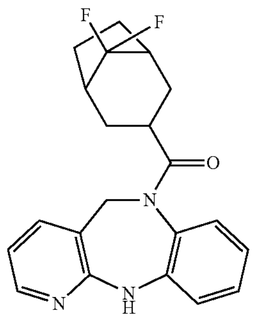 [SMILES: O=C(C1CC2CCC(C1)C2(F)F)N1Cc2cccnc2Nc2ccccc21] | 6-[(8,8-difluorobicyclo[3.2.1]oct-3-yl)carbonyl]-6,11-dihydro-5H-pyrido[2,3-b][1,5]benzodiazepine | 370 |
| 68 | 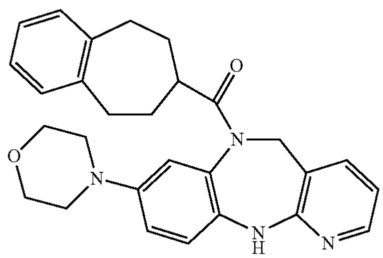 [SMILES: O=C(C1CCc2ccccc2CC1)N1Cc2cccnc2Nc2ccc(N3CCOCC3)cc21] | 8-morpholin-4-yl-6-(6,7,8,9-tetrahydro-5H-benzo[7]annulen-7-ylcarbonyl)-6,11-dihydro-5H-pyrido[2,3-b][1,5]benzodiazepine | 455 |
| 69 | 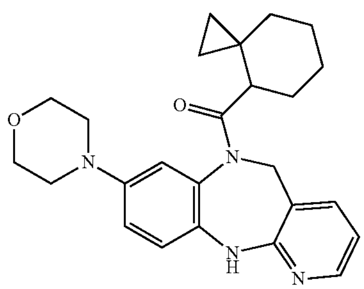 [SMILES: O=C(C1CCCCC12CC2)N1Cc2cccnc2Nc2ccc(N3CCOCC3)cc21] | 8-morpholin-4-yl-6-(spiro[2.5]oct-4-ylcarbonyl)-6,11-dihydro-5H-pyrido[2,3-b][1,5]benzodiazepine | 419 |
| 70 | 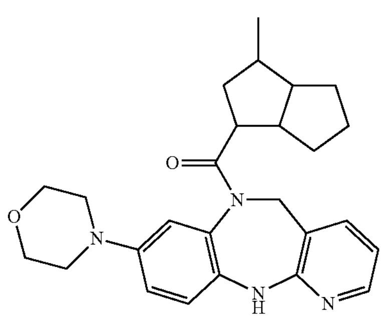 [SMILES: CC1CC(C(=O)N2Cc3cccnc3Nc3ccc(N4CCOCC4)cc32)C2CCCC12] | 6-[(3-methyloctahydropentalen-1-yl)carbonyl]-8-morpholin-4-yl-6,11-dihydro-5H-pyrido[2,3-b][1,5]benzodiazepine | 433 |
| 71 | 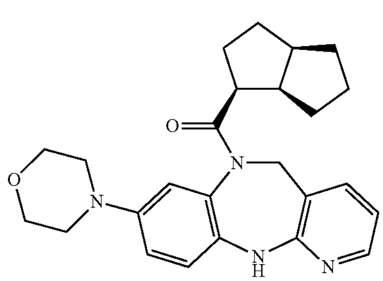 | 8-morpholin-4-yl-6-[(1S,3aR,6aR)-octahydropentalen-1-ylcarbonyl]-6,11-dihydro-5H-pyrido[2,3-b][1,5]benzodiazepine Isomer 1 | 419 |

| Ex. No. | Structure | Chemical Name | [M + H]+ |
|---|---|---|---|
| 72 | 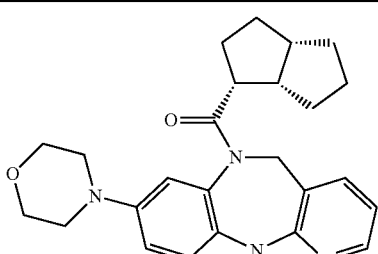 Isomer 2 | 8-morpholin-4-yl-6-[(1R,3aS,6aS)-octahydropentalen-1-ylcarbonyl]-6,11-dihydro-5H-pyrido[2,3-b][1,5]benzodiazepine | 419 |
| 73 | 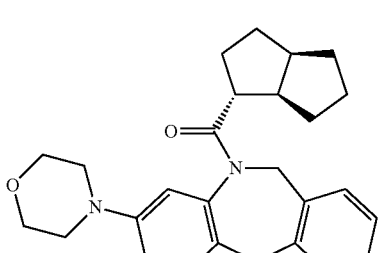 Isomer 3 | 8-morpholin-4-yl-6-[(1R,3aR,6aR)-octahydropentalen-1-ylcarbonyl]-6,11-dihydro-5H-pyrido[2,3-b][1,5]benzodiazepine | 419 |
| 74 | 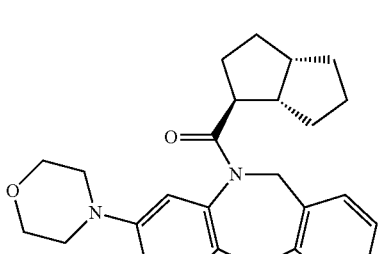 Isomer 4 | 8-morpholin-4-yl-6-[(1S,3aS,6aS)-octahydropentalen-1-ylcarbonyl]-6,11-dihydro-5H-pyrido[2,3-b][1,5]benzodiazepine | 419 |
| 75 | 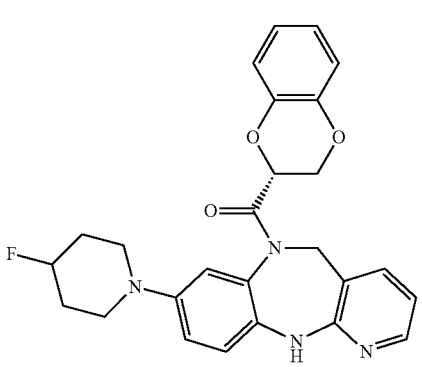 [SMILES: O=C([C@H]1COc2ccccc2O1)N1Cc2cccnc2Nc2ccc(N3CCC(F)CC3)cc21] | 6-[(2R)-2,3-dihydro-1,4-benzodioxin-2-ylcarbonyl]-8-(4-fluoropiperidin-1-yl)-6,11-dihydro-5H-pyrido[2,3-b][1,5]benzodiazepine | 461 |

| Ex. No. | Structure | Chemical Name | [M + H]+ |
|---|---|---|---|
| 76 | 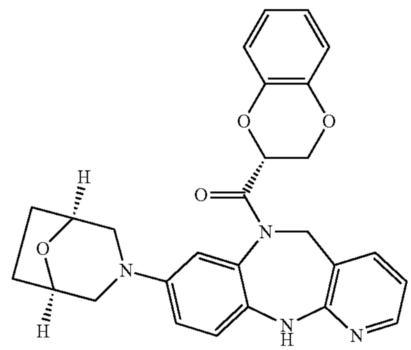 [SMILES: O=C([C@H]1COc2ccccc2O1)N1Cc2cccnc2Nc2ccc(N3C[C@H]4CC[C@@H](C3)O4)cc21] | 6-[(2R)-2,3-dihydro-1,4-benzodioxin-2-ylcarbonyl]-8-[(1R,5S)-8-oxa-3-azabicyclo[3.2.1]oct-3-yl]-6,11-dihydro-5H-pyrido[2,3-b][1,5]benzodiazepine | 471 |
| 77 | Isomer 1, racemic | 6-{[(1R,3aS,4S,6aS)-4-ethoxyoctahydropentalen-1-yl]carbonyl}-8-morpholin-4-yl-6,11-dihydro-5H-pyrido[2,3-b][1,5]benzodiazepine | 463 |
| 78 | Isomer 2, racemic | 6-{[(1R,3aS,4R,6aS)-4-ethoxyoctahydropentalen-1-yl]carbonyl}-8-morpholin-4-yl-6,11-dihydro-5H-pyrido[2,3-b][1,5]benzodiazepine | 463 |
| 79 | 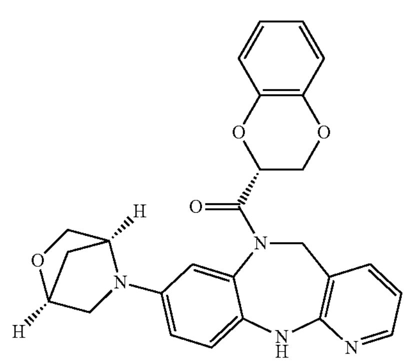 [SMILES: O=C([C@H]1COc2ccccc2O1)N1Cc2cccnc2Nc2ccc(N3C[C@@H]4C[C@H]3CO4)cc21] | 6-[(2R)-2,3-dihydro-1,4-benzodioxin-2-ylcarbonyl]-8-[(1S,4S)-2-oxa-5-azabicyclo[2.2.1]hept-5-yl]-6,11-dihydro-5H-pyrido[2,3-b][1,5]benzodiazepine | 457 |

| Ex. No. | Structure | Chemical Name | [M + H]+ |
|---|---|---|---|
| 80 | 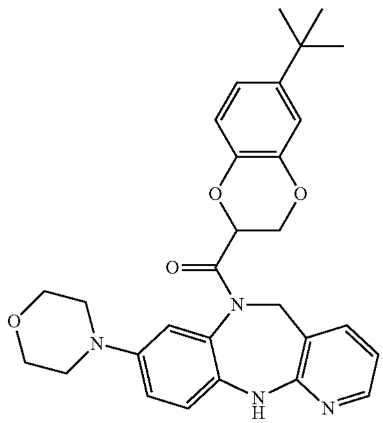 [SMILES: CC(C)(C)c1ccc2c(c1)OCC(C(=O)N1Cc3cccnc3Nc3ccc(N4CCOCC4)cc31)O2] | 6-[(6-tert-butyl-2,3-dihydro-1,4-benzodioxin-2-yl)carbonyl]-8-morpholin-4-yl-6,11-dihydro-5H-pyrido[2,3-b][1,5]benzodiazepine | 501 |
| 81 | 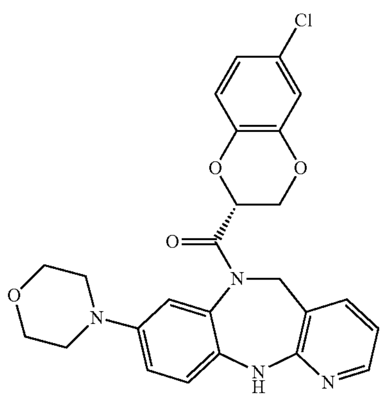 [SMILES: O=C([C@H]1COc2cc(Cl)ccc2O1)N1Cc2cccnc2Nc2ccc(N3CCOCC3)cc21] | 6-{[(2R)-6-chloro-2,3-dihydro-1,4-benzodioxin-2-yl]carbonyl}-8-morpholin-4-yl-6,11-dihydro-5H-pyrido[2,3-b][1,5]benzodiazepine | 479 |
| 82 | Enantiopure | 6-(octahydro-1,4-benzodioxin-2-ylcarbonyl)-8-(8-oxa-3-azabicyclo[3.2.1]oct-3-yl)-6,11-dihydro-5H-pyrido[2,3-b][1,5]benzodiazepine | 477 |

| Ex. No. | Structure | Chemical Name | [M + H]+ |
|---|---|---|---|
| 83 | 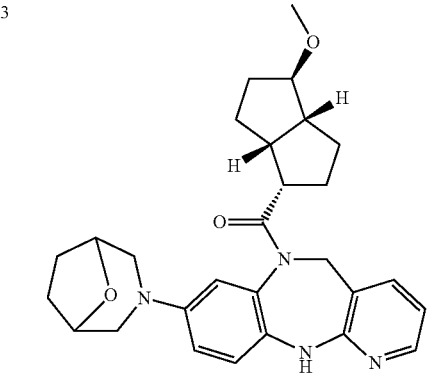 Isomer 1 | 6-{[(1S,3aR,4R,6aR)-4-methoxyoctahydropentalen-1-yl]carbonyl}-8-(8-oxa-3-azabicyclo[3.2.1]oct-3-yl)-6,11-dihydro-5H-pyrido[2,3-b][1,5]benzodiazepine | 475 |
| 84 | 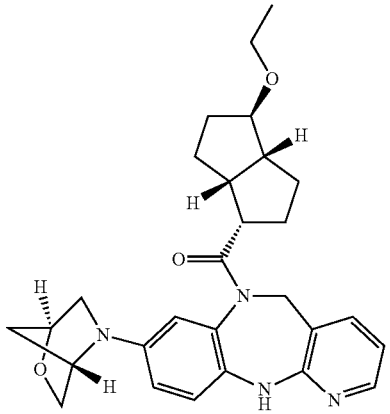 Isomer 1 | 6-{[(1S,3aR,4R,6aR)-4-ethoxyoctahydropentalen-1-yl]carbonyl}-8-[(1S,4S)-2-oxa-5-azabicyclo[2.2.1]hept-5-yl]-6,11-dihydro-5H-pyrido[2,3-b][1,5]benzodiazepine | 475 |
| 85 | 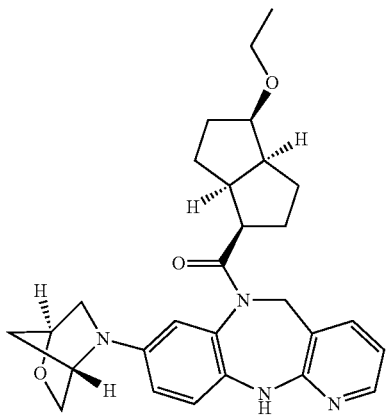 Isomer 2, racemic | 6-{[(1R,3aS,4R,6aS)-4-ethoxyoctahydropentalen-1-yl]carbonyl}-8-[(1S,4S)-2-oxa-5-azabicyclo[2.2.1]hept-5-yl]-6,11-dihydro-5H-pyrido[2,3-b][1,5]benzodiazepine | 475 |

Example 86

6-[(6-Methoxyspiro[3.3]hept-2-yl)carbonyl]-8-morpholin-4-yl-6,11-dihydro-5Hpyrido[2,3-b][1,5]benzodiazepine

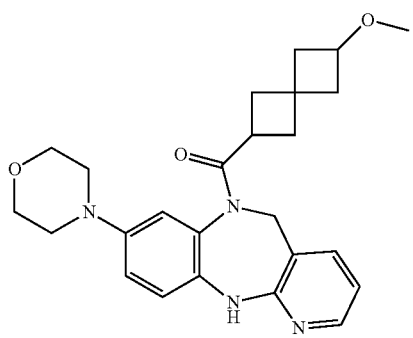 [SMILES: COC1CC2(C1)CC(C(=O)N1Cc3cccnc3Nc3ccc(N4CCOCC4)cc31)C2]

To a mixture of methoxytrimethylsilane (10 mg, 0.096 mmol) in DCM (0.96 mL) at −78° C. was added tert-butyl 8-morpholino-6-(6-oxospiro[3.3]heptane-2-carbonyl)-5H-benzo[b]pyrido[2,3-e][1,4]diazepine-11 (6H)-carboxylate (50 mg, 0.096 mmol). Trimethylsilyl trifluoromethanesulfonate (26 μL, 0.14 mmol) was added, and the mixture was stirred for 1 h at −78° C. Triethylsilane (17 μL, 0.11 mmol) was added, the cooling bath was removed and the mixture was warmed to room temperature and stirred for 16 h. The mixture was then quenched with saturated aqueous sodium bicarbonate and extracted with DCM. The organic layer was dried over sodium sulfate, filtered, and concentrated under reduced pressure. The mixture was purified by reverse phase HPLC (ACN/water with 0.1% TFA modifier) to afford 6-[(6-methoxyspiro[3.3]hept-2-yl)carbonyl]-8-morpholin-4-yl-6,11-dihydro-5H-pyrido[2,3-b][1,5]benzodiazepine as the TFA salt. MS: 435 (M+1). $^1$H NMR (600 MHz, DMSO-$d_6$) δ 9.86 (s, 1H), 8.02 (d, J=5.3 Hz, 1H), 7.69 (d, J=7.3 Hz, 1H), 7.16 (d, J=8.9 Hz, 1H), 6.96-6.92 (m, 1H), 6.85-6.72 (m, 2H), 5.20 (d, J=15.0 Hz, 1H), 3.90 (d, J=15.1 Hz, 1H), 3.75-3.68 (m, 4H), 3.63-3.46 (m, 1H), 3.18-3.06 (m, 3H), 3.06-2.99 (m, 2H), 2.97 (s, 3H), 2.24-1.87 (m, 4H), 1.79-1.48 (m, 3H), 1.47-1.30 (m, 1H).

The compounds in the following table were prepared using the methodology herein and the general procedure described in Example 86.

| Ex. No. | Structure | Chemical Name | [M + H]+ |
| --- | --- | --- | --- |
| 87 | 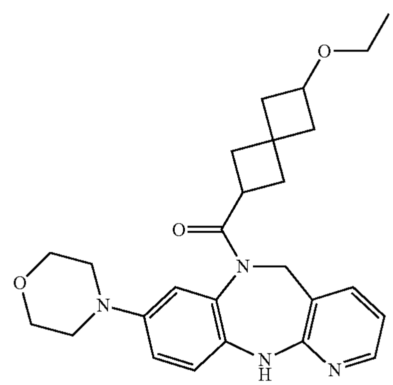 [SMILES: CCOC1CC2(C1)CC(C(=O)N1Cc3cccnc3Nc3ccc(N4CCOCC4)cc31)C2] | 6-[(6-ethoxyspiro[3.3]hept-2-yl)carbonyl]-8-morpholin-4-yl-6,11-dihydro-5H-pyrido[2,3-b][1,5]benzodiazepine | 449 |
| 88 | 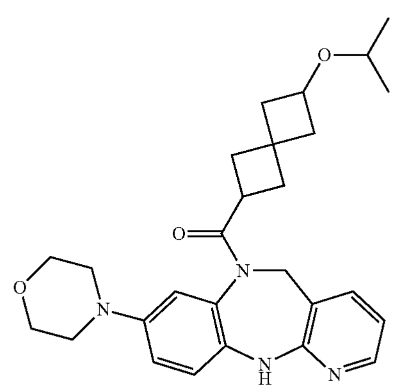 [SMILES: CC(C)OC1CC2(C1)CC(C(=O)N1Cc3cccnc3Nc3ccc(N4CCOCC4)cc31)C2] | 6-{[6-(1-methylethoxy)spiro[3.3]hept-2-yl]carbonyl}-8-morpholin-4-yl-6,11-dihydro-5H-pyrido[2,3-b][1,5]benzodiazepine | 463 |

Example 89

6-({4-[(3-Methylazetidin-1-yl)carbonyl]bicyclo[2.2.2]oct-1-yl}carbonyl)-6,11-dihydro-5H-pyrido[2,3-b][1,5]benzodiazepine

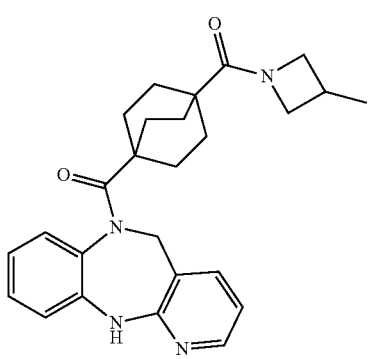 [SMILES: CC1CN(C(=O)C23CCC(C(=O)N4Cc5cccnc5Nc5ccccc54)(CC2)CC3)C1]

To a mixture of 4-(6,11-dihydro-5H-benzo[b]pyrido[2,3-e][1,4]diazepine-6-carbonyl)bicyclo[2.2.2]octane-1-carboxylic acid (15 mg, 0.040 mmol), 2,4,6-tripropyl-1,3,5,2,4,6-trioxatriphosphorinane-2,4,6-trioxide (50 mg, 0.079 mmol) and triethylamine (17 uL, 0.12 mmol) in dichloromethane (0.5 mL) was added to 3-methylazetidin-1-ium chloride (5 mg, 0.05 mmol). The mixture was stirred at room temperature for 18 h and then concentrated under reduced pressure. The residue was diluted with dimethyl sulfoxide (1.8 mL), filtered through an acrodisc filter (0.45 μm) and purified by reverse phase HPLC (CAN/water with 0.1% TFA modifier) to afford 6-({4-[(3-methylazetidin-1-yl)carbonyl]bicyclo[2.2.2]oct-1-yl}carbonyl)-6,11-dihydro-5H-pyrido[2,3-b][1,5]benzodiazepine. MS: 431 (M+1). $^1$H NMR (500 MHz, DMSO-$d_6$): δ 9.36 (s, 1 H); 8.03 (d, J=4.8 Hz, 1 H); 7.44 (d, J=7.3 Hz, 1 H); 7.33 (d, J=8.0 Hz, 1 H); 7.28-7.22 (m, 2 H); 6.95 (t, J=7.4 Hz, 1 H); 6.72 (dd, J=7.3, 4.8 Hz, 1 H); 5.29 (d, J=14.7 Hz, 1 H); 4.30 (s, 1 H); 3.85-3.75 (m, 2 H); 2.55 (s, 1 H); 1.59 (m, 4 H); 1.65-1.35 (m, 6H); 1.39 (m, 4 H); 1.10 (d, J=6.8 Hz, 3 H).

The compounds in the following table were prepared using the methodology herein and the general procedure described in Example 89.

| Ex. No. | Structure | Chemical Name | [M + H]+ |
|---|---|---|---|
| 90 | 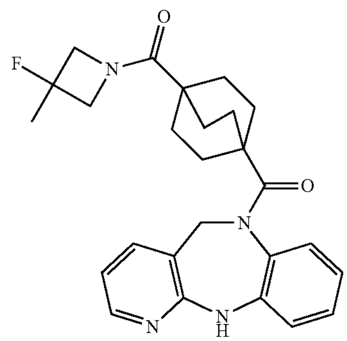 [SMILES: CC1(F)CN(C(=O)C23CCC(C(=O)N4Cc5cccnc5Nc5ccccc54)(CC2)CC3)C1] | 6-({4-[(3-fluoro-3-methylazetidin-1-yl)carbonyl]bicyclo[2.2.2]oct-1-yl}carbonyl)-6,11-dihydro-5H-pyrido[2,3-b][1,5]benzodiazepine | 449 |
| 91 | 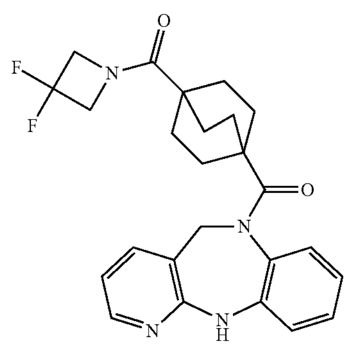 [SMILES: O=C(N1CC(F)(F)C1)C12CCC(C(=O)N3Cc4cccnc4Nc4ccccc43)(CC1)CC2] | 6-({4-[(3,3-difluoroazetidin-1-yl)carbonyl]bicyclo[2.2.2]oct-1-yl}carbonyl)-6,11-dihydro-5H-pyrido[2,3-b][1,5]benzodiazepine | 453 |
| 92 | 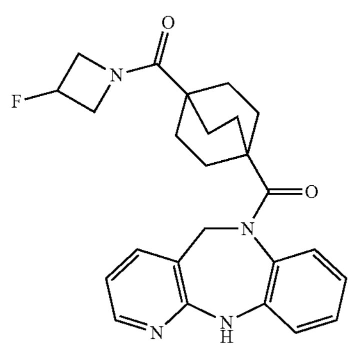 [SMILES: O=C(N1CC(F)C1)C12CCC(C(=O)N3Cc4cccnc4Nc4ccccc43)(CC1)CC2] | 6-({4-[(3-fluoroazetidin-1-yl)carbonyl]bicyclo[2.2.2]oct-1-yl}carbonyl)-6,11-dihydro-5H-pyrido[2,3-b][1,5]benzodiazepine | 435 |

| Ex. No. | Structure | Chemical Name | [M + H]+ |
|---|---|---|---|
| 93 | 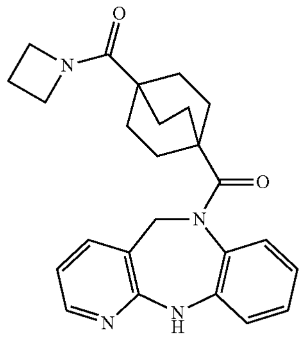 [SMILES: O=C(N1CCC1)C12CCC(C(=O)N3Cc4cccnc4Nc4ccccc43)(CC1)CC2] | 6-{[4-(azetidin-1-ylcarbonyl)bicyclo[2.2.2]oct-1-yl]carbonyl}-6,11-dihydro-5H-pyrido[2,3-b][1,5]benzodiazepine | 417 |
| 94 | 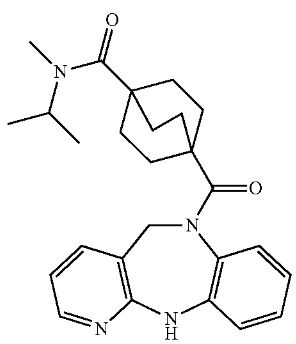 [SMILES: CC(C)N(C)C(=O)C12CCC(C(=O)N3Cc4cccnc4Nc4ccccc43)(CC1)CC2] | 4-(5,11-dihydro-6H-pyrido[2,3-b][1,5]benzodiazepin-6-ylcarbonyl)-N-methyl-N-(1-methylethyl)bicyclo[2.2.2]octane-1-carboxamide | 433 |

Example 95

8-Morpholin-4-yl-6-(1,2,3,4-tetrahydronaphthalen-2-ylcarbonyl)-6,11-dihydro-5H-pyrido[2,3-b][1,5]benzodiazepine

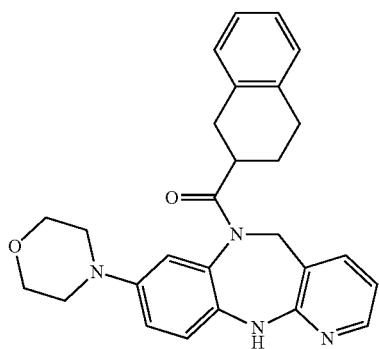

To a vial containing 4-(6,11-dihydro-5H-benzo[b]pyrido[2,3-e][1,4]diazepin-8-yl)morpholine (20 mg, 0.071 mmol) was added 1,2,3,4-tetrahydronaphthalene-2-carboxylic acid (25 mg, 0.14 mmol), HATU (54 mg, 0.14 mmol), anhydrous DMF (1 mL) and DIEA (0.037 ml, 0.21 mmol). The vial was sealed and the reaction was heated to 80° C. for 2 h. Upon cooling to room temperature, the mixture was quenched with water (2 mL) and the resulting mixture was washed with ethyl acetate (2×3 mL). The combined organic layers were concentrated under reduced pressure and the residue was purified by reverse phase HPLC (ACN/water with 0.1% TFA modifier) to afford 8-morpholin-4-yl-6-(1,2,3,4-tetrahydronaphthalen-2-ylcarbonyl)-6,11-dihydro-5H-pyrido[2,3-b][1,5]benzodiazepine as the TFA salt. MS: 441 (M+1). $^1$H NMR (500 MHz, DMSO-$d_6$) δ 9.33 (s, 1H), 8.04-8.03 (m, 1H), 7.53-7.51 (m, 1H), 7.27-7.21 (m, 2H), 7.10 (s, 1H), 7.00 (s, 1H), 6.91-6.85 (m, 2H), 6.78-6.69 (m, 2H), 5.28 (d, J=15.2 Hz, 1H), 4.05-3.92 (m, 1H), 3.74-3.67 (m, 4H), 3.12-2.95 (m, 4H), 2.93-2.83 (m, 2H), 2.82-2.60 (m, 2H), 2.37-2.28 (m, 1H), 2.28-2.12 (m, 2H).

The compounds in the following table were prepared using the methodology herein and the general procedure described in Example 95.

| Ex. No. | Structure | Chemical Name | [M + H]+ |
|---|---|---|---|
| 96 | 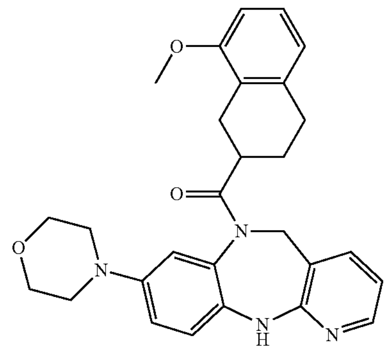 [SMILES: COc1cccc2c1CC(C(=O)N1Cc3cccnc3Nc3ccc(N4CCOCC4)cc31)CC2] | 6-[(8-methoxy-1,2,3,4-tetrahydronaphthalen-2-yl)carbonyl]-8-morpholin-4-yl-6,11-dihydro-5H-pyrido[2,3-b][1,5]benzodiazepine | 471 |
| 97 | 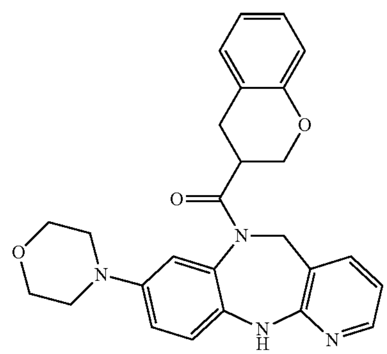 [SMILES: O=C(C1COc2ccccc2C1)N1Cc2cccnc2Nc2ccc(N3CCOCC3)cc21] | 6-(3,4-dihydro-2H-chromen-3-ylcarbonyl)-8-morpholin-4-yl-6,11-dihydro-5H-pyrido[2,3-b][1,5]benzodiazepine | 443 |
| 98 | 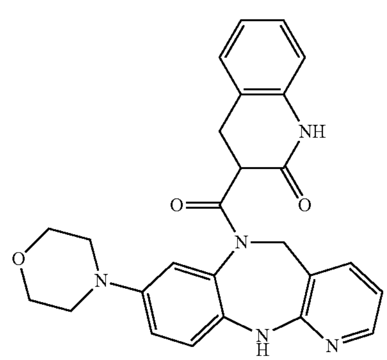 [SMILES: O=C1Nc2ccccc2CC1C(=O)N1Cc2cccnc2Nc2ccc(N3CCOCC3)cc21] | 3-[(8-morpholin-4-yl-5,11-dihydro-6H-pyrido[2,3-b][1,5]benzodiazepin-6-yl)carbonyl]-3,4-dihydroquinolin-2(1H)-one | 456 |

Example 99

8-(1-Methyl-1H-pyrazol-4-yl)-6-(6,7,8,9-tetrahydro-5H-benzo[7]annulen-7-ylcarbonyl)-6,11-dihydro-5H-pyrido[2,3-b][1,5]benzodiazepine

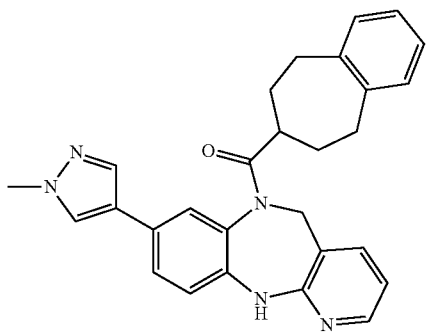 [SMILES: Cn1cc(-c2ccc3c(c2)N(C(=O)C2CCc4ccccc4CC2)Cc2cccnc2N3)cn1]

To a mixture of 1-methyl-4-(4,4,5,5-tetramethyl-1,3,2-dioxaborolan-2-yl)-1H-pyrazole (17 mg, 0.080 mmol) and PdCl$_2$(dppf) (5 mg, 7 µmol) was added a mixture of (8-bromo-5H-benzo[b]pyrido[2,3-e][1,4]diazepin-6(11H)-yl)(6,7,8,9-tetrahydro-5H-benzo[7]annulen-7-yl)methanone (30 mg, 0.067 mmol) in dioxane (1.0 mL). Aqueous sodium carbonate (2 M, 67 µL, 0.13 mmol) was added and the mixture was then heated to 150° C. for 30 minutes in a microwave reactor. Upon cooling to room temperature, the mixture was filtered and the filtrate was purified by mass triggered reverse phase HPLC (ACN/water with 0.1% TFA modifier) to afford 8-(1-methyl-1H-pyrazol-4-yl)-6-(6,7,8,9-tetrahydro-5H-benzo[7]annulen-7-ylcarbonyl)-6,11-dihydro-5H-pyrido[2,3-b][1,5]benzodiazepine as the TFA salt. MS: 450 (M+1). $^1$H NMR (600 MHz, DMSO-d$_6$): δ 8.08 (s, 1 H); 8.02-8.00 (m, 1 H); 7.84 (s, 1 H); 7.50 (s, 1 H); 7.43 (d, J=8.3 Hz, 2 H); 7.31 (d, J=8.5 Hz, 1 H); 7.03-7.02 (m, 1 H); 7.00-6.96 (m, 2 H); 6.91-6.90 (m, 1H); 6.68 (s, 1 H); 5.17 (d, J=14.9 Hz, 1 H); 3.92 (d, J=15.0 Hz, 1 H); 3.82 (s, 3 H); 2.83-2.81 (m, 2 H); 2.72-2.70 (m, 2 H); 2.16 (br s, 3 H); 1.40-1.38 (m, 2 H); 0.96-0.94 (m, 1 H).

The compounds in the following table were prepared using the methodology herein and the general procedure described in Example 99.

| Ex. No. | Structure | Chemical Name | [M + H]+ |
| --- | --- | --- | --- |
| 100 | 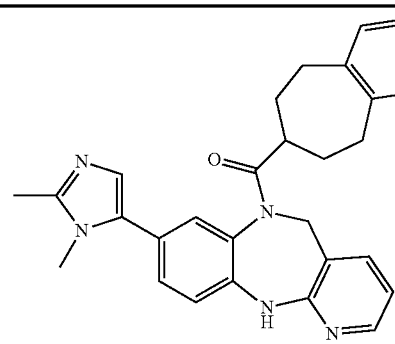 | 8-(1,2-dimethyl-1H-imidazol-5-yl)-6-(6,7,8,9-tetrahydro-5H-benzo[7]annulen-7-ylcarbonyl)-6,11-dihydro-5H-pyrido[2,3-b][1,5]benzodiazepine | 464 |
| 101 | 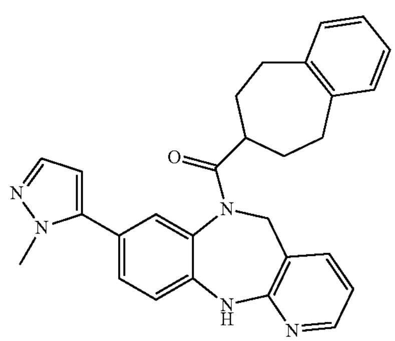 [SMILES: Cn1nccc1-c1ccc2c(c1)N(C(=O)C1CCc3ccccc3CC1)Cc1cccnc1N2] | 8-(1-methyl-1H-pyrazol-5-yl)-6-(6,7,8,9-tetrahydro-5H-benzo[7]annulen-7-ylcarbonyl)-6,11-dihydro-5H-pyrido[2,3-b][1,5]benzodiazepine | 450 |
| 102 | 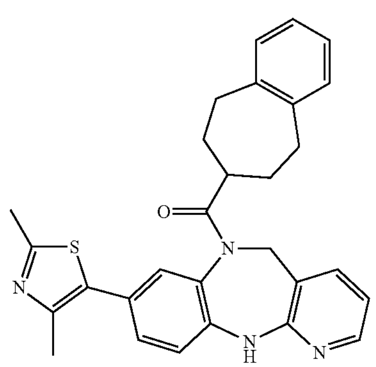 [SMILES: Cc1nc(C)c(-c2ccc3c(c2)N(C(=O)C2CCc4ccccc4CC2)Cc2cccnc2N3)s1] | 8-(2,4-dimethyl-1,3-thiazol-5-yl)-6-(6,7,8,9-tetrahydro-5H-benzo[7]annulen-7-ylcarbonyl)-6,11-dihydro-5H-pyrido[2,3-b][1,5]benzodiazepine | 481 |

-continued

| Ex. No. | Structure | Chemical Name | [M + H]+ |
|---|---|---|---|
| 103 | 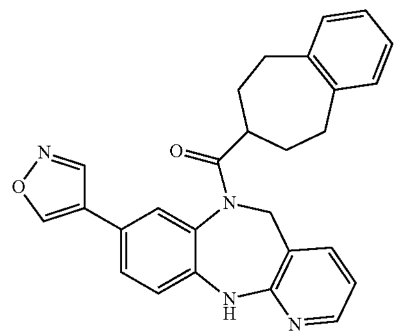 [SMILES: O=C(C1CCc2ccccc2CC1)N1Cc2cccnc2Nc2ccc(-c3cnoc3)cc21] | 8-isoxazol-4-yl-6-(6,7,8,9-tetrahydro-5H-benzo[7]annulen-7-ylcarbonyl)-6,11-dihydro-5H-pyrido[2,3-b][1,5]benzodiazepine | 437 |

Example 104

8-(5-Ethoxypyridin-3-yl)-6-(6,7,8,9-tetrahydro-5H-benzo[7]annulen-7-ylcarbonyl)-6,11-dihydro-5H-pyrido[2,3-b][1,5]benzodiazepine

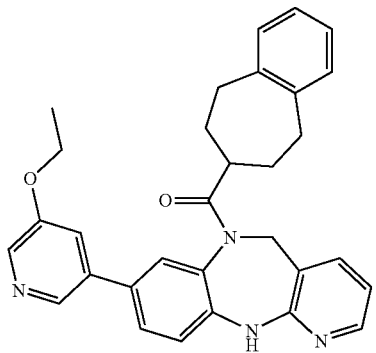 [SMILES: CCOc1cncc(-c2ccc3c(c2)N(C(=O)C2CCc4ccccc4CC2)Cc2cccnc2N3)c1]

To an oven-dried, nitrogen-cooled vial was added 6,7,8,9-tetrahydro-5H-benzo[7]annulen-7-yl[8-(4,4,5,5-tetramethyl-1,3,2-dioxaborolan-2-yl)-5,11-dihydro-6H-pyrido[2,3-b][1,5]benzodiazepin-6-yl]methanone (30 mg, 0.061 mmol), 3-bromo-5-ethoxypyridine (15 mg, 0.073 mmol), and 3$^{rd}$ generation x-phos palladacycle (5 mg, 6 μmol). THF (303 μl) was added, followed by potassium phosphate, tribasic (0.5 M in water, 585 μl, 0.292 mmol), and the reaction mixture was heated to 50° C. for 16 h. Upon cooling to room temperature, the mixture was diluted with EtOAc and then washed with water. The organic layer was dried over sodium sulfate, filtered, and concentrated under reduced pressure. The residue was purified by mass triggered reverse phase HPLC (ACN/water with 0.1% TFA modifier) to afford 8-(5-ethoxypyridin-3-yl)-6-(6,7,8,9-tetrahydro-5H-benzo[7]annulen-7-ylcarbonyl)-6,11-dihydro-5H-pyrido[2,3-b][1,5]benzodiazepine as a solid TFA salt. MS 491 (M+1). $^1$H NMR (500 MHz, DMSO-d$_6$) δ 9.85 (s, 1H), 8.68 (s, 1H), 8.40 (s, 1H), 8.09 (d, J=4.8, 1H), 7.97 (s, 1H), 7.92 (s, 1H), 7.79 (d, J=8.5, 1H), 7.55 (d, J=7.2, 1H), 7.51 (d, J=8.6, 1H), 7.09-6.91 (m, 4H), 6.81-6.76 (m, 1H), 5.23 (d, J=15.0, 1H), 4.28 (q, J=6.9, 2H), 3.99 (d, J=14.8, 1H), 2.94-2.86 (m, 1H), 2.77-2.68 (m, 1H), 2.66-2.56 (m, 1H), 2.47-2.42 (m, 1H), 2.41-2.33 (m, 1H), 2.27-2.19 (m, 1H), 1.51-1.34 (m, 5H), 1.03-0.89 (m, 1H).

Example 105

(R)-(2,3-Dihydrobenzo[b][1,4]dioxin-2-yl)(8-(tetrahydro-2H-pyran-4-yl)-5,11-dihydro-6H-benzo[b]pyrido[2,3-e][1,4]diazepin-6-yl)methanone

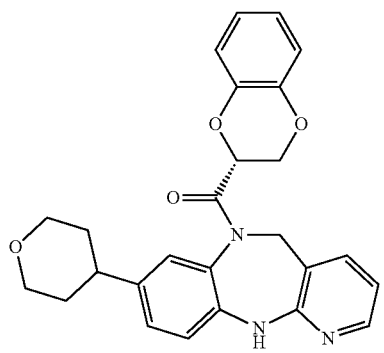 [SMILES: O=C([C@H]1COc2ccccc2O1)N1Cc2cccnc2Nc2ccc(C3CCOCC3)cc21]

Step 1: The Suzuki reaction can be performed as described in Example 104 between (8-bromo-5,11-dihydro-6H-pyrido[2,3-b][1,5]benzodiazepin-6-yl)[(2R)-2,3-dihydro-1,4-benzodioxin-2-yl]methanone and 4-(4,4,5,5-tetramethyl-1,3,2-dioxaborolan-2-yl)-3,6-dihydro-2H-pyran. MS: 442 (M+1).

Step 2: To a flask containing Pd/C (10% loading, 48 mg, 0.045 mmol) was added (R)-(8-(3,6-dihydro-2H-pyran-4-yl)-5H-benzo[b]pyrido[2,3-e][1,4]diazepin-6(11H)-yl)(2,3-dihydrobenzo[b][1,4]dioxin-2-yl)methanone (100 mg, 0.227 mmol) dissolved in 5% HOAc/MeOH (5 mL). The reaction was evacuated and backfilled with hydrogen gas (3×). The resulting reaction mixture was stirred at room temperature for 4 h. The reaction was filtered over a silica gel pad and the filtrate was concentrated under reduced pressure. The residue was purified by reverse phase HPLC (ACN/water with 0.1% TFA modifier) to afford (R)-(2,3-dihydrobenzo[b][1,4]dioxin-2-yl)(8-(tetrahydro-2H-pyran-4-yl)-5,11-dihydro-6H-benzo[b]pyrido[2,3-e][1,4]diazepin-6-yl)methanone as a TFA salt. MS: 444 (M+1).

The compounds in the following table were prepared using the methodology herein and the general procedure described in Example 104.

| Ex. No. | Structure | Chemical Name | [M + H]+ |
| --- | --- | --- | --- |
| 106 | 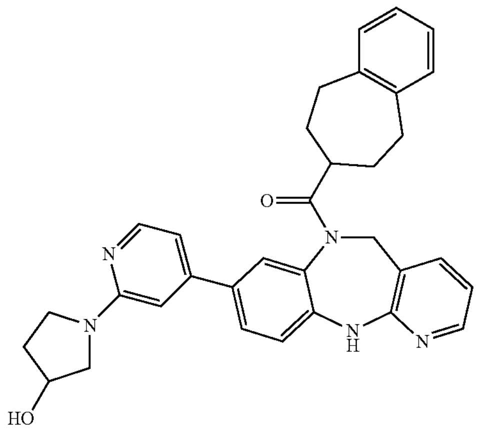 [SMILES: O=C(C1CCc2ccccc2CC1)N1Cc2cccnc2Nc2ccc(-c3ccnc(N4CCC(O)C4)c3)cc21] | 1-{4-[6-(6,7,8,9-tetrahydro-5H-benzo[7]annulen-7-ylcarbonyl)-6,11-dihydro-5H-pyrido[2,3-b][1,5]benzodiazepin-8-yl]pyridin-2-yl}pyrrolidin-3-ol | 532 |
| 107 | 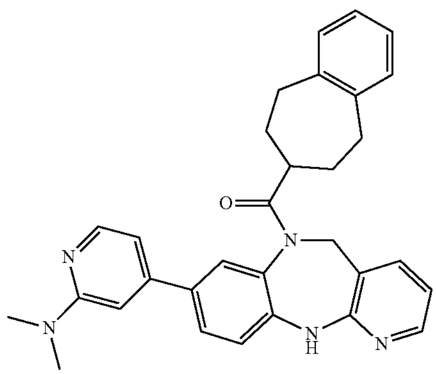 [SMILES: CN(C)c1cc(-c2ccc3c(c2)N(C(=O)C2CCc4ccccc4CC2)Cc2cccnc2N3)ccn1] | N,N-dimethyl-4-[6-(6,7,8,9-tetrahydro-5H-benzo[7]annulen-7-ylcarbonyl)-6,11-dihydro-5H-pyrido[2,3-b][1,5]benzodiazepin-8-yl]pyridin-2-amine | 490 |
| 108 | 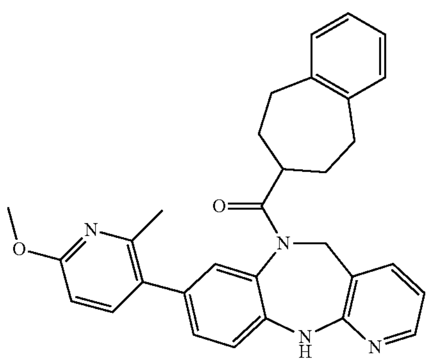 [SMILES: COc1ccc(-c2ccc3c(c2)N(C(=O)C2CCc4ccccc4CC2)Cc2cccnc2N3)c(C)n1] | 8-(6-methoxy-2-methylpyridin-3-yl)-6-(6,7,8,9-tetrahydro-5H-benzo[7]annulen-7-ylcarbonyl)-6,11-dihydro-5H-pyrido[2,3-b][1,5]benzodiazepine | 491 |
| 109 | 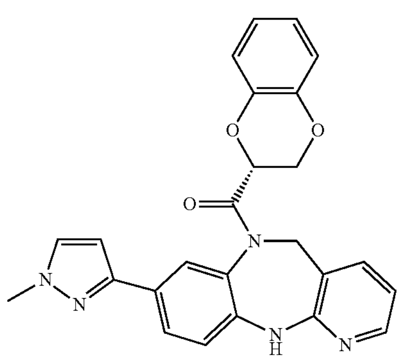 [SMILES: Cn1ccc(-c2ccc3c(c2)N(C(=O)[C@H]2COc4ccccc4O2)Cc2cccnc2N3)n1] | 6-[(2R)-2,3-dihydro-1,4-benzodioxin-2-ylcarbonyl]-8-(1-methyl-1H-pyrazol-3-yl)-6,11-dihydro-5H-pyrido[2,3-b][1,5]benzodiazepine | 440 |

Example 110

2-Ethoxy-11-(6,7,8,9-tetrahydro-5H-benzo[7]annulen-7-ylcarbonyl)-10,11-dihydro-5H-dipyrido[2,3-b:2',3'-e][1,4]diazepine

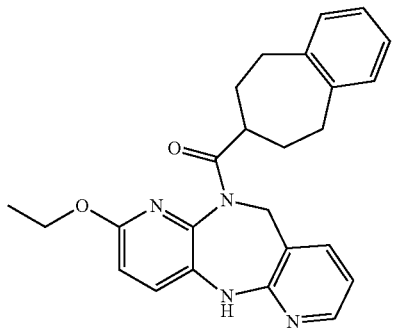 [SMILES: CCOc1ccc2c(n1)N(C(=O)C1CCc3ccccc3CC1)Cc1cccnc1N2]

A vial was charged with (2-bromo-5,10-dihydro-11H-dipyrido[2,3-b:2',3'-e][1,4]diazepin-11-yl)(6,7,8,9-tetrahydro-5H-benzo[7]annulen-7-yl)methanone (36 mg, 0.080 mmol) and brought into a positive pressure $N_2$(g) glove box. [(2-Di-cyclohexylphosphino-3,6-dimethoxy-2',4',6'-triisopropyl-1,1'-biphenyl)-2-(2'-amino-1,1'-biphenyl)]palladium (II) methanesulfonate (7.3 mg, 8.0 μmol), cesium carbonate (52 mg, 0.16 mmol), ethanol (19 μl, 0.32 mmol) and dioxane (0.80 mL) were added to the vial. The reaction was sealed, taken out of the glove box, and heated to 100° C. for 18 hours. Upon cooling to room temperature, the mixture was diluted with DMSO, filtered, and purified by mass triggered reverse phase HPLC (ACN/water with 0.1% TFA modifier) to afford 2-ethoxy-11-(6,7,8,9-tetrahydro-5H-benzo[7]annulen-7-ylcarbonyl)-10,11-dihydro-5H-dipyrido[2,3-b:2',3'-e][1,4]diazepine as the TFA salt. MS 415 (M+1). $^1$H NMR (600 MHz, DMSO-$d_6$) δ 9.51 (s, 1H), 8.06 (d, J=6.0 Hz, 1H), 7.74 (d, J=10.2 Hz, 1H), 7.50 (s, 1H), 7.04 (s, 4H), 6.81 (d, J=8.0 Hz, 1H), 6.73 (s, 1H), 5.22 (s, 1H), 4.39-4.20 (m, 3H), 2.94-2.89 (m, 1H), 2.73-2.52 (m, 3H), 1.45-1.23 (m, 8H).

Example 111

6-({4-[3-(Trifluoromethyl)-1,2,4-oxadiazol-5-yl]bicyclo[2.2.2]oct-1-yl}carbonyl)-6,11-dihydro-5H-pyrido[2,3-b][1,5]benzodiazepine

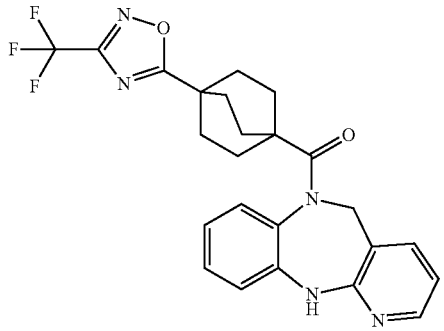 [SMILES: O=C(N1Cc2cccnc2Nc2ccccc21)C12CCC(c3nc(C(F)(F)F)no3)(CC1)CC2]

Step 1: PS-triphenylphosphine (1.93 mmol/g loading, 5.0 g, 9.7 mmol) was divided into three equal portions and then each portion was added to one of three 20-mL microwave vials. Separately, acetonitrile (30 mL) was added to a flask containing 6,11-dihydro-5H-benzo[b]pyrido[2,3-e][1,4]diazepine (1.0 g, 5.1 mmol) and 4-(methoxycarbonyl)bicyclo[2.2.2]octane-1-carboxylic acid (1.6 g, 7.6 mmol) to give a suspension that was gently heated until dissolved. This mixture was then distributed in equal portions to the three microwave vials described above. 2,2,2-trichloroacetonitrile (2.03 mL, 20 mmol) was divided into three equal portions and one portion was added to each vial. Concurrently, each vial was heated to 120° C. for 20 minutes in a microwave reactor. Upon cooling to room temperature, each mixture was filtered, and the solids were washed with ethyl acetate. The filtrates were combined and then washed with saturated aqueous sodium bicarbonate (100 mL) and then with brine (100 mL). The organic phase was dried over sodium sulfate, filtered and concentrated under reduced pressure. The residue was purified by column chromatography on silica gel (0-100% ethyl acetate in hexanes) to afford methyl 4-(6,11-dihydro-5H-benzo[b]pyrido[2,3-e][1,4]diazepine-6-carbonyl)bicyclo[2.2.2]octane-1-carboxylate as a solid. MS 392 (M+1). $^1$H NMR (500 MHz, CDCl$_3$) δ 8.98 (s, 1H), 7.97 (d, J=4.5 Hz, 1H), 7.54 (d, J=7.1 Hz, 1H), 7.32-7.28 (m, 1H), 7.24 (d, J=7.7 Hz, 1H), 7.20 (d, J=8.0 Hz, 1H), 7.03 (dd, J=7.6 Hz, 7.5 Hz, 1H), 6.78 (dd, J=7.2 Hz, 5.1 Hz, 1H), 5.50 (d, J=14.7 Hz, 1H), 3.85 (d, J=14.6 Hz, 1H), 3.62 (s, 3H), 1.84-1.52 (m, 12H).

Step 2: To a mixture of methyl 4-(6,11-dihydro-5H-benzo[b]pyrido[2,3-e][1,4]diazepine-6-carbonyl)bicyclo[2.2.2]octane-1-carboxylate (280 mg, 0.715 mmol) in methanol (4 mL) and tetrahydrofuran (4 mL) was added aqueous lithium hydroxide (2 N, 4.0 mL, 8.0 mmol). The mixture was stirred at room temperature for 18 hours. The mixture was then partitioned between ethyl acetate (100 mL) and saturated aqueous ammonium chloride (100 mL). The aqueous phase was extracted with ethyl acetate (50 mL) twice. The combined organic extracts were dried over sodium sulfate, filtered and concentrated under reduced pressure to afford 4-(6,11-dihydro-5H-benzo[b]pyrido[2,3-e][1,4]diazepine-6-carbonyl)bicyclo[2.2.2]octane-1-carboxylic acid as a tacky solid. MS 378 (M+1).

Step 3: To a mixture of 4-(6,11-dihydro-5H-benzo[b]pyrido[2,3-e][1,4]diazepine-6-carbonyl)bicyclo[2.2.2]octane-1-carboxylic acid (16 mg, 0.042 mmol) and di(1H-imidazol-1-yl)methanone (12 mg, 0.072 mmol) was added dichloromethane (0.4 mL) and the mixture was stirred at room temperature for 15 minutes under a nitrogen atmosphere. (Z)-2,2,2-trifluoro-N'-hydroxyacetimidamide (11 mg, 0.085 mmol) was then added and the resulting mixture was stirred at room temperature for 40 minutes under a nitrogen atmosphere. More (Z)-2,2,2-trifluoro-N'-hydroxyacetimidamide (11 mg, 0.085 mmol) and di(1H-imidazol-1-yl)methanone (12 mg, 0.072 mmol) were then added and the resulting mixture was stirred at room temperature for 18 hours under a nitrogen atmosphere. The mixture was then concentrated by passing a stream of nitrogen over the reaction mixture. Toluene (0.4 mL) was then added and the mixture was heated to 95° C. for 3 hours. Upon cooling to room temperature, the mixture was concentrated by passing a stream of nitrogen over the reaction mixture. The residue was dissolved in dimethyl sulfoxide (1.3 mL) and filtered through an aerodisc filter (0.45 micron). The filtrate was purified by mass-directed HPLC (25 mL/min, 8 min, 45-80% acetonitrile gradient in water with a 0.1% ammonium hydroxide modifier, Waters X-Bridge C18 column, 5

μm, 19×100 mm) to afford 6-({4-[3-(trifluoromethyl)-1,2,4-oxadiazol-5-yl]bicyclo[2.2.2]oct-1-yl}carbonyl)-6,11-dihydro-5H-pyrido[2,3-b][1,5]benzodiazepine as a solid. MS 470 (M+1). $^1$H NMR (500 MHz, DMSO-d$_6$) δ 9.39 (s, 1H), 8.05 (d, J=4.7 Hz, 1H), 7.46 (d, J=7.3 Hz, 1H), 7.35 (d, J=8.1 Hz, 1H), 7.30-7.25 (m, 2H), 6.97 (t, J=7.5 Hz, 1H), 6.73 (dd, J=7.3 Hz, 4.8 Hz, 1H), 5.32 (d, J=14.9 Hz, 1H) 3.84 (d, J=14.9 Hz, 1H), 1.90-1.70 (m, 9H); 1.62-1.45 (m, 3H).

Examples 112-115

6-(6,7,8,9-Tetrahydro-5H-cyclohepta[b]pyridin-6-ylcarbonyl)-6,11-dihydro-5H-pyrido[2,3-b][1,5]benzodiazepine isomers 1 and 2 (Ex. 112 and Ex. 113) and 6-(6,7,8,9-Tetrahydro-5H-cyclohepta[b]pyridin-7-ylcarbonyl)-6,11-dihydro-5H-pyrido[2,3-b][1,5]benzodiazepine isomers 1 and 2 (Ex. 114 and Ex. 115)

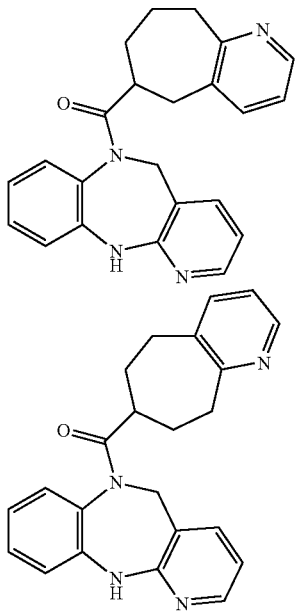

Step 1: To a mixture of n-butyllithium (1.6 M in hexanes, 5.1 mL, 8.2 mmol) in diethyl ether (24 mL) at −78° C. was added trimethylsilyldiazomethane (2.0 M in hexanes, 3.8 mL, 7.6 mmol), and the mixture was stirred for 10 minutes at −78° C. A mixture of ethyl 4-oxocyclohexanecarboxylate (1.0 g, 5.9 mmol) in THF (5 mL) was cooled to −78° C. and then added to the previously generated anion, and the mixture was stirred for 20 minutes. A mixture of methanol (0.48 mL, 12 mmol) in THF (5 mL) was added, and the mixture was allowed to warm to room temperature over 2 hours. The mixture was then diluted with ether and the mixture was washed with water and then brine. The organic layer was dried over magnesium sulfate, filtered and concentrated under reduced pressure. The residue was then purified by column chromatography on silica gel to afford ethyl 4-oxocycloheptanecarboxylate that was taken on to the next step without further characterization.

Step 2: To a mixture of ethyl 4-oxocycloheptanecarboxylate (650 mg, 3.53 mmol) and propargylamine (0.45 mL, 7.1 mmol) in ethanol (9.0 mL) was added sodium tetrachloroaurate (III) dihydrate (56 mg, 0.14 mmol), and the mixture was heated to 65° C. for 5 hours. Upon allowing to cool to room temperature, the mixture was diluted with water and extracted with ethyl acetate. The organic layer was then dried over magnesium sulfate, filtered and concentrated under reduced pressure. The residue was purified by column chromatography on silica gel to afford a mixture of ethyl 6,7,8,9-tetrahydro-5H-cyclohepta[b]pyridine-7-carboxylate and ethyl 6,7,8,9-tetrahydro-5H-cyclohepta[b]pyridine-6-carboxylate that was used as a mixture in the subsequent reaction. MS: 220 (M+1).

Step 3: To a mixture of ethyl 6,7,8,9-tetrahydro-5H-cyclohepta[b]pyridine-7-carboxylate and ethyl 6,7,8,9-tetrahydro-5H-cyclohepta[b]pyridine-6-carboxylate (600 mg, 2.74 mmol) in methanol (7.0 mL) was added sodium hydroxide (547 mg, 13.7 mmol), and the mixture was stirred for 45 minutes. The mixture was then acidified to a pH ~4 with aqueous HCl (2M, 6.8 mL, 14 mmol), and the mixture was diluted with dichloromethane and water. The water layer was separated, and the aqueous portion was frozen in a −78° C. bath and concentrated under reduced pressure to afford a white solid that was a mixture of 6,7,8,9-tetrahydro-5H-cyclohepta[b]pyridine-6-carboxylic acid, 6,7,8,9-tetrahydro-5H-cyclohepta[b]pyridine-7-carboxylic acid and sodium chloride. The mixture was taken on to the next step without further purification or characterization.

Step 4: 6,11-Dihydro-5H-pyrido[2,3-b][1,5]benzodiazepine (75 mg, 0.38 mmol) and a mixture of 6,7,8,9-tetrahydro-5H-cyclohepta[b]pyridine-6-carboxylic acid and 6,7,8,9-tetrahydro-5H-cyclohepta[b]pyridine-7-carboxylic acid (1:1) (30 wt % mixture with sodium chloride, 242 mg, 0.190 mmol) were combined in a microwave vial and suspended in acetonitrile (2 mL). Polymer supported triphenylphosphine (1.93 mmol/g loading, 591 mg, 1.14 mmol) and trichloroacetonitrile (190 μL, 1.90 mmol) were added and the vial was sealed and then heated to 100° C. for 10 minutes in a microwave reactor. Upon cooling to room temperature, the mixture was filtered, diluted with DMSO, and purified by mass triggered reverse phase HPLC (ACN/water with 0.1% TFA modifier) to afford a 1:1 mixture of regioisomeric products. This mixture was purified by chiral SFC (Chiralpak IA column, 30%/70% methanol/CO$_2$ with 0.25% N,N-dimethylethanamine modifier) to afford: 6-(6,7,8,9-tetrahydro-5H-cyclohepta[b]pyridin-6-ylcarbonyl)-6,11-dihydro-5H-pyrido[2,3-b][1,5]benzodiazepine (Isomer 1, first eluting: MS 371 (M+1). $^1$H NMR (600 MHz, DMSO-d$_6$) δ 9.59-9.35 (m, 1H), 8.16-8.01 (m, 2H), 7.63-7.39 (m, 2H), 7.27-7.25 (m, 1H), 7.19-7.16 (m, 1H), 7.11-7.08 (m, 1H), 6.84-6.60 (m, 3H), 5.23-5.15 (m, 1H), 3.94-3.90 (m, 1H), 2.94-2.84 (m, 2H), 2.78-2.52 (m, 2H), 2.49-2.13 (m, 1H), 2.00-1.66 (m, 2H), 1.46-1.38 (m, 1H), 1.15-0.75 (m, 1H).

6-(6,7,8,9-tetrahydro-5H-cyclohepta[b]pyridin-6-ylcarbonyl)-6,11-dihydro-5H-pyrido[2,3-b][1,5]benzodiazepine (Isomer 2, second eluting): MS 371 (M+1). $^1$H NMR (600 MHz, DMSO-d$_6$) δ 9.59-9.36 (m, 1H), 8.16-8.01 (m, 2H), 7.63-7.39 (m, 2H), 7.27-7.25 (m, 1H), 7.19-7.16 (m, 1H), 7.11-7.08 (m, 1H), 6.84-6.60 (m, 3H), 5.23-5.16 (m, 1H), 3.94-3.90 (m, 1H), 2.94-2.83 (m, 2H), 2.78-2.52 (m, 2H), 2.48-2.13 (m, 1H), 2.00-1.66 (m, 2H), 1.46-1.38 (m, 1H), 1.15-0.75 (m, 1H).

6-(6,7,8,9-tetrahydro-5H-cyclohepta[b]pyridin-7-ylcarbonyl)-6,11-dihydro-5H-pyrido[2,3-b][1,5]benzodiazepine (Isomer 1, third eluting): MS 371 (M+1). $^1$H NMR (600 MHz, DMSO-d$_6$) δ 9.40 (s, 1H), 8.15-8.12 (m, 1H), 8.01-8.00 (m, 1H), 7.43-7.31 (m, 3H), 7.28 (d, J=7.8 Hz, 1H), 7.23 (t, J=7.8 Hz, 1H), 7.04-7.00 (m, 1H), 6.94-6.92 (m, 1H), 6.69-6.67 (m, 1H), 5.16 (d, J=15 Hz, 1H), 3.90-3.87 (m, 1H), 2.93-2.72 (m, 2H), 2.65-2.47 (m, 2H), 2.35-2.31 (m, 1H), 2.12-2.08 (m, 1H), 1.48-1.36 (m, 2H), 1.11-0.94 (m, 1H).

6-(6,7,8,9-tetrahydro-5H-cyclohepta[b]pyridin-7-ylcarbonyl)-6,11-dihydro-5H-pyrido[2,3-b][1,5]benzodiazepine (Isomer 2, fourth eluting): MS 371 (M+1). ¹H NMR (600 MHz, DMSO-d₆) δ 9.41 (s, 1H), 8.16-8.12 (m, 1H), 8.01-8.00 (m, 1H), 7.44-7.31 (m, 3H), 7.28 (d, J=7.8 Hz, 1H), 7.23 (t, J=7.8 Hz, 1H), 7.05-7.00 (m, 1H), 6.94-6.92 (m, 1H), 6.69-6.67 (m, 1H), 5.16 (d, J=15 Hz, 1H), 3.90-3.87 (m, 1H), 2.93-2.72 (m, 2H), 2.66-2.47 (m, 2H), 2.35-2.31 (m, 1H), 2.12-2.08 (m, 1H), 1.48-1.36 (m, 2H), 1.11-0.94 (m, 1H).

Example 116

2-[6-(6,7,8,9-Tetrahydro-5H-benzo[7]annulen-7-ylcarbonyl)-6,11-dihydro-5H-pyrido[2,3-b][1,5]benzodiazepin-8-yl]propan-2-ol

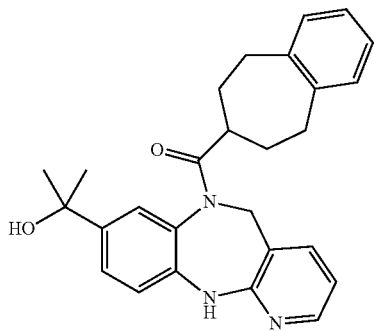 [SMILES: CC(C)(O)c1ccc2c(c1)N(C(=O)C1CCc3ccccc3CC1)Cc1cccnc1N2]

To a mixture of tert-butyl 8-acetyl-6-(6,7,8,9-tetrahydro-5H-benzo[7]annulen-7-ylcarbonyl)-5,6-dihydro-11H-pyrido[2,3-b][1,5]benzodiazepine-11-carboxylate (96 mg, 0.19 mmol) in THF (0.94 mL) at 0° C. was added methylmagnesium bromide (3.0M in diethyl ether, 69 µL, 0.21 mmol) dropwise. The mixture was stirred for 2 h at 0° C. The mixture was then quenched with saturated aqueous ammonium chloride (5 mL) and allowed to warm to room temperature for 10 minutes. The quenched mixture was partitioned between EtOAc and water. The organic layer was separated, washed with brine, dried over sodium sulfate, filtered, and concentrated under reduced pressure. The residue was purified by column chromatography on silica gel (0-100% 3:1 EtOAc:EtOH/Hexanes) to afford 2-[6-(6,7,8,9-tetrahydro-5H-benzo[7]annulen-7-ylcarbonyl)-6,11-dihydro-5H-pyrido[2,3-b][1,5]benzodiazepin-8-yl]propan-2-ol as a solid. MS 428 (M+1). ¹H NMR (500 MHz, DMSO-d₆) δ 9.37 (s, 1H), 8.05-8.01 (m, 1H), 7.43 (d, J=6.2 Hz, 1H), 7.36-7.31 (m, 2H), 7.28 (d, J=8.4 Hz, 1H), 7.10-7.07 (m, 1H), 7.06-6.98 (m, 2H), 6.98-6.95 (m, 1H), 6.71-6.67 (m, 1H), 5.19 (d, J=14.9 Hz, 1H), 5.02 (s, 1H), 3.92 (d, J=14.8 Hz, 1H), 2.88-2.72 (m, 2H), 2.62-2.54 (m, 1H), 2.37-2.27 (m, 1H), 2.22-2.11 (m, 1H), 1.44 (d, J=14.6 Hz, 6H), 1.41-1.30 (m, 3H), 1.07-0.95 (m, 1H).

Example 117

N,N-Dimethyl-11-(6,7,8,9-tetrahydro-5H-benzo[7]annulen-7-ylcarbonyl)-10,11-dihydro-5H-dipyrido[2,3-b:2',3'-e][1,4]diazepin-2-amine

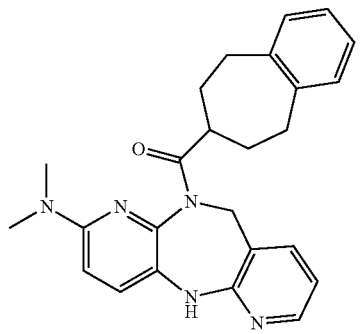 [SMILES: CN(C)c1ccc2c(n1)N(C(=O)C1CCc3ccccc3CC1)Cc1cccnc1N2]

To an oven-dried, N₂ cooled vial was added (2-bromo-5H-dipyrido[2,3-b:2',3'-e][1,4]diazepin-11(10H)-yl)(6,7,8,9-tetrahydro-5H-benzo[7]annulen-7-yl)methanone (20 mg, 0.045 mmol), chloro(2-dicyclohexylphosphino-2',6'-di-i-propoxy-1,1'-biphenyl)[2-(2-aminoethylphenyl)]palladium (II), methyl-t-butylether adduct (1.8 mg, 2.2 µmol) and 2-dicyclohexylphosphino-2',6'-di-i-propoxy-1,1'-biphenyl (1.0 mg, 2.2 µmol). The vial was evacuated and filled with nitrogen. LiHMDS (1.0 M in THF, 150 µL, 0.150 mmol) and then dimethylamine (2.0 M in THF, 27 µL, 0.053 mmol) were added and the mixture was heated to 100° C. for 18 h. Upon cooling to room temperature, the mixture was diluted with methanol and filtered. The filtrate was then concentrated under reduced pressure and then purified by reverse phase HPLC (acetonitrile and water with 0.1% TFA modifier) to afford N,N-dimethyl-11-(6,7,8,9-tetrahydro-5H-benzo[7]annulen-7-ylcarbonyl)-10,11-dihydro-5H-dipyrido[2,3-b:2',3'-e][1,4]diazepin-2-amine, isolated as the TFA salt. ¹H NMR (600 MHz, DMSO-d₆) δ 9.51 (s, 1H), 8.00 (s, 1H), 7.55 (d, J=8.9 Hz, 1H), 7.54-7.49 (m, 1H), 7.10-6.93 (m, 4H), 6.68 (d, J=9.7 Hz, 2H), 5.37-5.08 (m, 1H), 3.99-3.69 (m, 1H), 2.98 (s, 6H), 2.97-2.90 (m, 1H), 2.80-2.50 (m, 4H), 1.57-1.01 (m, 4H).

Example 118

2-Morpholin-4-yl-11-(6,7,8,9-tetrahydro-5H-benzo[7]annulen-7-ylcarbonyl)-10,11-dihydro-5H-dipyrido[2,3-b:2',3'-e][1,4]diazepine

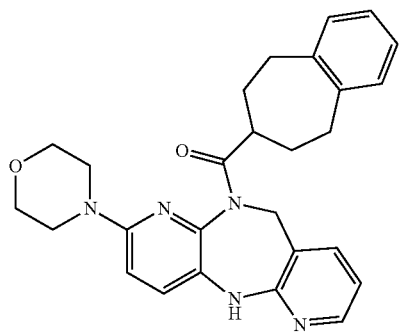 [SMILES: O=C(C1CCc2ccccc2CC1)N1Cc2cccnc2Nc2ccc(N3CCOCC3)nc21]

Step 1: To an oven-dried, nitrogen-cooled vial was added 2-bromo-10,11-dihydro-5H-dipyrido[2,3-b:2',3'-e][1,4]diazepine (100 mg, 0.361 mmol), chloro(2-dicyclohexylphosphino-2',6'-di-i-propoxy-1,1'-biphenyl)[2-(2-aminoethylphenyl)]palladium(II), methyl-t-butylether adduct (15 mg, 0.018 mmol), and 2-dicyclohexylphosphino-2',6'-di-i-propoxy-1,1'-biphenyl (8 mg, 0.02 mmol). The mixture was placed under a nitrogen atmosphere by performing 3 vacuum/nitrogen cycles. LiHMDS (1.0 M in THF, 1.2 mL, 1.2 mmol) was added dropwise, followed by morpholine (38 µl, 0.43 mmol), and the reaction mixture was heated to 100° C. for 16 h. Upon cooling to room temperature, the mixture was quenched with aqueous HCl (2 M) to pH 7, and extracted with EtOAc (3×20 mL). The combined organic layers were washed with brine, dried over sodium sulfate, filtered, and concentrated under reduced pressure. The residue was purified by mass triggered reverse phase HPLC (ACN/water with 0.1% TFA modifier) to afford 2-(morpholin-4-yl)-10,11-dihydro-5H-dipyrido[2,3-b:2',3'-e][1,4]diazepine as a solid TFA salt. MS 284 (M+1).

Step 2: To a vial containing 6,7,8,9-tetrahydro-5H-benzo[7]annulene-7-carboxylic acid (50 mg, 0.26 mmol) was added thionyl chloride (767 µl, 10.5 mmol) and the mixture was heated to 70° C. for 16 h. Upon cooling to room temperature, the mixture was concentrated under reduced pressure to afford 6,7,8,9-tetrahydro-5H-benzo[7]annulene-7-carbonyl chloride as an oil. The material was used without further purification or characterization in the next step.

Step 3: To a mixture of 2-(morpholin-4-yl)-10,11-dihydro-5H-dipyrido[2,3-b:2',3'-e][1,4]diazepine (70 mg, 0.25 mmol) in THF (2.5 mL) at 0° C. was added NaHMDS (1.0 M in THF, 519 µl, 0.519 mmol). After 5 min at 0° C., 6,7,8,9-tetrahydro-5H-benzo[7]annulene-7-carbonyl chloride (52 mg, 0.25 mmol) was added and the mixture was stirred at 0° C. for 1 h. The reaction mixture was quenched with water and extracted with EtOAc (2×10 mL). The combined organic layers were dried over sodium sulfate, filtered, and concentrated under reduced pressure. The residue was purified by mass triggered reverse phase HPLC (ACN/water with 0.1% TFA modifier) to afford 2-morpholin-4-yl-11-(6,7,8,9-tetrahydro-5H-benzo[7]annulen-7-ylcarbonyl)-10,11-dihydro-5H-dipyrido[2,3-b:2',3'-e][1,4]diazepine as a solid TFA salt. MS 456 (M+1). 1H NMR (500 MHz, DMSO-d6) δ 9.50 (s, 1H), 8.04 (d, J=4.7 Hz, 1H), 7.64 (d, J=8.9 Hz, 1H), 7.52 (s, 1H), 7.04 (s, 4H), 6.90 (d, J=8.9 Hz, 1H), 6.73 (d, J=5.5 Hz, 1H), 5.41-5.07 (m, 1H), 3.73 (s, 1H), 3.39 (s, 5H), 2.93-2.85 (m, 2H), 2.79-2.60 (m, 3H), 2.17 (t, J=7.4 Hz, 1H), 1.93-1.79 (m, 1H), 1.50-1.30 (m, 3H), 0.84 (d, J=6.9 Hz, 2H).

Example 119

(4R)-4-(1-Methylethyl)-3-{6-[(3S,5S,7S)-tricyclo[3.3.1.1~3,7~]dec-1-ylcarbonyl]-6,11-dihydro-5H-pyrido[2,3-b][1,5]benzodiazepin-8-yl}-1,3-oxazolidin-2-one

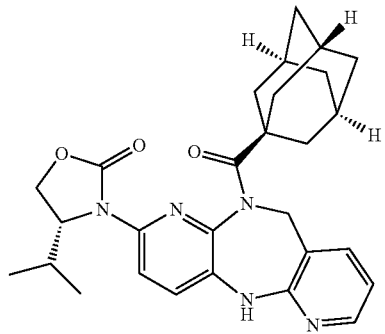 [SMILES: CC(C)[C@@H]1COC(=O)N1c1ccc2c(n1)N(C(=O)[C@]13C[C@H]4C[C@H](C[C@H](C4)C1)C3)Cc1cccnc1N2]

To a microwave vial was added (R)-3-(6,11-dihydro-5H-benzo[b]pyrido[2,3-e][1,4]diazepin-8-yl)-4-isopropyloxazolidin-2-one (28 mg, 0.084 mmol), (3r,5r,7r)-adamantane-1-carboxylic acid (15 mg, 0.084 mmol), PS-triphenylphosphine (1.94 mmol/g loading, 130 mg, 0.252 mmol), trichloroacetonitrile (42 µL, 0.42 mmol) and acetonitrile (1.4 mL). The mixture was heated to 100° C. for 10 minutes in a microwave reactor. Upon cooling to room temperature, the mixture was filtered through celite. The filtrate was purified by reverse phase HPLC (ACN/water with 0.1% TFA modifier) to afford (4R)-4-(1-methylethyl)-3-{6-[(3S,5S,7S)-tricyclo[3.3.1.1~3,7~]dec-1-ylcarbonyl]-6,11-dihydro-5H-pyrido[2,3-b][1,5]benzodiazepin-8-yl}-1,3-oxazolidin-2-one as the TFA salt. MS 487 (M+1). 1H NMR (600 MHz, CDCl3) δ 12.44-12.41 (m, 1H), 8.02-7.78 (m, 3H), 7.61-7.57 (m, 1H), 7.32-7.18 (m, 1H), 6.96-6.93 (m, 1H), 5.56-5.52 (m, 1H), 4.54-4.43 (m, 2H), 4.30 (s, 1H), 3.88-3.81 (m, 1H), 2.22-2.10 (m, 1H), 1.95-1.80 (m, 6H), 1.64-1.42 (m, 9H), 0.99-0.94 (m, 3H), 0.88-0.85 (m, 3H).

Example 120

4-[6-(6,7,8,9-Tetrahydro-5H-benzo[7]annulen-7-ylcarbonyl)-6,11-dihydro-5H-pyrido[2,3-b][1,5]benzodiazepin-8-yl]pyrrolidin-2-one

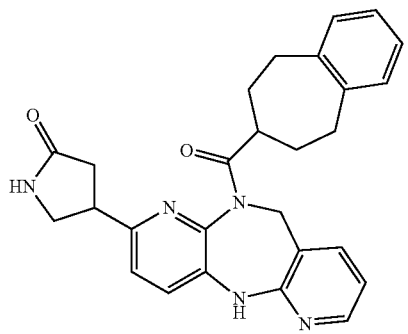 [SMILES: O=C1CC(c2ccc3c(n2)N(C(=O)C2CCc4ccccc4CC2)Cc2cccnc2N3)CN1]

Step 1: To a mixture of (8-bromo-5H-benzo[b]pyrido[2,3-e][1,4]diazepin-6(11H)-yl)(6,7,8,9-tetrahydro-5H-benzo

[7]annulen-7-yl)methanone, HCl salt (550 mg, 1.13 mmol), TEA (0.47 mL, 3.4 mmol) and DMAP (139 mg, 1.13 mmol) in THF (2 mL) was added BOC-anhydride (371 mg, 1.70 mmol). The resulting reaction mixture was heated to 70° C. for 2 hours. Upon cooling to room temperature, the reaction was concentrated under reduced pressure. The residue was purified by column chromatography on silica gel (0-100% EtOAc/hexanes) to afford tert-butyl 8-bromo-6-(6,7,8,9-tetrahydro-5H-benzo[7]annulene-7-carbonyl)-5H-benzo[b]pyrido[2,3-e][1,4]diazepine-11(6H)-carboxylate. MS 549 (M+1).

Step 2: To a mixture of tert-butyl 8-bromo-6-(6,7,8,9-tetrahydro-5H-benzo[7]annulene-7-carbonyl)-5H-benzo[b]pyrido[2,3-e][1,4]diazepine-11(6H)-carboxylate (340 mg, 0.620 mmol), bis(pinacolato)diboron (315 mg, 1.24 mmol), XPhos biphenyl precatalyst (49 mg, 0.042 mmol) and potassium acetate (122 mg, 1.24 mmol) was added cyclopentyl methylether (3 mL). The resulting reaction mixture was placed under a nitrogen atmosphere by performing 6 vacuum/nitrogen cycles and then heated to 100° C. for 2 hours. Upon cooling to room temperature, the mixture was diluted with ethyl acetate, washed with water, dried over magnesium sulfate, filtered and concentrated under reduced pressure. The residue was purified by column chromatography on silica gel (0-100% EtOAc/hexanes) to afford tert-butyl 6-(6,7,8,9-tetrahydro-5H-benzo[7]annulene-7-carbonyl)-8-(4,4,5,5-tetramethyl-1,3,2-dioxaborolan-2-yl)-5H-benzo[b]pyrido[2,3-e][1,4]diazepine-11(6H)-carboxylate. MS 596 (M+1).

Step 3: To a mixture of tert-butyl 6-(6,7,8,9-tetrahydro-5H-benzo[7]annulene-7-carbonyl)-8-(4,4,5,5-tetramethyl-1,3,2-dioxaborolan-2-yl)-5H-benzo[b]pyrido[2,3-e][1,4]diazepine-11(6H)-carboxylate (330 mg, 0.554 mmol), tert-butyl 4-bromo-2-oxo-2,5-dihydro-1H-pyrrole-1-carboxylate (290 mg, 1.11 mmol), chloro[(di(1-adamantyl)-N-butylphosphine)-2-(2-aminobiphenyl)]palladium(II) (37 mg, 0.055 mmol) and potassium carbonate (230 mg, 1.66 mmol) was added dioxane (2 mL) and water (0.3 mL). The resulting reaction mixture was placed under a nitrogen atmosphere by performing 6 vacuum/nitrogen cycles. The mixture was heated to 100° C. for 1 hour in a microwave reactor. Upon cooling to room temperature, the mixture was diluted with ethyl acetate, washed with water, dried over magnesium sulfate, filtered and concentrated under reduced pressure. The residue was purified by column chromatography on silica gel (0-100% EtOAc/hexanes) to afford tert-butyl 8-(1-(tert-butoxycarbonyl)-5-oxo-2,5-dihydro-1H-pyrrol-3-yl)-6-(6,7,8,9-tetrahydro-5H-benzo[7]annulene-7-carbonyl)-5H-benzo[b]pyrido[2,3-e][1,4]diazepine-11 (6H)-carboxylate. MS 651 (M+1).

Step 4: To a mixture of tert-butyl 8-(1-(tert-butoxycarbonyl)-5-oxo-2,5-dihydro-1H-pyrrol-3-yl)-6-(6,7,8,9-tetrahydro-5H-benzo[7]annulene-7-carbonyl)-5H-benzo[b]pyrido[2,3-e][1,4]diazepine-11(6H)-carboxylate (110 mg, 0.169 mmol) in MeOH (30 mL) was added Pd/C (10% loading, 180 mg, 0.169 mmol). The mixture was fitted with a hydrogen balloon and the mixture was evacuated and purged 6 times with hydrogen. The mixture was stirred overnight at room temperature. The solvent was removed under reduced pressure to afford tert-butyl 8-(1-(tert-butoxycarbonyl)-5-oxopyrrolidin-3-yl)-6-(6,7,8,9-tetrahydro-5H-benzo[7]annulene-7-carbonyl)-5H-benzo[b]pyrido[2,3-e][1,4]diazepine-11 (6H)-carboxylate. MS 653 (M+1).

Step 5: To a mixture of tert-butyl 8-(1-(tert-butoxycarbonyl)-5-oxopyrrolidin-3-yl)-6-(6,7,8,9-tetrahydro-5H-benzo[7]annulene-7-carbonyl)-5H-benzo[b]pyrido[2,3-e][1,4]diazepine-11(6H)-carboxylate (30 mg, 0.046 mmol) in DCM (0.5 mL) was added TFA (1 mL) and the mixture was stirred at room temperature for one hour. The mixture was then concentrated under reduced pressure. The residue was purified by reverse phase HPLC (ACN/water with 0.1% TFA modifier) to afford 4-[6-(6,7,8,9-tetrahydro-5H-benzo[7]annulen-7-ylcarbonyl)-6,11-dihydro-5H-pyrido[2,3-b][1,5]benzodiazepin-8-yl]pyrrolidin-2-one as a TFA salt. MS 453 (M+1). $^1$H NMR (600 MHz, CDCl$_3$) δ 12.62 (s, 1H), 7.90-7.88 (m, 3H), 7.65-7.62 (m, 1H), 7.28 (s, 1H), 7.10-6.92 (m, 5H), 5.48-5.43 (m, 1H), 3.95-3.90 (m, 2H), 3.83-3.78 (m, 1H), 3.50-3.40 (m, 2H), 2.95-2.80 (m, 2H), 2.72-2.60 (m, 2H), 2.60-2.43 (m, 2H), 2.20-2.15 (m, 1H), 1.82-1.72 (m, 1H), 1.53-1.48 (m, 1H), 1.41-1.30 (m, 1H).

Example 121

8-Morpholin-4-yl-6-(1-oxaspiro[3.5]non-7-ylcarbonyl)-6,11-dihydro-5H-pyrido[2,3-b][1,5]benzodiazepine

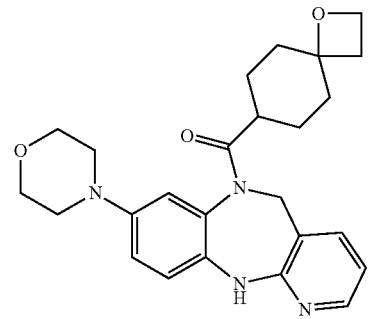 [SMILES: O=C(C1CCC2(CCO2)CC1)N1Cc2cccnc2Nc2ccc(N3CCOCC3)cc21]

Step 1: To a mixture of 4-oxocyclohexanecarboxylic acid (430 mg, 3.02 mmol) in DCM (5 mL) was added DMF (one drop) followed by oxalyl chloride (0.27 mL, 3.1 mmol) and the mixture was stirred for one hour at room temperature. The mixture was concentrated under reduced pressure. To the residue was added DCE (2.5 mL) and the mixture was heated to reflux. A mixture of 4-(6,11-dihydro-5H-benzo[b]pyrido[2,3-e][1,4]diazepin-8-yl)morpholine in DCE (5 mL) was added to the reaction over 3 min. 4-Dimethylaminopyridine (23 mg, 0.19 mmol) was then added and the mixture was heated to reflux overnight. Upon cooling to room temperature, the mixture was diluted with saturated aqueous sodium bicarbonate and washed with DCM. The organic layer was then washed with brine, dried over sodium sulfate, filtered and concentrated under reduced pressure. The residue was purified by column chromatography on silica gel (1-5% MeOH in DCM) to afford 4-(8-morpholino-6,11- dihydro-5H-benzo[b]pyrido[2,3-e][1,4]diazepine-6-carbonyl)cyclohexanone. MS 407 (M+1).

Step 2: To a mixture of trimethyloxosulfonium iodide (113 mg, 0.515 mmol) in tert-butanol (3 mL) was added a mixture of potassium tert-butoxide (56 mg, 0.50 mmol) in tert-butanol (1 mL) and the mixture was heated to 50° C. for 30 min. A mixture of 4-(8-morpholino-6,11-dihydro-5H-benzo[b]pyrido[2,3-e][1,4]diazepine-6-carbonyl)cyclohexanone (53 mg, 0.13 mmol) in tert-butanol (1 mL) was added and the mixture was heated to 50° C. for 60 h. Upon cooling to room temperature, the mixture was concentrated under reduced pressure. The residue was diluted with water and washed with ethyl acetate. The organic layer was washed with brine, dried over anhydrous sodium sulfate, filtered and concentrated under reduced pressure. The residue was purified by mass triggered reverse phase HPLC (ACN/water) to afford 8-morpholin-4-yl-6-(1-oxaspiro[3.5]non-7-ylcarbonyl)-6,11-dihydro-5H-pyrido[2,3-b][1,5]benzodiazepine. MS 435 (M+1). $^1$H NMR (400 MHz, CD$_3$OD) δ 7.96 (d, J=8.8 Hz, 1H), 7.46 (d, J=7.0 Hz, 1H), 7.15-7.12 (m, 1H), 6.99-6.95 (m, 1H), 6.84-6.82 (m, 1H), 6.70-6.67 (m, 1H), 5.30-5.26 (m, 1H), 4.00-3.95 (m, 2H), 3.84-3.81 (m, 5H), 3.66-3.61 (m, 3H), 3.47-3.45 (m, 2H), 3.12-3.05 (m, 1H), 1.84-1.80 (m, 1H), 1.73-1.68 (m, 1H), 1.57-1.51 (m, 2H), 1.28-1.24 (m, 1H).

Example 122

6-[(8-Morpholin-4-yl-5,11-dihydro-6H-pyrido[2,3-b][1,5]benzodiazepin-6-yl)carbonyl]spiro[3.3]heptan-2-one

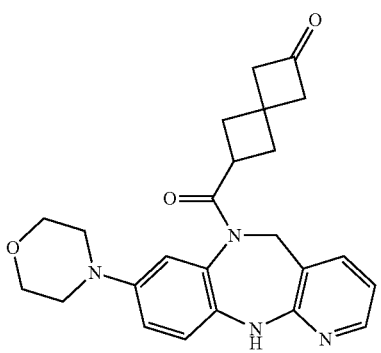 [SMILES: O=C1CC2(C1)CC(C(=O)N1Cc3cccnc3Nc3ccc(N4CCOCC4)cc31)C2]

To a mixture of hydrochloric acid (4.0 M in dioxane, 1.4 mL, 5.6 mmol) was added tert-butyl-8-morpholino-6-(6-oxospiro[3.3]heptane-2-carbonyl)-5H-benzo[b]pyrido[2,3-e][1,4]diazepine-11(6H)-carboxylate (0.029 g, 0.056 mmol) and the mixture was heated to 50° C. for 2 h. Upon cooling to room temperature, the mixture was concentrated under reduced pressure and the material was purified by reverse phase HPLC (ACN/water with 0.1% TFA for the modifier) to afford 6-[(8-morpholin-4-yl-5,11-dihydro-6H-pyrido[2,3-b][1,5]benzodiazepin-6-yl)carbonyl]spiro[3.3]heptan-2-one as the TFA salt. MS 419 (M+1). $^1$H NMR (600 MHz, DMSO-d$_6$) δ 9.99 (s, 1H), 8.03 (d, J=5.2 Hz, 1H), 7.73 (d, J=7.0 Hz, 1H), 7.18 (d, J=8.9 Hz, 1H), 6.96 (d, J=11.5 Hz, 1H), 6.89-6.76 (m, 2H), 5.24 (d, J=15.2 Hz, 1H), 3.94 (d, J=15.1 Hz, 1H), 3.71 (t, J=4.7 Hz, 4H), 3.19 (m, 1H), 3.10 (m, 2H), 3.07-3.02 (m, 2H), 2.99 (m, 1H), 2.89 (m, 2H), 2.81 (m, 1H), 2.49-2.44 (m, 1H), 2.26-2.19 (m, 1H), 2.02 (dd, J=11.3, 8.5 Hz, 1H), 1.72-1.63 (m, 1H).

Example 123

2-Methyl-6-[(8-morpholin-4-yl-5,11-dihydro-6H-pyrido[2,3-b][1,5]benzodiazepin-6-yl)carbonyl]spiro[3.3]heptan-2-ol

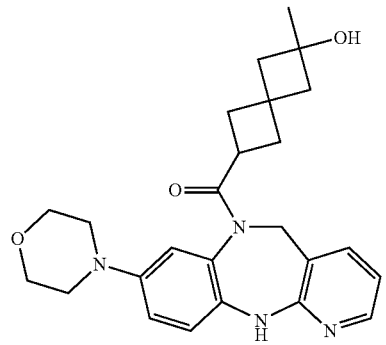 [SMILES: CC1(O)CC2(CC(C(=O)N3Cc4cccnc4Nc4ccc(N5CCOCC5)cc43)C2)C1]

To a mixture of tert-butyl 8-morpholino-6-(6-oxospiro[3.3]heptane-2-carbonyl)-5H-benzo[b]pyrido[2,3-e][1,4]diazepine-11(6H)-carboxylate (0.04 g, 0.08 mmol) in THF (1 mL) at 0° C. was added methylmagnesium bromide (3.0 M in diethyl ether, 257 μl, 0.771 mmol) dropwise. The mixture was allowed to slowly warm to room temperature and stirred for 18 h. The mixture was then carefully quenched with water and extracted with EtOAc. The organic layer was dried over sodium sulfate, filtered, concentrated under reduced pressure and purified by column chromatography on silica gel (0-20% MeOH/DCM) to afford 2-methyl-6-[(8-morpholin-4-yl-5,11-dihydro-6H-pyrido[2,3-b][1,5]benzodiazepin-6-yl)carbonyl]spiro[3.3]heptan-2-ol. MS 435 (M+1). $^1$H NMR (600 MHz, DMSO-d$_6$) δ 9.09 (s, 1H), 7.96 (s, 1H), 7.39 (d, J=6.5 Hz, 1H), 7.15 (d, J=8.5 Hz, 1H), 6.86 (s, 1H), 6.71-6.58 (m, 2H), 5.13 (d, J=14.8 Hz, 1H), 4.62-4.59 (m, 1H), 3.84 (d, J=15.1 Hz, 1H), 3.69 (s, 4H), 3.10-2.99 (m, 3H), 2.99-2.89 (m, 2H), 2.22-2.12 (m, 1H), 2.02-1.65 (m, 6H), 1.51-1.28 (m, 1H), 1.06-0.97 (m, 3H).

Example 124

3-[6-(6,7,8,9-Tetrahydro-5H-benzo[7]annulen-7-ylcarbonyl)-6,11-dihydro-5H-pyrido[2,3-b][1,5]benzodiazepin-8-yl]-1,3-oxazolidin-2-one

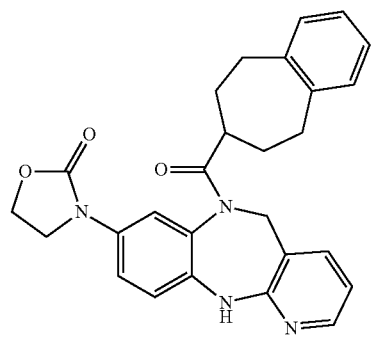 [SMILES: O=C1OCCN1c1ccc2c(c1)N(C(=O)C1CCc3ccccc3CC1)Cc1cccnc1N2]

Step 1: To a mixture of di-tert-butyl 8-bromo-5H-benzo[b]pyrido[2,3-e][1,4]diazepine-6,11-dicarboxylate (50 mg, 0.11 mmol), oxazolidin-2-one (18 mg, 0.21 mmol), copper (I) iodide (4 mg, 0.02 mmol), N,N'-dimethyl-1,2-cyclohexanediamine (6 mg, 0.04 mmol) and potassium phosphate tribasic (45 mg, 0.21 mmol) was added dioxane (1 mL) and the mixture was placed under a nitrogen atmosphere by performing 6 vacuum/nitrogen cycles. The reaction mixture was then heated to 100° C. for 48. Upon cooling to room temperature, the mixture was concentrated under reduced pressure. The residue was purified by column chromatography on silica gel (0-100% EtOAc/hexanes) to afford di-tert-butyl 8-(2-oxooxazolidin-3-yl)-5H-benzo[b]pyrido[2,3-e][1,4]diazepine-6,11-dicarboxylate. MS 483 (M+1).

Step 2: To a mixture of 6,7,8,9-tetrahydro-5H-benzo[7]annulene-7-carboxylic acid (4.7 mg, 0.025 mmol) in THF (1 mL) was added oxalyl chloride (0.041 ml, 0.041 mmol) and 1 drop of DMF. The mixture was stirred at RT for 30 minutes to afford an acid chloride mixture. To a separate flask, TFA (1 mL) was added to a mixture of di-tert-butyl 8-(2-oxooxazolidin-3-yl)-5H-benzo[b]pyrido[2,3-e][1,4]diazepine-6,11-dicarboxylate (10 mg, 0.021 mmol) in DCM (0.5 mL) and the mixture was stirred at RT for 30 minutes. The mixture was concentrated under reduced pressure and then dissolved in NMP (0.5 mL) and heated to 130° C. To this hot mixture was added the above acid chloride mixture. The mixture was then cooled down using an ice bath. The mixture was then concentrated under reduced pressure. The residue was purified by reverse phase HPLC (ACN/water with 0.1% TFA modifier) to afford 3-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one as TFA salt. MS 455 (M+1). $^1$H NMR (600 MHz, CDCl$_3$) δ 12.6 (s, 1H), 8.19 (s, 1H), 7.88-7.82 (m, 2H), 7.62 (d, J=10 Hz, 1H), 7.18-7.00 (m, 5H), 6.95-6.91 (m, 1H), 5.48 (d, J=15 Hz, 1H), 4.62-4.58 (m, 2H), 4.22-4.18 (m, 1H), 4.12-4.08 (m, 1H), 3.95 (d, J=15 Hz, 1H), 3.03-2.97 (m, 1H), 2.91-2.88 (m, 1H), 2.81-2.73 (m, 1H), 2.68-2.55 (m, 2H), 2.32-2.26 (m, 1H), 1.78-1.70 (m, 1H), 1.58-1.50 (m, 1H), 1.42-1.36 (m, 1H).

Example 125

4-Methyl-5-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one

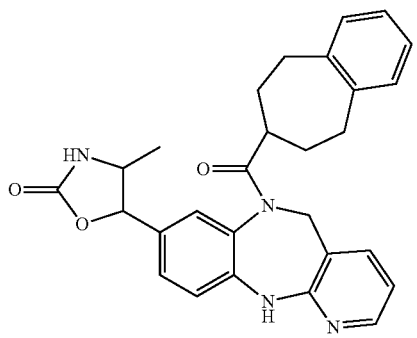 [SMILES: CC1NC(=O)OC1c1ccc2c(c1)N(C(=O)C1CCc3ccccc3CC1)Cc1cccnc1N2]

Step 1: To a mixture of di-tert-Butyl 8-bromo-5H-benzo[b]pyrido[2,3-e][1,4]diazepine-6,11-dicarboxylate (350 mg, 0.735 mmol), potassium trifluoro(vinyl)borate (197 mg, 1.47 mmol), PdCl$_2$(dppf) (108 mg, 0.147 mmol) and potassium carbonate (305 mg, 2.20 mmol) was added acetonitrile (4 mL) and water (1 mL). The mixture was placed under a nitrogen atmosphere by performing 6 vacuum/nitrogen cycles. The reaction mixture was then irradiated in the microwave to 100° C. for 1 hour. Upon cooling to room temperature, the mixture was diluted with ethyl acetate, washed with water, dried over magnesium sulfate, filtered and concentrated under reduced pressure. The residue was purified by column chromatography on silica gel (0-100% EtOAc/hexanes) to afford di-tert-butyl 8-vinyl-5H-benzo[b]pyrido[2,3-e][1,4]diazepine-6,11-dicarboxylate. MS 424 (M+1).

Step 2: To a mixture of di-tert-butyl 8-vinyl-5H-benzo[b]pyrido[2,3-e][1,4]diazepine-6,11-dicarboxylate (200 mg, 0.472 mmol) and osmium tetroxide (2.5 wt % in t-BuOH, 0.059 mL, 0.0047 mmol) in THF (3 mL) was added sodium periodate (1M in water, 1.04 mL, 1.04 mmol) drop wise. The mixture was stirred at RT for 2 hours. The mixture was quenched with saturated aqueous sodium sulfite and then extracted with EtOAc (3×10 mL). The combined organic extracts were dried over magnesium sulfate, filtered and concentrated under reduced pressure. The residue was purified by column chromatography on silica gel (0-100% EtOAc/hexanes) to afford di-tert-butyl 8-formyl-5H-benzo[b]pyrido[2,3-e][1,4]diazepine-6,11-dicarboxylate. MS 426 (M+1).

Step 3: To a mixture of di-tert-butyl 8-formyl-5H-benzo[b]pyrido[2,3-e][1,4]diazepine-6,11-dicarboxylate (160 mg, 0.376 mmol) in ethanol (3.7 mL) was added nitroethane (0.19 mL, 2.6 mmol) and sodium hydroxide (1M in water, 0.75 mL, 0.75 mmol). The mixture was stirred at 0° C. for 2 hour. The mixture was then quenched by the addition of acetic acid (0.33 M in water, 45 mg, 0.75 mmol) at 0° C. The mixture was diluted with ethyl acetate (10 mL), washed with water (2×10 mL), dried over anhydrous magnesium sulfate, filtered and concentrated under reduced pressure. The residue was purified by column chromatography on silica gel (0-100% EtOAc/hexanes) to afford di-tert-butyl 8-(1-hydroxy-2-nitropropyl)-5H-benzo[b]pyrido[2,3-e][1,4]diazepine-6,11-dicarboxylate as a solid. MS 501(M+1).

Step 4: To a mixture of di-tert-butyl 8-(1-hydroxy-2-nitropropyl)-5H-benzo[b]pyrido[2,3-e][1,4]diazepine-6,11-dicarboxylate (0.17 g, 0.34 mmol) in EtOH (3.4 mL) was added zinc (0.22 g, 3.4 mmol) followed by HCl (37% in H$_2$O, 0.57 mL, 3.4 mmol) at 0° C. under a nitrogen atmosphere. The resulting mixture was stirred at 0° C. for 1 hour and then allowed to warm to room temperature for 1 hour. The mixture was basified with aqueous NaOH (5N) at 0° C. to pH-9. The product was then extracted with EtOAc (5×10 mL). The combined organic layers were dried over magnesium sulfate, filtered and concentrated under reduced pressure to afford di-tert-butyl 8-(2-amino-1-hydroxypropyl)-5H-benzo[b]pyrido[2,3-e][1,4]diazepine-6,11-dicarboxylate. MS 471 (M+1).

Step 5: To a mixture of di-tert-butyl 8-(2-amino-1-hydroxypropyl)-5H-benzo[b]pyrido[2,3-e][1,4]diazepine-6,11-dicarboxylate (120 mg, 0.255 mmol) in CH$_2$Cl$_2$ (10 mL) was added DIPEA (0.22 mL, 1.3 mmol) followed by a mixture of triphosgene (76 mg, 0.26 mmol) in DCM (1 mL) at 0° C. The mixture was stirred at 0° C. for 10 minutes. The mixture was then diluted with DCM, washed with water, dried over magnesium sulfate, filtered and concentrated under reduced pressure. The residue was purified by column chromatography on silica gel (0-100% EtOAc/hexanes) to afford di-tert-butyl 8-(4-methyl-2-oxooxazolidin-5-yl)-5H-benzo[b]pyrido[2,3-e][1,4]diazepine-6,11-dicarboxylate. MS 497 (M+1).

Step 6: To a mixture of 6,7,8,9-tetrahydro-5H-benzo[7]annulene-7-carboxylic acid (13 mg, 0.068 mmol) in THF (1 mL) was added oxalyl chloride (0.056 ml, 0.11 mmol) and 1 drop of DMF. The mixture was stirred at RT for 30 minutes to give an acid chloride solution. To a separate flask containing a mixture of di-tert-butyl 8-(4-methyl-2-oxooxazolidin-5-yl)-5H-benzo[b]pyrido[2,3-e][1,4]diazepine-6,11-dicarboxylate (28 mg, 0.056 mmol) in DCM (0.5 mL) was added TFA (1 mL) at room temperature. The reaction mixture was stirred at RT for 30 minutes. The mixture was concentrated under reduced pressure and was then dissolved in NMP (0.5 mL) and heated to 130° C. To this hot solution was added the above acid chloride mixture. The mixture was then cooled down in an ice bath. The mixture was then concentrated under reduced pressure and the residue was purified by reverse phase HPLC (ACN/water with 0.1% TFA modifier) to afford 4-methyl-5-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one as a TFA salt. MS 469 (M+1). $^1$H NMR (600 MHz, CDCl$_3$) δ 12.78 (s, 1H), 7.92-7.88 (m, 2H), 7.71-7.68 (m, 1H), 7.41-7.32 (m, 2H), 7.12-7.06 (m, 3H), 7.02-6.95 (m, 2H), 5.48-5.43 (m, 1H), 5.32-5.24 (m, 1H), 5.14-5.11 (m, 1H), 3.94-3.90 (m, 1H), 3.86-3.73 (m, 1H), 2.92-2.78 (m, 2H), 2.73-2.58 (m, 2H), 2.52-2.40 (m, 1H), 2.21-2.18 (m, 1H), 1.78-1.70 (m, 1H), 1.44 (s, 3H), 1.40-1.30 (m, 1H).

Example 126

(4R)-4-(1-Methylethyl)-3-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one

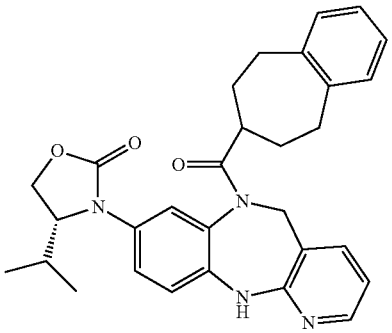 [SMILES: CC(C)[C@@H]1COC(=O)N1c1ccc2c(c1)N(C(=O)C1CCc3ccccc3CC1)Cc1cccnc1N2]

To a mixture of (8-bromo-5H-benzo[b]pyrido[2,3-e][1,4]diazepin-6(11H)-yl)(6,7,8,9-tetrahydro-5H-benzo[7]annulen-7-yl)methanone (25 mg, 0.056 mmol), (R)-4-isopropyloxazolidin-2-one (14 mg, 0.11 mmol), copper(I) iodide (2 mg, 0.01 mmol), N,N'-dimethyl-1,2-cyclohexanediamine (3 mg, 0.02 mmol) and potassium phosphate tribasic (24 mg, 0.11 mmol) was added dioxane (1 mL). The mixture was placed under a nitrogen atmosphere by performing 6 vacuum/nitrogen cycles and the mixture was then irradiated in the microwave to 120° C. for 2 hours. Upon cooling to room temperature, the mixture was concentrated under reduced pressure and the residue was purified by reverse phase HPLC (ACN/water with 0.1% TFA modifier) to afford (4R)-4-(1-methylethyl)-3-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one as the TFA salt. MS 497 (M+1). $^1$H NMR (600 MHz, CDCl$_3$) δ 12.74-12.66 (m, 1H), 7.98-7.82 (m, 2H), 7.67-7.63 (m, 1H), 7.22-7.17 (m, 1H), 7.15-7.05 (m, 4H), 6.94-6.92 (m, 1H), 5.48-5.42 (m, 1H), 4.52-4.48 (m, 2H), 4.32-4.28 (m, 1H), 4.00-3.92 (m, 1H), 2.98-2.80 (m, 2H), 2.65-2.55 (m, 2H), 2.23-1.86 (m, 2H), 1.80-1.68 (m, 1H), 1.58-1.54 (m, 1H), 1.40-1.30 (m, 1H), 1.02-0.95 (m, 3H), 0.92-0.86 (m, 3H).

Example 127

(R)-(2,3-Dihydrobenzo[b][1,4]dioxin-2-yl)(8-(3,3,3-trifluoropropyl)-5,11-dihydro-6H-benzo[b]pyrido[2,3-e][1,4]diazepin-6-yl)methanone

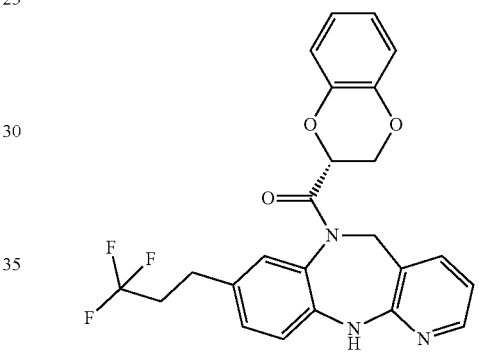

To a vial was added (R)-(8-bromo-5H-dibenzo[b,e][1,4]diazepin-10(11H)-yl)(2,3-dihydrobenzo[b][1,4]dioxin-2-yl)methanone (25 mg, 0.057 mmol), potassium (3,3,3-trifluoroprop-1-yl)trifluoroborate (26 mg, 0.11 mmol), RuPhos G1 pre-catalyst (4.2 mg, 5.7 μmol), and cesium carbonate (56 mg, 0.17 mmol). The vial was evacuated and backfilled with N$_2$ (3×). Degassed toluene (500 μL) and water (50 μL) were added and the resulting reaction mixture was heated to 80° C. overnight. The reaction was allowed to cool to room temperature, diluted with EtOAc (4 mL) and washed with water (2 mL). The organic layer was separated and concentrated under reduced pressure. The residue was purified by reverse phase HPLC (ACN/water with 0.1% TFA modifier) to afford (R)-(2,3-dihydrobenzo[b][1,4]dioxin-2-yl)(8-(3,3,3-trifluoropropyl)-5,11-dihydro-6H-benzo[b]pyrido[2,3-e][1,4]diazepin-6-yl)methanone as a TFA salt. MS: 456 (M+1). $^1$H NMR (DMSO-d$_6$, 500 MHz): δ 9.57 (d, J=9.6 Hz, 1H), 8.10-8.00 (m, 1H), 7.51-7.00 (m, 4H), 6.94-6.71 (m, 5H), 5.28 (t, J=14.7 Hz, 1H), 4.22 (dd, J=11.9, 6.6 Hz, 1H), 4.02 (dd, J=15.0, 7.2 Hz, 1H), 3.93 (dd, J=15.0, 7.5 Hz, 1H), 3.73 (m, 1H) 2.76 (m, 2H), 2.54 (m, 2H).

Example 128

(R)-(2,3-Dihydrobenzo[b][1,4]dioxin-2-yl)(8-(trifluoromethyl)-5,11-dihydro-6H-benzo[b]pyrido[2,3-e][1,4]diazepin-6-yl)methanone

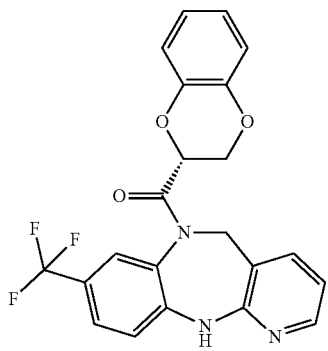 [SMILES: O=C([C@H]1COc2ccccc2O1)N1Cc2cccnc2Nc2ccc(C(F)(F)F)cc21]

To a vial in a glove box was added (R)-(2,3-dihydrobenzo[b][1,4]dioxin-2-yl)(8-(4,4,5,5-tetramethyl-1,3,2-dioxaborolan-2-yl)-5H-benzo[b]pyrido[2,3-e][1,4]diazepin-6(11H)-yl)methanone (20 mg, 0.041 mmol), Cu(phen)CF$_3$ (19 mg, 0.062 mmol), KF (7.4 mg, 0.12 mmol) and degassed anhydrous DMF (1 mL). The resulting reaction mixture was then heated to 70° C. for 1 h. The reaction was allowed to cool to room temperature and filtered. The filtrate was diluted with EtOAc (4 mL) and washed with ammonia (2N in water, 2×2 mL). The organic phase was separated and concentrated under reduced pressure. The residue was purified by reverse phase HPLC (ACN/water with 0.1% TFA modifier) to afford (R)-(2,3-dihydrobenzo[b][1,4]dioxin-2-yl)(8-(trifluoromethyl)-5,11-dihydro-6H-benzo[b]pyrido[2,3-e][1,4]diazepin-6-yl)methanone as a TFA salt. MS: 428 (M+1). $^1$H NMR (DMSO-d$_6$, 500 MHz): δ 10.00 (s, 1H), 8.10 (dd, J=5.2, 1.7 Hz, 1H), 7.91 (s, 1H), 7.58-7.52 (m, 2H), 6.99-6.73 (m, 5H), 6.43 (dd, J=7.7, 5.2 Hz, 1H), 5.27 (dd, J=15.0, 4.5 Hz, 1H), 4.9-4.7 (m, 2H), 4.4-4.0 (m, 2H).

Examples 129-130

(8-((1R,4R)-2-Oxa-5-azabicyclo[2.2.2]octan-5-yl)-5,11-dihydro-6H-benzo[b]pyrido[2,3-e][1,4]diazepin-6-yl)((1R,5S)-9-(2,2,2-trifluoroethyl)-3-oxa-9-azabicyclo[3.3.1]nonan-7-yl)methanone and (8-((1S,4S)-2-Oxa-5-azabicyclo[2.2.2]octan-5-yl)-5,11-dihydro-6H-benzo[b]pyrido[2,3-e][1,4]diazepin-6-yl)((1R,5S)-9-(2,2,2-trifluoroethyl)-3-oxa-9-azabicyclo[3.3.1]nonan-7-yl)methanone

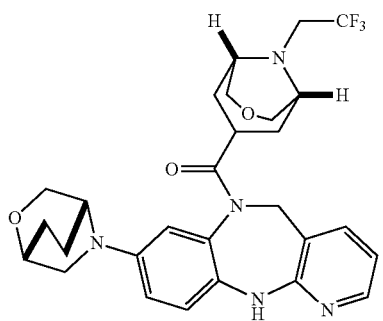

-continued

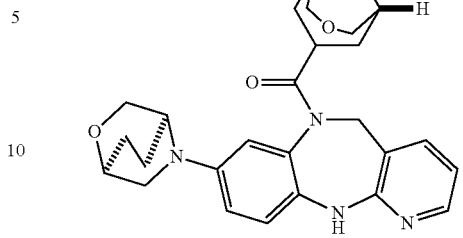

Step 1: To a vial was added 5-(6,11-dihydro-5H-benzo[b]pyrido[2,3-e][1,4]diazepin-8-yl)-2-oxa-5-azabicyclo[2.2.2]octane (100 mg, 0.324 mmol), (1R,5S)-9-(tert-butoxycarbonyl)-3-oxa-9-azabicyclo[3.3.1]nonane-7-carboxylic acid (88 mg, 0.32 mmol), 2,2,2-trichloroacetonitrile (163 μL, 1.62 mmol), and polymer-supported triphenylphosphine (326 mg, 1.18 mmol). Acetonitrile (5.4 mL) was added and the vial was sealed and bubbled with nitrogen. The reaction mixture was heated to 100° C. under microwave irridation for 20 min. The reaction mixture was cooled to room temperature and filtered. The filtrate was concentrated under reduced pressure to give crude tert-butyl (1R,5S)-7-(8-(2-oxa-5-azabicyclo[2.2.2]octan-5-yl)-6,11-dihydro-5H-benzo[b]pyrido[2,3-e][1,4]diazepine-6-carbonyl)-3-oxa-9-azabicyclo[3.3.1]nonane-9-carboxylate as a solid. MS: 562 (M+1).

Step 2: To a mixture of (1R,5S)-tert-butyl 7-(8-(2-oxa-5-azabicyclo[2.2.2]octan-5-yl)-6,11-dihydro-5H-benzo[b]pyrido[2,3-e][1,4]diazepine-6-carbonyl)-3-oxa-9-azabicyclo[3.3.1]nonane-9-carboxylate (0.182 g, 0.324 mmol) in DCM (2 mL) was added TFA (0.62 mL, 8.1 mmol). The reaction was stirred at room temperature for 30 min. The reaction mixture was concentrated under reduced pressure to afford (8-(2-Oxa-5-azabicyclo[2.2.2]octan-5-yl)-5,11-dihydro-6H-benzo[b]pyrido[2,3-e][1,4]diazepin-6-yl)((1R,5S)-3-oxa-9-azabicyclo[3.3.1]nonan-7-yl)methanone as a solid. MS: 462 (M+1).

Step 3: To a mixture of (8-(2-oxa-5-azabicyclo[2.2.2]octan-5-yl)-5H-benzo[b]pyrido[2,3-e][1,4]diazepin-6(11H)-yl)((1R,5S)-3-oxa-9-azabicyclo[3.3.1]nonan-7-yl)methanone TFA salt (186 mg, 0.324 mmol) in ethanol (650 μL) was added sodium bicarbonate (272 mg, 3.24 mmol), and 2,2,2-trifluoroethyl trifluoromethanesulfonate (150 mg, 0.648 mmol). The mixture was heated to 80° C. for 18 h. Upon cooling to room temperature, more sodium bicarbonate (136 mg, 1.62 mmol) and 2,2,2-trifluoroethyl trifluoromethanesulfonate (75 mg, 0.324 mmol) were added. The mixture was heated to 80° C. for another 4 hours. The mixture was allowed to cool to room temperature and was then quenched with water. The mixture was washed with EtOAc (3×). The combined organic layers were washed with brine, dried over anhydrous sodium sulfate, filtered, and concentrated under reduced pressure. The residue was purified by reverse phase HPLC (ACN/water with 0.05% TFA modifier) to afford racemic [8-(2-oxa-5-azabicyclo[2.2.2]oct-5-yl)-5,11-dihydro-6H-pyrido[2,3-b][1,5]benzodiazepin-6-yl][(1R,5S)-9-(2,2,2-trifluoroethyl)-3-oxa-9-azabicyclo[3.3.1]non-7-yl]methanone. MS: 544 (M+1). The racemic mixture was purified by chiral SFC (CD column, 50% MeOH (0.2% NH$_4$OH)/CO$_2$) to afford 8-((1R,4R)-2-oxa-5-azabicyclo[2.2.2]octan-5-yl)-5,11-dihydro-6H-benzo[b]pyrido[2,3-e][1,4]diazepin-6-yl)((1R,5S)-9-(2,2,2-trifluoroethyl)-3-oxa-9-azabicyclo[3.3.1]nonan-7-yl)methanone and (8-((1 S,4S)-2-oxa-5-azabicyclo[2.2.2]oct-5-yl)-5,11-dihydro-6H-benzo[b]pyrido[2,3-e][1,4]diazepin-6-yl)((1R,5S)-9-(2,2,2-trifluoroethyl)-3-oxa-9-azabicyclo[3.3.1]nonan-7-yl)methanone.

Isomer 1, first eluting: MS: 544 (M+1) $^1$H NMR (500 MHz, CD$_3$OD) δ 7.97 (d, J=4.7 Hz, 1H), 7.50 (d, J=7.1 Hz, 1H), 7.12 (dd, J=8.9, 4.9 Hz, 1H), 6.78-6.67 (m, 2H), 6.63 (dd, J=2.9, 1.1 Hz, 1H), 5.32 (dd, J=14.9, 3.6 Hz, 1H), 4.31-4.17 (m, 2H), 4.16-4.11 (m, 1H), 4.10-3.99 (m, 3H), 3.89-3.77 (m, 2H), 3.76-3.63 (m, 2H), 3.41 (t, J=10.9 Hz, 1H), 3.33-3.09 (m, 3H), 2.75 (s, 1H), 2.51 (s, 1H), 2.26-2.19 (m, 1H), 2.15 (t, dd, J=12.5, 8.9 Hz, 2H), 1.96 (t, J=11.4 Hz, 1H), 1.80-1.68 (m, 1H), 1.65-1.50 (m, 2H), 1.20-1.10 (m, 1H) Isomer 2, second eluting: MS: 544 (M+1). $^1$H NMR (500 MHz, CD$_3$OD) δ 8.00-7.95 (m, 1H), 7.50 (d, J=7.1 Hz, 1H), 7.12 (dd, J=8.9, 4.9 Hz, 1H), 6.78-6.68 (m, 2H), 6.72-6.61 (m, 1H), 5.32 (dd, J=15.0, 3.6 Hz, 1H), 4.40-4.22 (m, 2H), 4.17 (td, J=6.1, 2.8 Hz, 1H), 4.10-3.99 (m, 2H), 3.90-3.75 (m, 3H), 3.76-3.63 (m, 2H), 3.41 (t, J=10.9 Hz, 1H), 3.33-3.09 (m, 3H), 2.75 (s, 1H), 2.55-2.48 (m, 1H), 2.35-2.25 (m, 1H), 2.15 (dd, J=13.2, 8.5 Hz, 2H), 1.95 (t, J=11.6 Hz, 1H), 1.84-1.74 (m, 1H), 1.70-1.55 (m, 2H), 1.23-1.12 (m, 1H).

Example 131

Cis[8-(morpholin-4-yl)-5,11-dihydro-6H-pyrido[2,3-b][1,5]benzodiazepin-6-yl][3-(2,2,2-trifluoroethyl)-3-azabicyclo[3.1.1]hept-6-yl]methanone

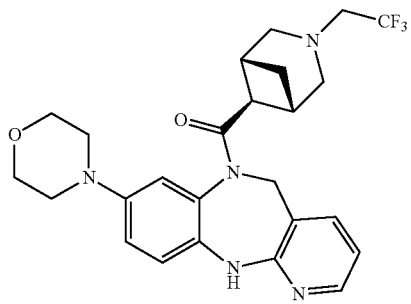 [SMILES: O=C([C@@H]1[C@@H]2C[C@H]1CN(CC(F)(F)F)C2)N1Cc2cccnc2Nc2ccc(N3CCOCC3)cc21]

Example 131 was made using the procedure described for Examples 129-130. MS: 488 (M+1).

R132H IDH1 Enzymatic Assay

Each test compound (10 mM stock in DMSO) is diluted in DMSO to make a 10-point, 3-fold dilution series. 125 nL of each dilution or DMSO alone is dispensed to a 384-well Greiner Lumitrac 200 assay plate using an Echo® Liquid Handler. To each well of the plate is added 20 uL of enzyme in assay buffer or assay buffer alone. Assay buffer consists of 50 mM sodium phosphate, pH 7.0, 50 mM magnesium chloride, 50 mM sodium chloride, and 0.01% (w/v) bovine serum albumin. When present, the R132H mutant IDH1 enzyme is at a working concentration of 1.875 nM (final concentration in assay of 1.5 nM). The assay plate is allowed to incubate for 30 minutes at room temperature and 5 uL of 5× substrate mixture (2.5 uM nicotinamide adenine dinucleotide phosphate, 100 uM adenosine diphosphate, 7.5 mM glyceraldehyde-3-phosphate, 7.5 ug/mL of spinach glyceraldehyde-3-phosphate dehydrogenase, 25 nM phosphoglycerate kinase, and 5 mM alpha-ketoglutarate in assay buffer) is added to all wells. The reaction plate is incubated for 60 minutes followed by addition of 25 uL of Promega Kinase-GLO reagent to all wells and 10-minute incubation.

Luminescence is measured using a PerkinElmer Envision plate reader. The percent activity of each dilution is determined as the ratio of background corrected signal to the background corrected signal of wells receiving only DMSO. IC$_{50}$ values are determined by fitting percent activity data to a four-parameter logistic dose response equation. The IC$_{50}$ values of the exemplified compounds are included in the tables above in Examples section.

Using the above biological assay, all compounds in the examples have IC$_{50}$ of about 1 nM to about 40,000 nM, or more specifically, about 1 nM to about 20,000 nM, or even more specifically, about 5 nM to about 15,000 nM, or even more specifically, about 5 nM to about 10,000 nM, or even more specifically, about 5 nM to about 5,000 nM, or still more specifically, about 5 nM to about 1,000 nM. Such a result is indicative of the intrinsic activity of the compounds in use as an inhibitor of a mutant IDH1 enzyme. Specific IC$_{50}$ activity data for the exemplified compounds disclosed herein is provided in the following table.

| Ex. No. | IC$_{50}$, nM |
| --- | --- |
| 1 | 1050 |
| 2 | 226 |
| 3 | 3 |
| 4 | 7676 |
| 5 | 8483 |
| 6 | 18190 |
| 7 | 1856 |
| 8 | 1047 |
| 9 | 39390 |
| 10 | 212 |
| 11 | 155 |
| 12 | 1413 |
| 13 | 3 |
| 14 | 630 |
| 15 | 26370 |
| 16 | 8854 |
| 17 | 1753 |
| 18 | 218 |
| 19 | 148 |
| 20 | 99 |
| 21 | 440 |
| 22 | 2169 |
| 23 | 611 |
| 24 | 1061 |
| 25 | 864 |
| 26 | 860 |
| 27 | 1440 |
| 28 | 563 |
| 29 | 1047 |
| 30 | 1767 |
| 31 | 225 |
| 32 | 97 |
| 33 | 1753 |
| 34 | 1522 |
| 35 | 9482 |
| 36 | 2314 |
| 37 | 2365 |
| 38 | 393 |
| 39 | 624 |
| 40 | 171 |
| 41 | 95 |
| 42 | 87 |
| 43 | 626 |
| 44 | 626 |
| 45 | 123 |
| 46 | 1581 |
| 47 | 11010 |
| 48 | 1867 |
| 49 | 2479 |
| 50 | 2477 |
| 51 | 667 |

-continued

| Ex. No. | IC$_{50}$, nM |
|---|---|
| 52 | 257 |
| 53 | 1692 |
| 54 | 6137 |
| 55 | 1073 |
| 56 | 351 |
| 57 | 424 |
| 58 | 9931 |
| 59 | 14190 |
| 60 | 1461 |
| 61 | 4064 |
| 62 | 9 |
| 63 | 3 |
| 64 | 4 |
| 65 | 3 |
| 66 | 12 |
| 67 | 1767 |
| 68 | 5 |
| 69 | 1905 |
| 70 | 77 |
| 71 | 85 |
| 72 | 400 |
| 73 | 700 |
| 74 | 79 |
| 75 | 69 |
| 76 | 17 |
| 77 | 60 |
| 78 | 309 |
| 79 | 64 |
| 80 | 176 |
| 81 | 18 |
| 82 | 20 |
| 83 | 48 |
| 84 | 56 |
| 85 | 64 |
| 86 | 1915 |
| 87 | 1504 |
| 88 | 1037 |
| 89 | 4200 |
| 90 | 3845 |
| 91 | 5787 |
| 92 | 4516 |
| 93 | 12250 |
| 94 | 635 |
| 95 | 91 |
| 96 | 117 |
| 97 | 141 |
| 98 | 3608 |
| 99 | 5 |
| 100 | 3 |
| 101 | 5 |
| 102 | 6 |
| 103 | 3 |
| 104 | 5 |
| 105 | 36 |
| 106 | 3 |
| 107 | 5 |
| 108 | 6 |
| 109 | 160 |
| 110 | 18 |
| 111 | 1873 |
| 112 | 22550 |
| 113 | 16350 |
| 114 | 894 |
| 115 | 429 |
| 116 | 5 |
| 117 | 22 |
| 118 | 9 |
| 119 | 22 |
| 120 | 4 |
| 121 | 36720 |
| 122 | 5126 |
| 123 | 5961 |
| 124 | 4 |
| 125 | 3 |
| 126 | 3 |
| 127 | 120 |
| 128 | 170 |

-continued

| Ex. No. | IC$_{50}$, nM |
|---|---|
| 129 | 6 |
| 130 | 5 |
| 131 | 114 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of formula (I):

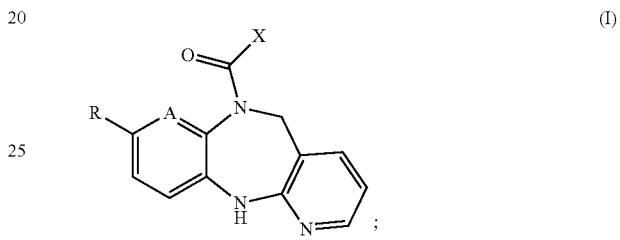

wherein A is —C(R$^1$)═ or —N═, and R$^1$ is hydrogen or hydroxyl;
X is a polycyclic ring selected from the group consisting of:

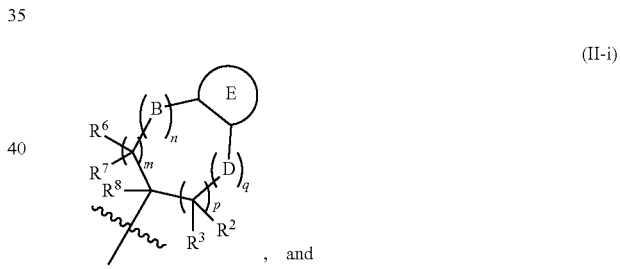

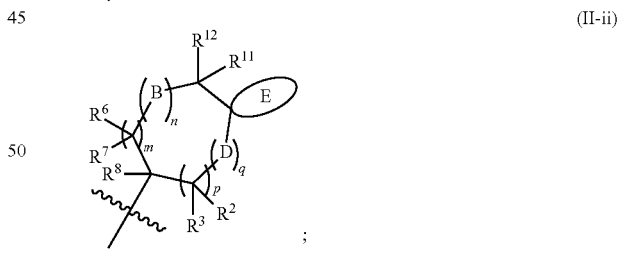

B is —C(R$^9$)(R$^{10}$)—, —N(R$^{10}$)—, —O—, —S— or —S(O)$_2$—;
D is —C(R$^4$)(R$^5$)—, —N(R$^5$)—, —O— or —S—;
m is 0 or 1; n is 0 or 1; p is 0 or 1; q is 0 or 1;
the E ring is a C$_{3-6}$carbocyclic ring or a 3-6 membered saturated, partially unsaturated or aromatic heterocyclic ring containing 1-2 heteroatoms independently selected from O, S and N;
the E ring is optionally substituted with one to four substituents independently selected from R$^b$;
and optionally, the E ring is further fused to another 4-6 membered carbocyclic ring;

R is selected from the group consisting of:
(1) halogen,
(2) —CN, and
(3) —(C=O)$_t$—R$^a$, wherein t is 0 or 1;

R$^2$ and R$^3$ together form an oxo; or alternatively, each occurrence of R$^2$ and R$^3$ is independently selected from the group consisting of:
(1) hydrogen,
(2) C$_{1-6}$alkyl, and
(3) —O—C$_{1-6}$alkyl;

each occurrence of R$^4$, R$^6$, R$^7$, R$^9$, R$^{11}$ and R$^{12}$ is independently selected from the group consisting of:
(1) halogen,
(2) —CN, and
(3) —(C=O)$_t$—R$^a$, wherein t is 0 or 1;

each occurrence of R$^5$ and R$^{10}$ is independently selected from the group consisting of:
(1) hydrogen, and
(2) C$_{1-6}$alkyl;

R$^8$ is selected from the group consisting of:
(1) hydrogen,
(2) —CN, and
(3) C$_{1-6}$alkyl;

each occurrence of R$^a$ is independently selected from the group consisting of:
(1) hydrogen,
(2) —(O)$_t$—R$^d$, wherein t is 0 or 1; R$^d$ is selected from the group consisting of (a) hydrogen, (b) C$_{1-6}$alkyl, (c) C$_{3-7}$cycloalkyl, and (d) phenyl;
  wherein each of the C$_{1-6}$alkyl of (b) and C$_{3-7}$cycloalkyl of (c) is optionally substituted with one to four substituents independently selected from R$^b$,
(3) —NR$^x$R$^y$, wherein each of R$^x$ and R$^y$ is independently selected from the group consisting of (a) hydrogen, (b) C$_{1-6}$alkyl, (c) C$_{3-6}$cycloalkyl, (d) —O—C$_{1-6}$alkyl, (e) phenyl optionally substituted with one to four halogens, and (f) heterocyclyl;
  wherein the C$_{1-6}$alkyl of (b) is optionally substituted with one to four substituents independently selected from halogen, —O—C$_{1-4}$alkyl, C$_{3-6}$cycloalkyl, and heterocyclyl; and
  the C$_{3-6}$cycloalkyl of (c) is optionally substituted with one to four substituents independently selected from halogen, —O—C$_{1-4}$alkyl, C$_{3-6}$cycloalkyl, heterocyclyl, and C$_{1-4}$alkyl, which is optionally substituted with one to four halogens,
  the heterocyclyl of (f) is optionally substituted with one to four substituents independently selected from halogen, C$_{1-4}$alkyl, —O—C$_{1-4}$alkyl, C$_{3-6}$cycloalkyl, and heterocyclyl;
(4) C$_{2-6}$alkenyl, optionally substituted with one to four substituents independently selected from R$^b$,
(5) C$_{5-6}$cycloalkenyl, optionally substituted with one to four substituents independently selected from R$^b$,
(6) aryl, optionally substituted with one to four substituents independently selected from R$^b$, and
(7) heterocyclyl, optionally substituted with one to four substituents independently selected from R$^b$;

each occurrence of R$^b$ is independently selected from the group consisting of:
(1) halogen,
(2) —CN,
(3) oxo,
(4) —(O)$_t$—R$^d$, wherein t is 0 or 1; R$^d$ is selected from the group consisting of (a) hydrogen, (b) C$_{1-6}$alkyl, (c) C$_{3-7}$cycloalkyl, and (d) heterocyclyl;
  wherein the C$_{1-6}$alkyl of (b) is optionally substituted with one to four substituents independently selected from (i) halogen, (ii) hydroxyl, (iii) —O—C$_{1-6}$alkyl, (iv) C$_{3-6}$cycloalkyl optionally substituted with 1-3 halogens, (v) —NR$^x$R$^y$, wherein each of R$^x$ and R$^y$ is independently selected from the group consisting of hydrogen, C$_{1-6}$alkyl, C$_{3-6}$cycloalkyl, phenyl optionally substituted with one to four halogens, and heterocyclyl, and (vi) heterocyclyl;
  the C$_{3-7}$cycloalkyl of (c) is optionally substituted with one to four substituents independently selected from (i) halogen, and (ii) C$_{1-6}$alkyl, which is optionally substituted with one to four halogens, and (iii) —CN; and
  the heterocyclyl of (d) is optionally substituted with one to four substituents independently selected from (i) halogen, (ii) hydroxyl, (iii) oxo, (iv) C$_{1-6}$alkyl optionally substituted with one to four halogens, (v) —O—C$_{1-6}$alkyl, (vi) heterocyclyl optionally substituted with halogen or hydroxyl, and (vii) —NR$^j$R$^k$;
  wherein each of R$^j$ and R$^k$ is independently selected from the group consisting of hydrogen and C$_{1-6}$alkyl;
(5) —(C=O)$_t$—R$^c$, wherein t is 0 or 1; R$^c$ is selected from the group consisting of hydrogen, hydroxyl, C$_{1-6}$alkyl, C$_{2-6}$alkenyl, —O—C$_{1-6}$alkyl, —NR$^x$R$^y$, and heterocyclyl;
  wherein each of R$^x$ and R$^y$ is independently selected from the group consisting of (a) hydrogen, (b) C$_{1-6}$alkyl, (c) C$_{2-6}$alkenyl, (d) C$_{3-6}$cycloalkyl, (e) phenyl optionally substituted with one to four halogens, and (f) heterocyclyl;
  wherein the C$_{1-6}$alkyl of (b) is optionally substituted with one to four substituents independently selected from halogen, —O—C$_{1-4}$alkyl, C$_{3-6}$cycloalkyl, heterocyclyl, and —(C=O)—NR$^j$R$^k$, wherein each of R$^j$ and R$^k$ is independently hydrogen or C$_{1-6}$alkyl;
  the C$_{3-6}$cyclolkyl of (d) is optionally substituted with one to four substituents independently selected from halogen and C$_{1-4}$alkyl, which is optionally substituted with one to four halogens, and
  the heterocyclyl of (f) is optionally substituted with one to four substituents independently selected from halogen, —CN, C$_{1-6}$alkyl, and —O—C$_{1-6}$alkyl;
(6) C$_{2-6}$alkenyl; and
(7) phenyl, optionally substituted with one to four substituents independently selected from halogen, C$_{1-6}$alkyl, and —O—C$_{1-6}$alkyl;

or a pharmaceutically acceptable salt thereof.

2. The compound of claim 1 having the following formula:

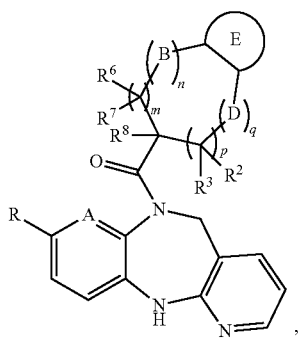
(Ia)

wherein A is —CH=, —C(OH)=, or —N=;
B is —CH(R$^9$)—, —NH—, or —O—;
D is —CH(R$^4$)—, —NH—, or —O—; and
the E ring is a C$_{3-6}$ carbocyclic ring or a 3-6 membered saturated, partially unsaturated or aromatic heterocyclic ring containing 1-2 heteroatoms independently selected from O, S and N; and the E ring is optionally substituted with one to four substituents independently selected from R$^b$;

or a pharmaceutically acceptable salt thereof.

3. The compound of claim 2 selected from the group consisting of:

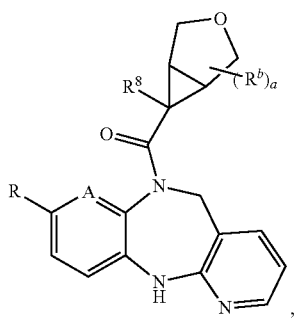
(Ia-i)

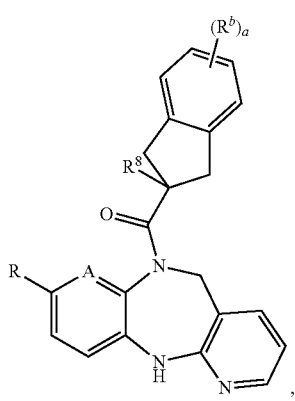
(Ia-ii)

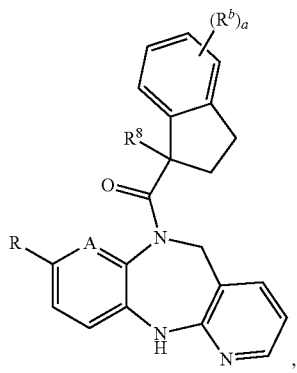
(Ia-iii)

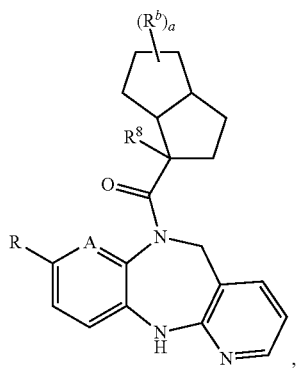
(Ia-iv)

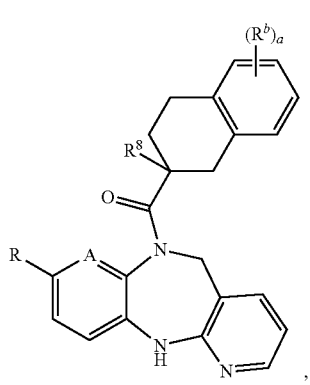
(Ia-v)

(Ia-vi)

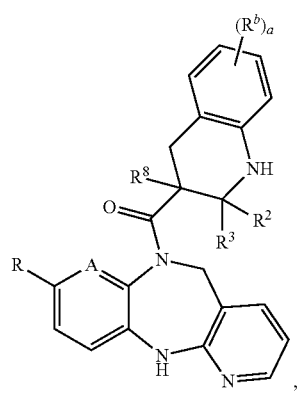
(Ia-vii)
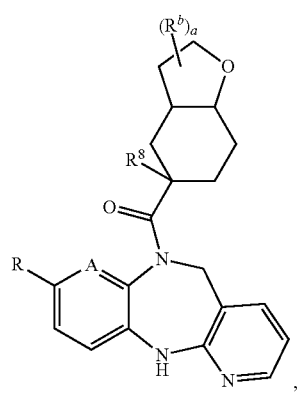
(Ia-viii)
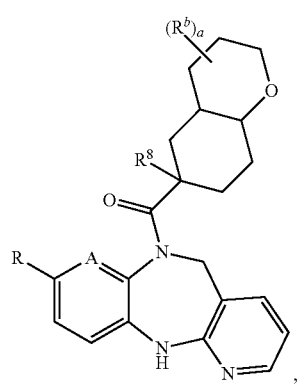
(Ia-ix)
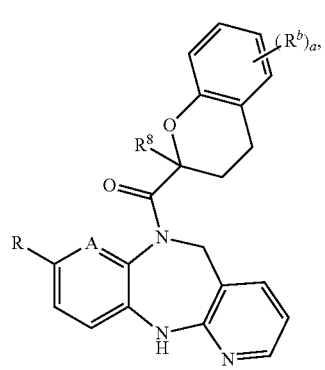
(Ia-x)
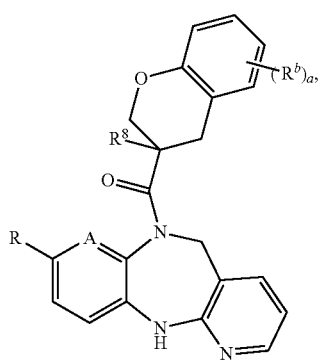
(Ia-xi)
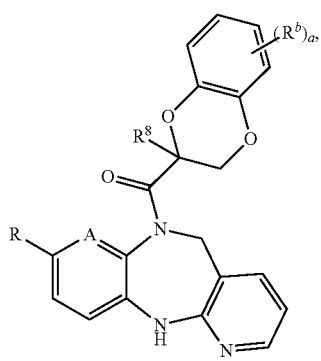
(Ia-xii)
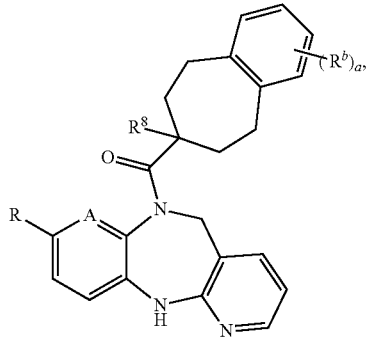
(Ia-xiii)
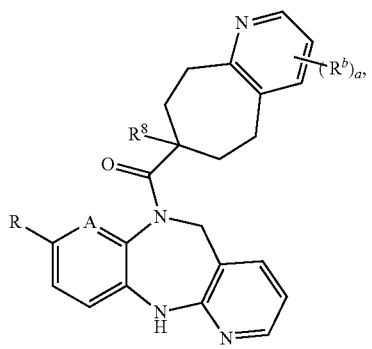
(Ia-xiv)

-continued

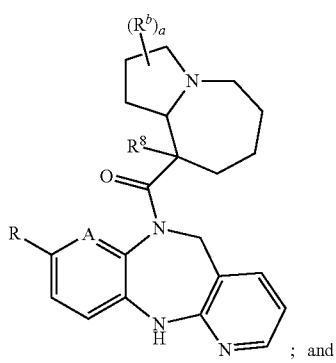

(Ia-xv)

; and

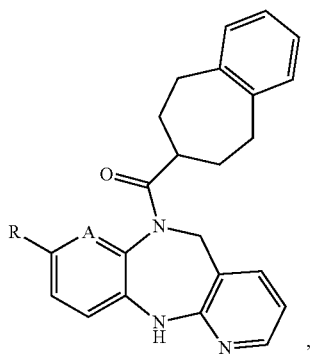

(Ia-xvi)

wherein A is —CH=, —C(OH)=, or —N=; and

R$^2$ and R$^3$ together form an oxo; or alternatively, each of R$^2$ and R$^3$ is hydrogen;

a is 0, 1 or 2; when a is 2, the two R$^b$ substituents are attached to the same or different substitutable positions on fused ring;

or a pharmaceutically acceptable salt thereof.

4. The compound of claim 3 of the following formula:

(Ia-xvi)

wherein A is —CH=, —C(OH)=, or —N=;

or a pharmaceutically acceptable salt thereof.

5. The compound of claim 1 having the following formula:

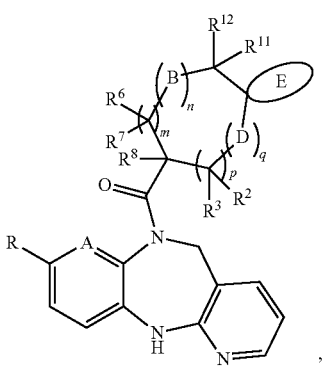

(Ib)

wherein A is —CH=, —C(OH)=, or —N=; and the E ring is a C$_{3-6}$carbocyclic ring or a 3-6 membered saturated, partially unsaturated or aromatic heterocyclic ring containing 1 or 2 heteroatoms independently selected from O, S and N; and the E ring is optionally substituted with one to three substituents independently selected from R$^b$;

or a pharmaceutically acceptable salt thereof.

6. The compound of claim 5, wherein the E ring is selected from the group consisting of:

azetidinyl,
C$_{3-6}$cycloalkyl,
oxetanyl,
phenyl,
pyridinyl,
pyrrolidinyl,
tetrahydrofuranyl, and
tetrahydropyranyl;

or a pharmaceutically acceptable salt thereof.

7. The compound of claim 6 having the following formula:

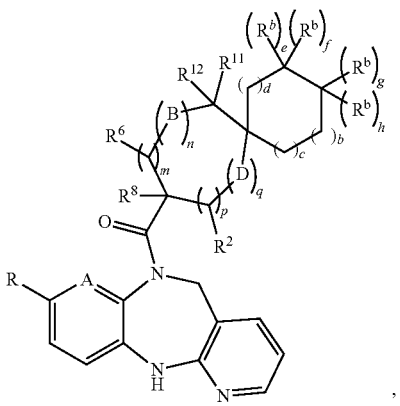

(Ib-i)

wherein A is —CH=, —C(OH)=, or —N=; and b is 0 or 1; c is 0 or 1; d is 0 or 1;

e is 0 or 1; f is 0 or 1; g is 0 or 1; h is 0 or 1;

or a pharmaceutically acceptable salt thereof.

8. The compound of claim 6, selected from the group consisting of:

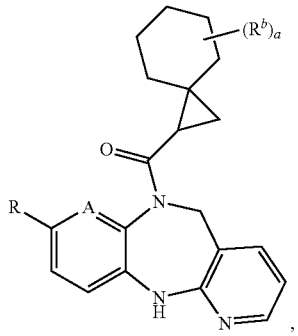
(Ib-ii)

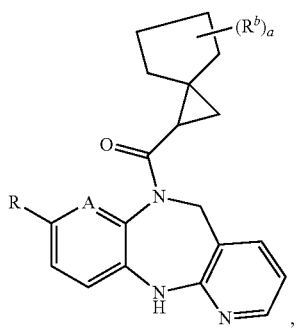
(Ib-iii)

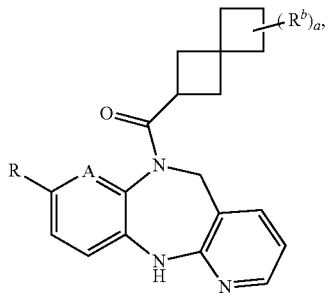
(Ib-iv)

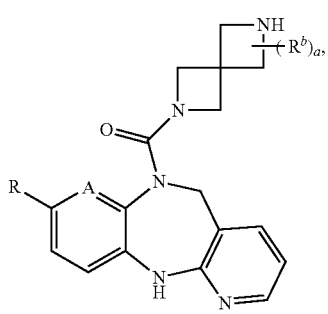
(Ib-v)

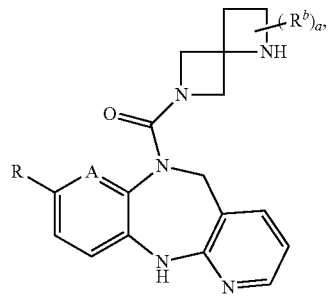
(Ib-vi)

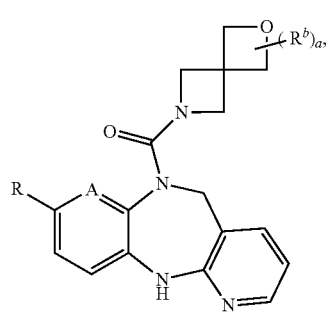
(Ib-vii)

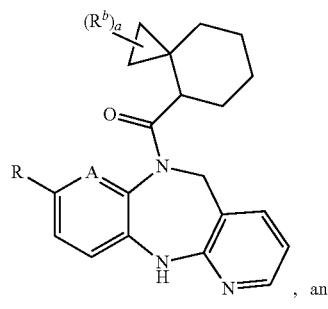
(Ib-viii)

, and

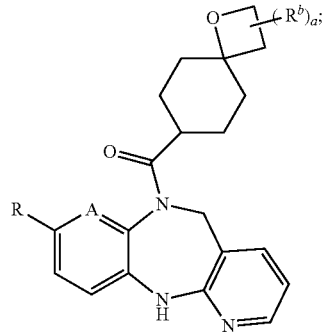
(Ib-ix)

wherein a is 0, 1, or 2; when a is 2, the two $R^b$ substituents are attached to the same or different substitutable positions on spiro ring;
or a pharmaceutically acceptable salt thereof.

9. The compound of claim 1, wherein each occurrence of $R^4$, $R^6$, $R^7$, $R^9$, $R^{11}$ and $R^{12}$, when present, is independently selected from the group consisting of hydrogen and $C_{1-6}$alkyl optionally substituted with one to four halogens; or a pharmaceutically acceptable salt thereof.

10. The compound of claim 3, wherein $R^8$ is hydrogen or $C_{1-4}$alkyl; or a pharmaceutically acceptable salt thereof.

11. The compound of claim 2, wherein:
R is selected from the group consisting of:
(1) hydrogen,
(2) halogen, (3) $C_{1-6}$alkyl, optionally substituted with one to four substituents independently selected from (a) halogen, (b) —CN, (c) —OR$^d$, (d) —(C=O)—R$^e$, (e) —NR$^x$R$^y$, and (f) heterocyclyl; wherein R$^d$ is hydrogen or $C_{1-4}$alkyl optionally substituted with heterocyclyl;

R$^e$ is hydroxyl or heterocyclyl;

each of R$^x$ and R$^y$ is independently selected from the group consisting of (i) hydrogen, (ii) $C_{1-6}$alkyl, which is optionally substituted with one to four substituents independently selected from halogen, —O—$C_{1-4}$alkyl, $C_{3-6}$cycloalkyl, and heterocyclyl, (iii) $C_{3-6}$cycloalkyl, which is optionally substituted with one to four substituents independently selected from halogen, and $C_{1-4}$alkyl, which is optionally substituted with one to four halogens, and (iv) heterocyclyl;

(4) —O—$C_{1-6}$alkyl, (5) —(C=O)$_t$—NR$^x$R$^y$, wherein t is 0 or 1; each of R$^x$ and R$^y$ is independently selected from the group consisting of (a) hydrogen, (b) $C_{1-6}$alkyl, (c) $C_{3-6}$cycloalkyl, (d) phenyl optionally substituted with one to four halogens, and (e) heterocyclyl;

wherein the $C_{1-6}$alkyl of (b) is optionally substituted with one to four substituents independently selected from halogen, —O—$C_{1-4}$alkyl, $C_{3-6}$cycloalkyl, and heterocyclyl; and the $C_{3-6}$cycloalkyl of (c) is optionally substituted with one to four substituents independently selected from halogen and $C_{1-4}$alkyl optionally substituted with one to four halogens, and (6) —(C=O)$_t$-heterocyclyl, wherein t is 0 or 1; and the heterocyclyl is optionally substituted with one to four substituents independently selected from R$^b$;

or a pharmaceutically acceptable salt thereof.

12. The compound of claim 8, wherein:
R is selected from the group consisting of:
(1) hydrogen,
(2) $C_{1-6}$alkyl, optionally substituted with one to four substituents independently selected from halogen, —CN, and —OR$^d$; wherein R$^d$ is hydrogen or $C_{1-4}$alkyl optionally substituted with heterocyclyl;
(3) —NR$^j$R$^k$, wherein each of R$^j$ and R$^k$ is independently selected from the group consisting of hydrogen and $C_{1-6}$alkyl; wherein the $C_{1-6}$alkyl is optionally substituted with one to four halogens, and
(4) —(C=O)-heterocyclyl, wherein the heterocyclyl is optionally substituted with halogen or $C_{1-6}$alkyl; and
(5) heterocyclyl, optionally substituted with one to four substituents independently selected from the group consisting of halogen, oxo, —O—$C_{1-6}$alkyl, $C_{1-6}$alkyl optionally substituted with one to four halogens, —NR$^j$R$^k$, and heterocyclyl optionally substituted with halogen or hydroxyl; wherein each of R$^j$ and R$^k$ is independently selected from the group consisting of hydrogen and $C_{1-6}$alkyl;
wherein each occurrence of the heterocyclyl of (2), (4) and (5) is independently selected from the group consisting of azaindolyl, azetidinyl, 1,4-dioxanyl, imidazolyl, isoindolinyl, isoxazolyl, morpholinyl, oxazolidinyl, piperidinyl, pyridinyl, pyrazolyl, pyrrolidinyl, tetrahydropyranyl, and thiazolyl;

or a pharmaceutically acceptable salt thereof.

13. The compound of claim 3, wherein:
each occurrence of R$^b$ is independently selected from the group consisting of:
(1) halogen,
(2) hydroxyl,
(3) —CN,
(4) oxo,
(5) —O—$C_{1-6}$alkyl,
(6) —(C=O)—R$^c$, wherein R$^c$ is selected from the group consisting of hydrogen, hydroxyl, $C_{1-6}$alkyl, —O—$C_{1-6}$alkyl, —NR$^j$R$^k$, and heterocyclyl; wherein the heterocyclyl is optionally substituted with one to four substituents independently selected from halogen and $C_{1-6}$alkyl; and each of R$^j$ and R$^k$ is independently selected from the group consisting of hydrogen and $C_{1-6}$alkyl,
(7) $C_{1-6}$alkyl, optionally substituted with one to four halogens,
(8) phenyl, optionally substituted with one to four halogens, and
(9) heterocyclyl, optionally substituted with one to four substituents independently selected from halogen, oxo, $C_{1-6}$alkyl optionally substituted with one to four halogens, —O—$C_{1-6}$alkyl, heterocyclyl optionally substituted with halogen or hydroxyl, and —NR$^j$R$^k$; wherein each of R$^j$ and R$^k$ is independently selected from the group consisting of hydrogen and $C_{1-6}$alkyl;

or a pharmaceutically acceptable salt thereof.

14. The compound of claim 8, wherein:
each occurrence of R$^b$ is independently selected from the group consisting of:
(1) halogen,
(2) hydroxyl,
(3) oxo,
(4) —O—$C_{1-6}$alkyl,
(5) —(C=O)—R$^c$, wherein R$^c$ is selected from the group consisting of hydrogen, hydroxyl, and $C_{1-6}$alkyl, and
(6) $C_{1-6}$alkyl, optionally substituted with one to four halogens;

or a pharmaceutically acceptable salt thereof.

15. The compound of claim 3,
wherein:
each occurrence of the heterocyclyl of R and R$^b$ is independently selected from the group consisting of:
8-azabicyclo[3.2.1]octanyl, 2-azaspiro[3.3]heptanyl, azaindolyl, azetidinyl, 2,5-diazabicyclo[2.2.2]octanyl, 1,6-diazaspiro[3.3]heptanyl, 2,6-diazaspiro[3.3]heptanyl, 2,3-dihydro-1,4-dioxinyl, 3,4-dihydro-2H-pyrido[3,2-b][1,4]oxazinyl, 5,6-dihydro-4H-pyrrolo[1,2-b]pyrazolyl, 1,4-dioxanyl, hexahydro-1H-furo[3,4-c]pyrrolyl, 1,2,4,5,6,6a-hexahydropyrrolo[3,4-b]pyrrolyl, imidazolyl, 1H-imidazo[4,5-b]pyridinyl, isoindolinyl, isoxazolyl, morpholinyl, octahydrocyclopenta[1,4]oxazinyl, octahydro-1H-imidazo[4,5-c]pyridinyl, 2-oxa-5-azabicyclo[2.2.1]heptanyl, 3-oxa-6-azabicyclo[3.2.0]heptanyl, 6-oxa-3-azabicyclo[3.1.1]heptanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 2-oxa-6-azaspiro[3.3]heptanyl, 4-oxa-7-azaspiro[2.5]octanyl, 6-oxa-2-azaspiro[3.4]octanyl, 7-oxa-2,5-diazaspiro[3.4]octanyl, 3-oxa-1,7-diazaspiro[4.4]nonanyl, 1,4-oxazepanyl, oxazolidinyl, oxetanyl, piperazinyl, piperidinyl, pyrazolo[1,5-b]pyridazinyl, pyrazolyl, pyridazinyl, pyridinyl, pyrimidinyl, pyrrolidinyl, pyrrolyl, tetrahydrofuranyl, 5,6,7,8-tetrahydroimidazo[1,5-a]pyrazinyl, tetrahydropyranyl, 4,5,6,7-tetrahydropyrazolo[1,5-a]pyrazinyl, 4,5,6,7-tetrahydro-2H-pyrazolo[4,3-c]pyridinyl, 1,2,3,6-tetrahydropyridinyl, 1,2,3,4-tetrahydropyrrolo[1,2-a]pyrazinyl, 4,5,6,7-tetrahydro-

[1,2,3]triazolo[1,5-a]pyrazinyl, 5,6,7,8-tetrahydro-[1,2,4]triazolo[4,3-a]pyrazinyl, 5,6,7,8-tetrahydro-[1,2,4]triazolo[1,5-a]pyrazinyl, thiazolyl, and thiophenyl;

or a pharmaceutically acceptable salt thereof.

16. The compound of claim 1 selected from the group consisting of:
- 6-{[(3r,8r)-3-Methoxybicyclo[3.2.1]oct-8-yl]carbonyl}-8-morpholin-4-yl-6,11-dihydro-5H-pyrido[2,3-b][1,5]benzodiazepine,
- 6-{[(3s,8s)-3-methoxybicyclo[3.2.1]oct-8-yl]carbonyl}-8-morpholin-4-yl-6,11-dihydro-5H-pyrido[2,3-b][1,5]benzodiazepine,
- 2-Methyl-2-[6-(6,7,8,9-tetrahydro-5H-benzo[7]annulen-7-ylcarbonyl)-6,11-dihydro-5H-pyrido[2,3-b][1,5]benzodiazepin-8-yl]propanenitrile,
- 6-(spiro[2.5]oct-1-ylcarbonyl)-6,11-dihydro-5H-pyrido[2,3-b][1,5]benzodiazepine,
- 6-(spiro[2.4]hept-1-ylcarbonyl)-6,11-dihydro-5H-pyrido[2,3-b][1,5]benzodiazepine,
- 6-(bicyclo[1.1.1]pent-1-ylcarbonyl)-6,11-dihydro-5H-pyrido[2,3-b][1,5]benzodiazepine,
- 6-[(3-phenylbicyclo[1.1.1]pent-1-yl)carbonyl]-6,11-dihydro-5H-pyrido[2,3-b][1,5]benzodiazepine,
- 6-(bicyclo[3.1.1]hept-1-ylcarbonyl)-6,11-dihydro-5H-pyrido[2,3-b][1,5]benzodiazepine,
- 6-(5,11-dihydro-6H-pyrido[2,3-b][1,5]benzodiazepin-6-ylcarbonyl)spiro[3.3]heptane-2-carboxylic acid,
- 8-morpholin-4-yl-6-(spiro[3.3]hept-2-ylcarbonyl)-6,11-dihydro-5H-pyrido[2,3-b][1,5]benzodiazepine,
- 6-(2,3-dihydro-1H-inden-2-ylcarbonyl)-6,11-dihydro-5H-pyrido[2,3-b][1,5]benzodiazepine,
- 6-(2,3-dihydro-1H-inden-1-ylcarbonyl)-6,11-dihydro-5H-pyrido[2,3-b][1,5]benzodiazepine,
- 2-[6-(2,3-dihydro-1H-inden-2-ylcarbonyl)-6,11-dihydro-5H-pyrido[2,3-b][1,5]benzodiazepin-8-yl]-2-methylpropanenitrile,
- 6-[(3aS,6aS)-octahydropentalen-1-ylcarbonyl]-6,11-dihydro-5H-pyrido[2,3-b][1,5]benzodiazepine,
- (1R,5S)-6-(5,11-dihydro-6H-pyrido[2,3-b][1,5]benzodiazepin-6-ylcarbonyl)bicyclo[3.2.1]octan-2-ol,
- 6-[(2S)-bicyclo[2.2.1]hept-2-ylcarbonyl]-6,11-dihydro-5H-pyrido[2,3-b][1.5]benzodiazepine,
- 6-(bicyclo[2.2.1]hept-1-ylcarbonyl)-8-morpholin-4-yl-6,11-dihydro-5H-pyrido[2,3-b][1,5]benzodiazepine,
- 6-[(6,6-difluorobicyclo[3.1.0]hex-3-yl)carbonyl]-8-morpholin-4-yl-6,11-dihydro-5H-pyrido[2,3-b][1,5]benzodiazepine,
- 6-{[(1R,3r,5S)-6,6-difluorobicyclo[3.1.0]hex-3-yl]carbonyl}-8-morpholin-4-yl-6,11-dihydro-5H-pyrido[2,3-b][1,5]benzodiazepine,
- 8-morpholin-4-yl-6-[(3aR,6aR)-octahydropentalen-1-ylcarbonyl]-6,11-dihydro-5H-pyrido[2,3-b][1,5]benzodiazepine,
- 6-(1,2,3,4-tetrahydronaphthalen-2-ylcarbonyl)-6,11-dihydro-5H-pyrido[2,3-b][1.5]benzodiazepine,
- methyl 4-(5,11-dihydro-6H-pyrido[2,3-b][1,5]benzodiazepin-6-ylcarbonyl)bicyclo[2.2.2]octane-1-carboxylate,
- 6-[(2-methyl-1,2,3,4-tetrahydronaphthalen-2-yl)carbonyl]-6,11-dihydro-5H-pyrido[2,3-b][1,5]benzodiazepine,
- 6-(bicyclo[2.2.2]oct-1-ylcarbonyl)-6,11-dihydro-5H-pyrido[2,3-b][1,5]benzodiazepine,
- 6-[(3s,5s,7s)-tricyclo[3.3.1.1~3.7~]dec-1-ylcarbonyl]-6,11-dihydro-5H-pyrido[2,3-b][1,5]benzodiazepine,
- 4-(5,11-dihydro-6H-pyrido[2,3-b][1,5]benzodiazepin-6-ylcarbonyl)bicyclo[2.2.2]oct-2-ene-1-carbonitrile,
- 1-[4-(5,11-dihydro-6H-pyrido[2,3-b][1,5]benzodiazepin-6-ylcarbonyl)bicyclo[2.2.2]oct-2-en-1-yl]ethanone,
- 6-[(4-pentylbicyclo[2.2.2]oct-1-yl)carbonyl]-6,11-dihydro-5H-pyrido[2,3-b][1,5]benzodiazepine,
- 6-(bicyclo[3.1.1]hept-1-ylcarbonyl)-6,11-dihydro-5H-pyrido[2.3-b][1,5]benzodiazepine,
- 6-[(8,8-difluorobicyclo[3.2.1]oct-3-yl)carbonyl]-6,11-dihydro-5H-pyrido[2,3-b][1,5]benzodiazepine,
- 6-[(3-fluorotricyclo[3.3.1.1~3,7~]dec-1-yl)carbonyl]-8-morpholin-4-yl-6,11-dihydro-5H-pyrido[2,3-b][1,5]benzodiazepine,
- 6-[(3,5-difluorotricyclo[3.3.1.1~3,7~]dec-1-yl)carbonyl]-8-morpholin-4-yl-6,11-dihydro-5H-pyrido[2,3-b][1,5]benzodiazepine,
- 8-Morpholin-4-yl-6-(1,2,3,4-tetrahydronaphthalen-2-ylcarbonyl)-6,11-dihydro-5H-pyrido[2,3-b][1,5]benzodiazepine,
- 2-[6-(6,7,8,9-Tetrahydro-5H-benzo[7]annulen-7-ylcarbonyl)-6,11-dihydro-5H-pyrido[2,3-b][1,5]benzodiazepin-8-yl]propan-2-ol,
- 2-Morpholin-4-yl-11-(6,7,8,9-tetrahydro-5H-benzo[7]annulen-7-ylcarbonyl)-10,11-dihydro-5H-dipyrido[2,3-b:2',3'-e][1,4]diazepine,
- 4-[6-(6,7,8,9-Tetrahydro-5H-benzo[7]annulen-7-ylcarbonyl)-6,11-dihydro-5H-pyrido[2,3-b][1,5]benzodiazepin-8-yl]pyrrolidin-2-one,
- 3-[6-(6,7,8,9-Tetrahydro-5H-benzo[7]annulen-7-ylcarbonyl)-6,11-dihydro-5H-pyrido[2,3-b][1,5]benzodiazepin-8-yl]-1,3-oxazolidin-2-one,
- 4-Methyl-5-[6-(6,7,8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one, and
- (4R)-4-(1-Methylethyl)-3-[6-(6,7, 8,9-tetrahydro-5H-benzo[7]annulen-7-ylcarbonyl)-6,11-dihydro-5H-pyrido[2,3-b][1,5]benzodiazepin-8-yl]-1,3-oxazolidin-2-one, or a pharmaceutically acceptable salt thereof.

17. A composition which comprises an inert carrier or excipient and a compound of claim 1 or a pharmaceutically acceptable salt thereof.

18. A method for treating cancer associated with mutant IDH enzyme activity in a mammalian subject which comprises administering to the subject an effective amount of the compound of claim 1 or a pharmaceutically acceptable salt thereof.

19. The method of claim 18, wherein the disease or disorder associated with mutant IDH enzyme activity is a cancer selected from the group consisting of glioma, glioblastoma multiforme, paraganglioma, supratentorial primordial neuroectodermal tumors, acute myeloid leukemia (AML), breast cancer, prostate cancer, thyroid cancer, colon cancer, chondrosarcoma, cholangiocarcinoma, peripheral T-cell lymphoma, and melanoma.

20. The method of claim 19, wherein the cancer is selected from glioma, glioblastoma multiforme, acute myeloid leukemia, and breast cancer.

* * * * *